United States Patent
Gao et al.

(10) Patent No.: US 10,494,328 B2
(45) Date of Patent: Dec. 3, 2019

(54) AMINATION AND HYDROXYLATION OF ARYLMETAL COMPOUNDS

(71) Applicant: WILLIAM MARSH RICE UNIVERSITY, Houston, TX (US)

(72) Inventors: Hongyin Gao, Houston, TX (US); Zhe Zhou, Houston, TX (US); Laszlo Kurti, Bellaire, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 15/659,320

(22) Filed: Jul. 25, 2017

(65) Prior Publication Data

US 2018/0057444 A1 Mar. 1, 2018

Related U.S. Application Data

(60) Provisional application No. 62/366,483, filed on Jul. 25, 2016.

(51) Int. Cl.

| | | |
|---|---|---|
| C07C 209/66 | (2006.01) |
| C07B 41/02 | (2006.01) |
| C07D 295/135 | (2006.01) |
| C07D 307/79 | (2006.01) |
| C07D 317/66 | (2006.01) |
| C07D 317/46 | (2006.01) |
| C07C 319/20 | (2006.01) |
| C07D 317/28 | (2006.01) |
| C07D 309/12 | (2006.01) |
| C07D 213/73 | (2006.01) |
| C07D 213/04 | (2006.01) |
| C07D 209/04 | (2006.01) |
| C07D 277/82 | (2006.01) |
| C07D 333/20 | (2006.01) |
| C07D 307/91 | (2006.01) |
| C07D 209/88 | (2006.01) |
| C07J 41/00 | (2006.01) |
| C07D 333/16 | (2006.01) |
| C07C 41/26 | (2006.01) |
| C07D 317/64 | (2006.01) |
| C07D 295/096 | (2006.01) |
| C07D 317/20 | (2006.01) |
| C07B 43/04 | (2006.01) |
| C07C 37/01 | (2006.01) |
| C07C 37/055 | (2006.01) |
| C07D 311/58 | (2006.01) |
| C07D 215/38 | (2006.01) |
| C07C 37/64 | (2006.01) |
| C07C 303/30 | (2006.01) |
| C07D 333/36 | (2006.01) |
| C07C 213/02 | (2006.01) |
| C07C 227/06 | (2006.01) |

(52) U.S. Cl.
CPC ............ *C07C 209/66* (2013.01); *C07B 41/02* (2013.01); *C07B 43/04* (2013.01); *C07C 37/01* (2013.01); *C07C 37/055* (2013.01); *C07C 37/64* (2013.01); *C07C 41/26* (2013.01); *C07C 213/02* (2013.01); *C07C 227/06* (2013.01); *C07C 303/30* (2013.01); *C07C 319/20* (2013.01); *C07D 209/04* (2013.01); *C07D 209/88* (2013.01); *C07D 213/04* (2013.01); *C07D 213/73* (2013.01); *C07D 215/38* (2013.01); *C07D 277/82* (2013.01); *C07D 295/096* (2013.01); *C07D 295/135* (2013.01); *C07D 307/79* (2013.01); *C07D 307/91* (2013.01); *C07D 309/12* (2013.01); *C07D 311/58* (2013.01); *C07D 317/20* (2013.01); *C07D 317/28* (2013.01); *C07D 317/46* (2013.01); *C07D 317/64* (2013.01); *C07D 317/66* (2013.01); *C07D 333/16* (2013.01); *C07D 333/20* (2013.01); *C07D 333/36* (2013.01); *C07J 41/0011* (2013.01); *C07C 2601/02* (2017.05); *C07C 2601/04* (2017.05); *C07C 2601/14* (2017.05); *C07C 2603/18* (2017.05); *C07C 2603/26* (2017.05)

(58) Field of Classification Search
CPC ..... C07C 319/20; C07C 209/66; C07C 37/01; C07D 333/16; C07D 295/096; C07D 209/88; C07D 277/82; C07D 309/12; C07D 317/20; C07D 307/91; C07D 213/04

See application file for complete search history.

(56) References Cited

PUBLICATIONS

Davis et al., The Mechanisms of Hydroxylation of Organometallic Reagents by 2-sulfonyloxaziridines, Tetrahedron Letters, vol. 28, No. 43, pp. 5115-5118, 1987.*
Berman AM and Johnson JS. "Copper-Catalyzed Electrophilic Amination of Organozinc Nucleophiles: Documentation of O-Benzoyl Hydroxylamines as Broadly Useful R2N(+) and RHN(+) Synthons." *J. Org. Chem.*, 71, 1, 219-224, 2006.
Chiba S. and Narasaka K. "Simple Molecules, Highly Efficient Amination." *Amino Group Chem.*, 1-54, 2008.

(Continued)

*Primary Examiner* — Deepak R Rao
(74) *Attorney, Agent, or Firm* — Parker Highlander PLLC

(57) ABSTRACT

In one aspect, the present disclosure provides methods of preparing a primary or secondary amine and hydroxylated aromatic compounds. In some embodiments, the aromatic compound may be unsubstituted, substituted, or contain one or more heteroatoms within the rings of the aromatic compound. The methods described herein may be carried out without the need for transition metal catalysts or harsh reaction conditions.

16 Claims, 5 Drawing Sheets

(56) References Cited

PUBLICATIONS

Corpet M and Gosmini C. "Recent advances in electrophilic amination reactions." *Synthesis*, 46, 17, 2258-2271, 2014.
Erdik E. "Electrophilic C-amination with O-substituted hydroxylamines." *Chem. Hydroxylamines, Oximes Hydroxamic Acids, Part 1*, S. Patai, Ed. Wiley, pp. 304-341, 2009.
Gao et al. "Rapid heteroatom transfer to arylmetals utilizing multifunctional reagent scaffolds." *Nat. Chem.* Published online. Nov. 28, 2016.
Garrett Ce and Prasad K. "The Art of Meeting Palladium Specifications in Active Pharmaceutical Ingredients Produced by Pd—Catalyzed Reactions." *Adv. Synth. Catal.* 346, 8, 889-900, 2004.
Kholdeeva OA and Zalomaeva OV. "Recent advances in transition-metal-catalyzed selective oxidation of substituted phenols and methoxyarenes with environmentally benign oxidants." *Coordination Chemistry Reviews*. 306:302-330, 2016.
Kitamura M. et al. "Synthesis of Primary Amines and N-Methylamines by the Electrophilic Amination of Grignard Reagents with 2-Imidazolidinone O-Sulfonyloxime." *Bull. Chem. Soc. Jpn.* 76:1063-1070, 2003.
Kitamura M. et al. "Synthesis of Primary Amines by the Electrophilic Amination of Grignard Reagents with 1,3-Dioxolan-2-one O-Sulfonyloxime." *Org. Lett.* 6:4619-4621, 2004.
Klatt T. et al. "Strategies to Prepare and Use Functionalized Organometallic Reagents." *J. Org Chem.* 79, 10, 4253-4269, 2014.
Knochel P. et al. "Highly functionalized organomagnesium reagents prepared through halogen-metal exchange." *Angew. Chem., Int. Ed.* 42:4302-4320, 2003.
Knochel P. "Organomagnesium and Organozinc Chemistry." *Organomet. Synth.*, 223-372, 2013.
Mlynarski SN et al. "Direct Stereospecific Amination of Alkyl and Aryl Pinacol Boronates." *J. Am. Chem. Soc.* 134:16449-16451, 2012.
Mosrin M et al. "Regio- and Chemoselective Multiple Functionalization of Chloropyrazine Derivatives. Application to the Synthesis of Coelenterazine." *Org. Lett.* 11, 15, 3406-3409, 2009.
Qiu F. And Norwood DL. "Identification of pharmaceutical impurities." *J. Liq. Chromatogr. Relat. Technol.* 30:877-935, 2007.
Starkov P. et al. "Electrophilic Amination: The Case of Nitrenoids." *Chem.—Eur. J.*, 21:5278-5300, 2015.
Tezuka et al. "Direct Hydroxylation and Amination of Arenes via Deprotonative Cupration." *J. Am. Chem. Soc.*, 138, 29, 9166-9171, 2016.
Tsutsui H et al. "Preparation of primary amines by the alkylation of O-sulfonyloximes of benzophenone derivatives with Grignard reagents." *Bull. Chem. Soc. Jpn.* 72:1869-1878, 1999.
Welch CJ et al. "Adsorbent Screening for Metal Impurity Removal in Pharmaceutical Process Research." *Organic Process Research & Development.* 9, 2, 198-205, 2005.
Wunderlich SH et al. "(tmp)(2)Zn × 2 MgCl(2) × 2 LiCl: a chemoselective base for the directed zincation of sensitive arenes and heteroarenes." *Angew. Chem., Int. Ed.* 46, 40, 7685-7688, 2007.
Wunderlich SH et al. "Efficient Mono-and bis-Functionalization of 3,6-Ddichloropyridazine using (TMP)2Zn×2MgCl2×2LiCl." *Chem. Commun.* 47, 6387-6389, 2008.
Zhu C et al. "The Elusive Metal-Free Primary Amination of Arylboronic Acids: Synthetic Studies and Mechanism by Density Functional Theory." *J. Am. Chem. Soc.* 134, 44, 18253-18256, 2012.
Zhu C et al. "Mild and Rapid Hydroxylation of Aryl/Heteroaryl Boronic Acids and Boronate Esters with N-Oxides." Org. Lett., 14, 13, 494-3497, 2012.

\* cited by examiner

AMINATION AND HYDROXYLATION OF ARYLMETAL COMPOUNDS

This application claims the benefit of U.S. Provisional Application Ser. No. 62/366,483, filed on Jul. 25, 2016, the entirety of which is incorporated herein by reference.

This invention was made with government support under Grant Number R01 GM114609 awarded by the National Institutes of Health and Grant Number CHE-1546097 awarded by the National Science Foundation. The government has certain rights in the invention. This research was also supported by the Robert A. Welch Foundation under Grant No. C-1764.

BACKGROUND

1. Field

This disclosure relates to the methods of aminating and hydroxylating aromatic compounds. In some aspects, the present disclosure provides methods of introducing an amine or hydroxy group to an aromatic compound without the use of a transition metal catalyst.

2. Related Art

Nitrogen- and oxygen-substituted aromatic rings, such as anilines and phenols, appear as substructures in a large number of industrially and commercially significant organic compounds such as agrochemicals, active pharmaceutical ingredients and functional materials (Rappoport, 2004; Hili and Yudin, 2006; Rappoport, 2007; Ricci, 2008). For example, primary anilines (Ar—$NH_2$) and phenols (Ar—OH) are used as intermediates or building blocks for the preparation of azo dyes, drug candidates as well as polyanilines (Rappoport, 2004; Rappoport, 2007). Anilines are mostly prepared via one of the following bluemethods: (a) reduction of aromatic nitro compounds (Blaser, et al., 2001; Mallat, et al., 2008; Blaser, et al., 2009); (b) transition metal-catalyzed (Pd, Cu) cross-coupling of haloarenes and arylboronic acids with ammonia or substituted primary and secondary amines (Wolfe, et al., 1998; Shen and Hartwig, 2006; Vo and Hartwig, 2009; Lundgren, et al., 2010); (c) transition metal-catalyzed (Pd, Ni or Cu) electrophilic amination of various organometallics (Klinkenberg and Hartwig, 2011; Qiao and Lam, 2011a; Qiao and Lam, 2011b; Rao and Fu, 2011; Berman and Johnson, 2004) (e.g., Li, Zn and B); (d) nucleophilic aromatic substitution ($S_NAr$) and nucleophilic substitution of hydrogen in electron-deficient systems (Barker and Jarvo, 2009; Barker and Jarvo, 2011; Olson, 2011; Rucker, et al., 2012; Makosza, 2010) as well as the (e) direct C—H amination (Alvarez-Builla, et al., 2011; Makosza, 2011; Terrier, 2013) of aromatic rings. Additionally, phenols are often prepared via the following methods: (a) $S_NAr$ in heteroaromatic systems (Rappoport, 2004; Barker and Jarvo, 2011; Rucker, et al., 2012); (b) oxidation of arylboronic acids and derivatives (Makosza, 2014) and (c) metal-catalyzed direct hydroxylation of aromatic rings (Kawano, et al., 2010; Yoo, et al., 2011; Jiao, et al., 2016; Chinnusamy, et al., 2014;' Alonso, et al., 2010).

Despite the importance of anilines and phenols, the direct and regioselective introduction of a primary amino ($NH_2$) or hydroxyl (OH) group onto a functionalized aromatic ring under mild, operationally simple and environmentally friendly conditions, such as low temperature, absence of excess reagents or transition metal catalysts and additives, has been an unmet synthetic need. Nearly all the methods that are catalyzed or mediated by transition metals and their complexes require forcing conditions (high temperature, high pressure, strong oxidants, etc.), which results in limited functional group tolerance. From a practical and environmental point of view, transition metal-free processes are much preferred, especially in the pharmaceutical industry, where the removal of undesired metal contamination can be expensive (Enthaler, 2011; Guan, 2014; Thirunavukkarasu, et al., 2014). While the readily available and inexpensive aryl-Grignard (Kholdeeva and Zalomaeva, 2016; Garrett and Prasa, 2004; Welch, et al., 2005; Qiu and Norwood, 2007) and aryllithium (Garrett and Prasa, 2004) reagents are commonly used in reactions, the direct primary amination of arylmetal reagents is exceedingly problematic as most hydroxylamine-derived aminating agents such as $H_2N$—OR, where OR is a leaving group undergo rapid deprotonation, thus consume a total of three (3) equivalents of the precious arylmetal reagent and tend to give poor yield of the desired primary arylamine upon workup (FIG. 2, A) (Knochel, et al., 2003). In addition to these limited primary methods, a few two step procedures exists. In the first approach (FIG. 2, A), an electrophilic nitrogen source is reacted with an arylmetal and, after C—N bond formation, the activating group is removed typically under harsh conditions such as strongly acidic hydrolysis at elevated temperatures (Klatt, et al., 2014; Erdik, 2009; Corpet and Gosmini, 2014; Starkov, et al., 2015). Additionally, the free primary amine that is then generated has to be liberated from its salt form using basic conditions. Thus, this approach prohibits the use of highly functionalized arylmetal reagents or those reagents that have acid- or base-sensitive functionalities which limits the usefulness of this method. Another approach (FIG. 2, B) uses an O-alkylhydroxylamine, such as methoxyamine, that is first treated with MeLi and the resulting lithium amide may only be reacted with half of an equivalent of the arylmetal reagent that is to be aminated (Knochel, et al., 2003; Rappoport, 2008; Knochel, 2013). Although the arylamine can be obtained in the free-base form right after the aqueous workup, the need to use two separate organometallic reagents in excess and the modest overall efficiency/yield are the two obvious drawbacks of this method. There are a handful of examples (FIG. 2, C) in which arylboronic acids or borate esters may be converted to the primary arylamines in the absence of transition metal catalysts (Tsutsui, et al., 1999; Kitamura, et al., 2003; Kitamura, et al., 2004; Chiba and Narasaka, 2008). Unlike these arylboronic acids or borate esters, the direct hydroxylation of arylmagnesium or aryllithium reagents is even more difficult due to numerous side reactions (Mlynarski, et al., 2012). One method stands out (FIG. 2, D), as being quite general, however, it uses oxygen (O2) in air at high pressure (250 psi) and requires a specialized flow reactor system (Zhu, et al., 2012) and thus not readily amendable to all possible substrates and commercial use. Furthermore, currently, there are no general methods/reagents available for the direct hydroxylation of structurally diverse arylmetal reagents that would allow the efficient synthesis of phenols in an operationally simple and functional group-tolerant fashion.

Clearly, there remains a need for new synthetic methodologies for generating primary aryl amines or phenols.

SUMMARY

Thus, the present disclosure provides methods of synthesizing primary aryl amines or phenols. In some embodiments, the present disclosure provides methods of preparing an aminoaromatic group or a hydroxyaromatic group comprising:
(A) admixing a metal aromatic compound with an oxaziridine compound to form a first reaction mixture under conditions sufficient to cause a reaction to obtain an anionic intermediate;
(B) admixing a weak acid with the anionic intermediate and the first reaction mixture to obtain a second reaction mixture under conditions sufficient to obtain an aminoaromatic group or a hydroxyaromatic group.

In some embodiments, the metal of the metal aromatic compound is attached to one of the carbon atoms of the aromatic ring. The metal of the metal aromatic compound may be a magnesium halide or lithium. In some embodiments, the metal aromatic compound comprises from 1 to 8 aromatic rings. The aromatic rings may be fused. In other embodiments, the aromatic rings are attached in a pendent fashion. In still other embodiments, the aromatic rings are both fused and attached in a pendent fashion.

The metal aromatic compound is not substituted or substituted. In some embodiments, metal aromatic compound is substituted 1, 2, 3, 4, or 5 times and may be substituted with a substituent wherein the substituent is amino, aminosulfonyl, carboxy, cyano, halo, hydroxy, hydroxyamino, hydroxysulfonyl, mercapto, nitro, oxo, or thio; or acyl$_{(C \le 8)}$, alkoxy$_{(C \le 8)}$, cycloalkoxy$_{(C \le 8)}$, alkenyloxy$_{(C \le 8)}$, aryloxy$_{(C \le 8)}$, aralkoxy$_{(C \le 8)}$, acyloxy$_{(C \le 8)}$, cycloalkylalkoxy$_{(C \le 8)}$, heterocycloalkylalkoxy$_{(C \le 8)}$, heterocycloalkoxy$_{(C \le 8)}$, alkylthio$_{(C \le 8)}$, cycloalkylthio$_{(C \le 8)}$, amido$_{(C \le 8)}$, alkylamino$_{(C \le 8)}$, dialkylamino$_{(C \le 8)}$, alkylsulfonyl$_{(C \le 8)}$, arylsulfonyl$_{(C \le 8)}$, or a substituted version of these groups, or a protected amine group, a protected hydroxyl group, or a protected thiol group. In one embodiment, the metal aromatic compound is substituted with a substituent wherein the substituent is aminosulfonyl, cyano, halo, nitro, or oxo; or acyl$_{(C \le 8)}$, alkoxy$_{(C \le 8)}$, cycloalkoxy$_{(C \le 8)}$, alkenyloxy$_{(C \le 8)}$, aryloxy$_{(C \le 8)}$, aralkoxy$_{(C \le 8)}$, cycloalkylalkoxy$_{(C \le 8)}$, heterocycloalkoxy$_{(C \le 8)}$, heterocycloalkoxy$_{(C \le 8)}$, alkylthio$_{(C \le 8)}$, cycloalkylthio$_{(C \le 8)}$, amido$_{(C \le 8)}$, alkylsulfonyl$_{(C \le 8)}$, arylsulfonyl$_{(C \le 8)}$, or a substituted version of these groups, or a protected amine group, a protected hydroxyl group, or a protected thiol group. In some embodiments, the metal aromatic compound is substituted with a substituent, wherein the substituent is 1, 2, 3, 4, or 5 fused heteroaryl$_{(C \le 12)}$ rings or fused heterocycloalkyl$_{(C \le 12)}$ rings, wherein these rings are unsubstituted or substituted.

In some embodiments, the metal aromatic compound comprises from 6 carbon atoms to 30 carbon atoms. The metal aromatic compound may be comprised from 6 carbon atoms to 18 carbon atoms. In some embodiments, the metal aromatic compound comprises from 6 carbon atoms to 12 carbon atoms.

In other aspects, the oxaziridine compound is a compound of the formula:

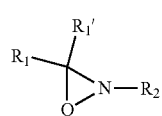

(I)

wherein:
R$_1$ and R$_1$' are each independently alkyl$_{(C \le 12)}$, cycloalkyl$_{(C \le 12)}$, aryl$_{(C \le 12)}$, or a substituted version of any of these groups, or R$_1$ and R$_1$' are taken together and are a cycloalkanediyl$_{(C \le 18)}$ or substituted cycloalkanediyl$_{(C \le 18)}$; and R$_2$ is hydrogen or alkyl$_{(C \le 12)}$, aryl$_{(C \le 12)}$, aralkyl$_{(C \le 12)}$, or a substituted version of any of these three groups.

In some embodiments, R$_1$ and R$_1$' are taken together and a cycloalkanediyl$_{(C \le 18)}$ or a substituted cycloalkanediyl$_{(C \le 18)}$. The cycloalkanediyl$_{(C \le 18)}$ or substituted cycloalkanediyl$_{(C \le 18)}$ may be a bicycloalkanediyl$_{(C \le 18)}$ or substituted bicycloalkanediyl$_{(C \le 18)}$. The bicycloalkanediyl$_{(C \le 18)}$ or substituted bicycloalkanediyl$_{(C \le 18)}$ may contain one or more carbon atoms adjacent to the carbon atom of the oxaziridine ring is a quaternary substituted carbon atom. In some embodiments, one of the adjacent carbon atoms is a quaternary substituted carbon atom. In other embodiments, both of the adjacent carbon atoms is a quaternary substituted carbon atom. R$_2$ may be hydrogen. R$_2$ may be alkyl$_{(C \le 8)}$ such as methyl. R$_2$ may be aralkyl$_{(C \le 8)}$ such as benzyl. In some embodiments, the oxaziridine compound is further defined as:

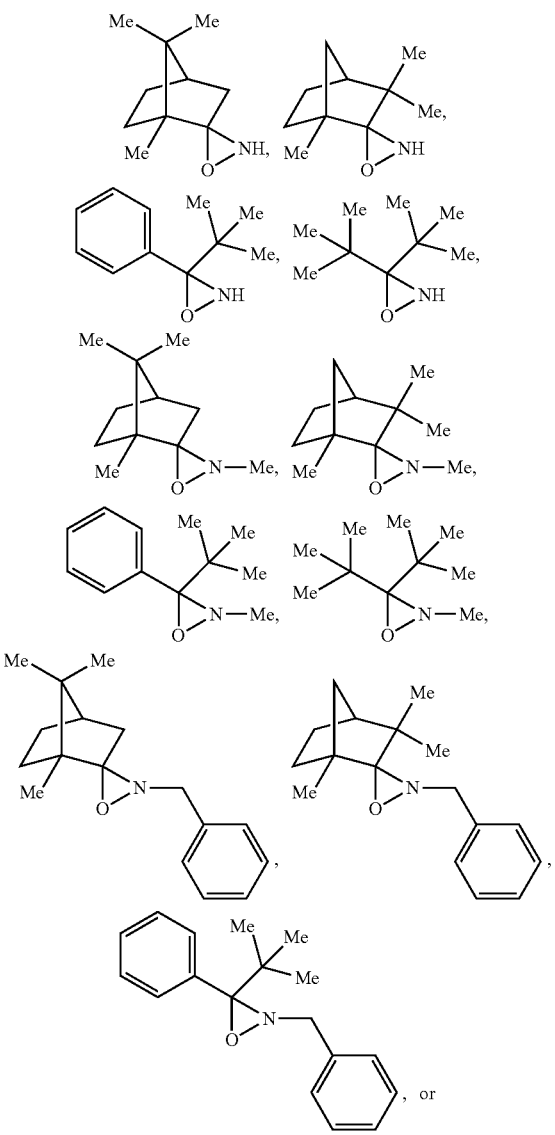

-continued

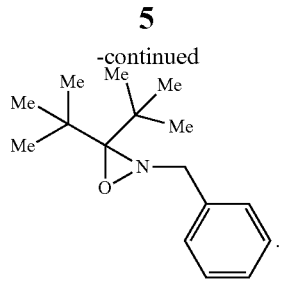

In some embodiments, the weak acid is an acid with a $pK_a$ of less than 12. The weak acid may be an acid addition salt of a nitrogenous base such as a salt of hydrochloric acid. In some embodiments, the nitrogenous base is ammonium. In some embodiments, the weak acid is ammonium chloride.

In some embodiments, the reaction mixture comprises an organic solvent such as an $arene_{(C \leq 12)}$ or substituted $arene_{(C \leq 12)}$. In some embodiments, the organic solvent is toluene. In other embodiments, the organic solvent is an $ether_{(C \leq 12)}$ or a substituted $ether_{(C \leq 12)}$. In other embodiments, the organic solvent is a mixture of two or more solvents. In some embodiments, the weak acid is dissolved in water.

In some embodiments, oxaziridine compound is added to the reaction mixture in an amount from about 0.5 equivalent to about 2.5 equivalent relative to the aromatic compound. The amount of oxaziridine may be from about 1.0 equivalent to about 2.0 equivalent. The amount of oxaziridine compound may be about 1.2 equivalent or may be about 1.5 equivalent. In some embodiments, the first reaction mixture is set at a temperature from about −100° C. to about 0° C. The temperature may be about −90° C. to about −10° C. The temperature may be about −78° C., about −45° C., about −30° C., about −25° C., or about −20° C. In some embodiments, the first reaction mixture is set at a temperature from about −10° C. to about 45° C. The temperature may be about 0° C. to about 30° C. The temperature is about 25° C. or is about room temperature.

In some embodiments, the first reaction mixture is reacted for a time period from about 15 minutes to about 8 hours. The time period may be from about 1 hour to about 6 hours. The time period may be about 2 hours, about 3 hours, or about 4 hours. In some embodiments, when the $R_2$ of the oxaziridine compound is a hydrogen, the reaction produces an aminoaromatic compound. The reaction may be run at a temperature from about −100° C. to about 0° C. In other embodiments, when the $R_2$ of the oxaziridine compound is not a hydrogen, the reaction produces a hydroxyaromatic compound. The reaction may be run at a temperature from about −20° C. to about 50° C.

In still yet another aspect, the present disclosure provides methods of preparing an aminoaromatic group comprising:
(A) admixing a metal aromatic compound with an aminating reagent selected from:
 (1) an oxaziridine compound; or
 (2) O-acylated hydroxylamine compound;
 in presence of a copper reagent to form a first reaction mixture under conditions sufficient to cause a reaction to obtain an anionic intermediate;
(B) admixing a weak acid with the anionic intermediate and the first reaction mixture to obtain a second reaction mixture under conditions sufficient to obtain an aminoaromatic group.

In some embodiments, the metal of the metal aromatic compound is attached to one of the carbon atoms of the aromatic ring. In some embodiments, the metal of the metal aromatic compound is a magnesium halide, lithium, or zinc halide.

In some embodiments, the metal aromatic compound comprises from 1 to 8 aromatic rings. The aromatic rings may be fused. In other embodiments, the aromatic rings are attached in a pendent fashion. In still other embodiments, the aromatic rings are both fused and attached in a pendent fashion.

The metal aromatic compound is not substituted or substituted. In some embodiments, metal aromatic compound is substituted 1, 2, 3, 4, or 5 times and may be substituted with a substituent wherein the substituent is amino, aminosulfonyl, carboxy, cyano, halo, hydroxy, hydroxyamino, hydroxysulfonyl, mercapto, nitro, oxo, or thio; or $acyl_{(C \leq 8)}$, $alkoxy_{(C \leq 8)}$, $cycloalkoxy_{(C \leq 8)}$, $alkenyloxy_{(C \leq 8)}$, $aryloxy_{(C \leq 8)}$, $aralkoxy_{(C \leq 8)}$, $acyloxy_{(C \leq 8)}$, $cycloalkylalkoxy_{(C \leq 8)}$, $heterocycloalkylalkoxy_{(C \leq 8)}$, $heterocycloalkoxy_{(C \leq 8)}$, $alkylthio_{(C \leq 8)}$, $cycloalkylthio_{(C \leq 8)}$, $amido_{(C \leq 8)}$, $alkylamino_{(C \leq 8)}$, $dialkylamino_{(C \leq 8)}$, $alkylsulfonyl_{(C \leq 8)}$, $arylsulfonyl_{(C \leq 8)}$, or a substituted version of these groups, or a protected amine group, a protected hydroxyl group, or a protected thiol group. In one embodiment, the metal aromatic compound is substituted with a substituent wherein the substituent is aminosulfonyl, cyano, halo, nitro, or oxo; or $acyl_{(C \leq 8)}$, $alkoxy_{(C \leq 8)}$, $cycloalkoxy_{(C \leq 8)}$, $alkenyloxy_{(C \leq 8)}$, $aryloxy_{(C \leq 8)}$, $aralkoxy_{(C \leq 8)}$, $cycloalkylalkoxy_{(C \leq 8)}$, $heterocycloalkoxy_{(C \leq 8)}$, $heterocycloalkoxy_{(C \leq 8)}$, $alkylthio_{(C \leq 8)}$, $cycloalkylthio_{(C \leq 8)}$, $amido_{(C \leq 8)}$, $alkylsulfonyl_{(C \leq 8)}$, $arylsulfonyl_{(C \leq 8)}$, or a substituted version of these groups, or a protected amine group, a protected hydroxyl group, or a protected thiol group. In some embodiments, the metal aromatic compound is substituted with a substituent, wherein the substituent is 1, 2, 3, 4, or 5 fused $heteroaryl_{(C \leq 12)}$ rings or fused $heterocycloalkyl_{(C \leq 12)}$ rings, wherein these rings are unsubstituted or substituted.

In some embodiments, the metal aromatic compound comprises from 6 carbon atoms to 30 carbon atoms. The metal aromatic compound may be comprised from 6 carbon atoms to 18 carbon atoms. In some embodiments, the metal aromatic compound comprises from 6 carbon atoms to 12 carbon atoms.

In other aspects, the oxaziridine compound is a compound of the formula:

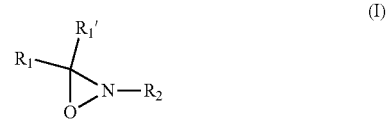

(I)

wherein:
$R_1$ and $R_1'$ are each independently $alkyl_{(C \leq 12)}$, $cycloalkyl_{(C \leq 12)}$, $aryl_{(C \leq 12)}$, or a substituted version of any of these groups, or $R_1$ and $R_1'$ are taken together and are a $cycloalkanediyl_{(C \leq 18)}$ or substituted $cycloalkanediyl_{(C \leq 18)}$; and
$R_2$ is hydrogen or $alkyl_{(C \leq 12)}$, $aryl_{(C \leq 12)}$, $aralkyl_{(C \leq 12)}$, or a substituted version of any of these three groups.

In some embodiments, $R_1$ and $R_1'$ are taken together and a $cycloalkanediyl_{(C \leq 18)}$ or a substituted $cycloalkanediyl_{(C \leq 18)}$. The $cycloalkanediyl_{(C \leq 18)}$ or substituted $cycloalkanediyl_{(C \leq 18)}$ may be a $bicycloalkanediyl_{(C \leq 18)}$ or substituted $bicycloalkanediyl_{(C \leq 18)}$. The $bicycloalkanediyl_{(C \leq 18)}$ or substituted $bicycloalkanediyl_{(C \leq 18)}$ may contain one or more carbon atoms adjacent to the carbon atom of the oxaziridine ring is a quaternary substituted carbon atom. In some embodiments, one of the adjacent carbon atoms is a quaternary substituted carbon atom. In other embodiments, both of the adjacent carbon atoms is a quaternary substituted carbon atom. $R_2$ may be hydrogen. $R_2$ may be alkyl$_{(C\leq 8)}$ such as methyl. $R_2$ may be aralkyl$_{(C\leq 8)}$ such as benzyl. In some embodiments, the oxazridine compound is further defined as:

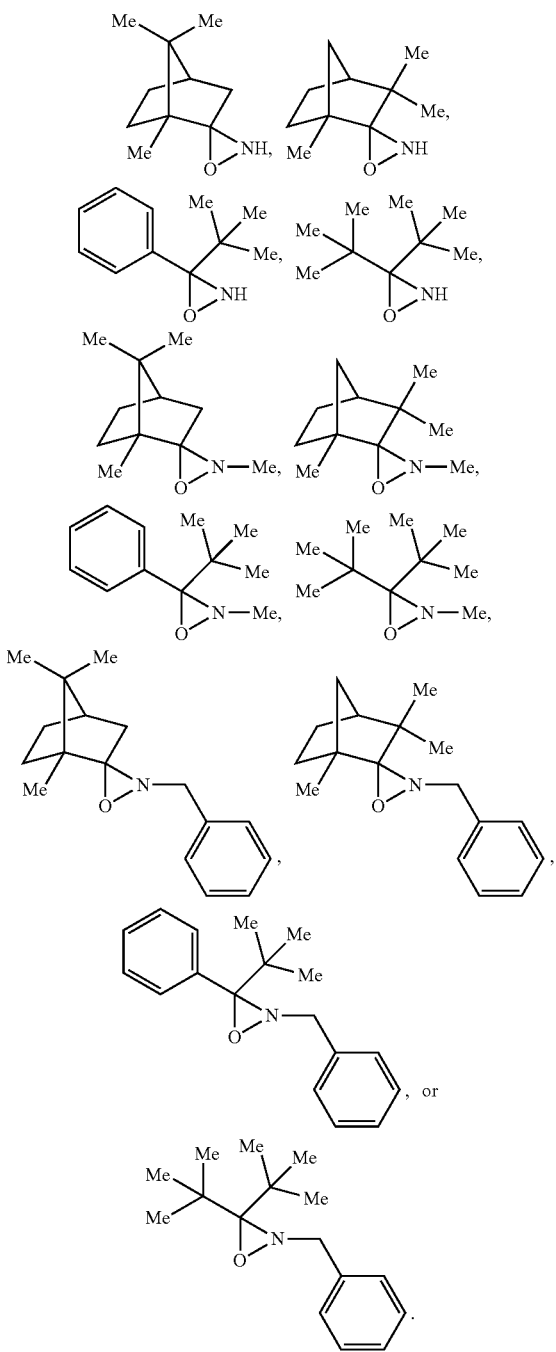

In other embodiments, the aminating reagent is an O-acylated hydroxylamine compound such as a compound of the formula:

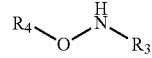

(II)

wherein:
$R_3$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, heterocycloalkyl$_{(C\leq 12)}$, or a substituted version of any of these groups
$R_4$ is acyl$_{(C\leq 18)}$ or substituted acyl$_{(C\leq 18)}$;
or a salt thereof.

In some embodiments, $R_3$ is hydrogen. In other embodiments, $R_3$ is cycloalkyl$_{(C\leq 12)}$ or substituted cycloalkyl$_{(C\leq 12)}$. In still other embodiments, $R_3$ is alkyl$_{(C\leq 12)}$, aralkyl$_{(C\leq 12)}$, or a substituted version of either group. In some embodiments, $R_4$ is further defined as:

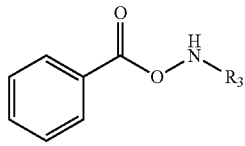

(III)

wherein:
$R_3$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, heterocycloalkyl$_{(C\leq 12)}$, or a substituted version of any of these groups
or a salt thereof.

In some embodiments, the weak acid is an acid with a $pK_a$ of less than 12. The weak acid may be an acid addition salt of a nitrogenous base such as a salt of hydrochloric acid. In some embodiments, the nitrogenous base is ammonium. In some embodiments, the weak acid is ammonium chloride.

In some embodiments, the reaction mixture comprises an organic solvent such as an arene$_{(C\leq 12)}$ or substituted arene$_{(C\leq 12)}$. In some embodiments, the organic solvent is toluene. In other embodiments, the organic solvent is an ether$_{(C\leq 12)}$ or a substituted ether$_{(C\leq 12)}$. In other embodiments, the organic solvent is a mixture of two or more solvents. In some embodiments, the weak acid is dissolved in water.

In some embodiments, oxaziridine compound is added to the reaction mixture in an amount from about 0.5 equivalent to about 2.5 equivalent relative to the aromatic compound. The amount of oxaziridine may be from about 1.0 equivalent to about 2.0 equivalent. The amount of oxaziridine compound may be about 1.2 equivalent or may be about 1.5 equivalent. In some embodiments, the O-acylated hydroxylamine compound is added to the reaction mixture in an amount from about 0.5 equivalent to about 2.5 equivalent relative to the aromatic compound such as from about 1.0 equivalent to about 2.0 equivalent. In some embodiments, the amount of O-acylated hydroxylamine compound is about 1.2 equivalent. In some embodiments, the first reaction mixture is set at a temperature from about −100° C. to about 0° C. The temperature may be about −90° C. to about −10° C. The temperature may be about −78° C. In some embodiments, the first reaction mixture is set at a temperature from about −10° C. to about 45° C. The temperature may be about 0° C. to about 30° C. The temperature is about 25° C. or is about room temperature.

In some embodiments, the first reaction mixture is reacted for a time period from about 15 minutes to about 8 hours. The time period may be from about 1 hour to about 6 hours. The time period may be about 2 hours, about 3 hours, or about 4 hours.

In some embodiments, the copper reagent is a Cu(I) salt. The copper reagent may be a copper halide or a copper cyanide salt. In some embodiments, the copper reagent is CuCN, CuCl, or $[Cu(OTf)]_2 \cdot C_6H_6$. In some embodiments, the copper reagent is a copper salt and an second salt. The copper salt may be CuCN or CuCl. In some embodiments, the second salt is a lithium salt such as lithium chloride. In some embodiments, the copper reagent is CuCN.2LiCl or CuCl.2LiCl. In some embodiments, the copper reagent is added to the reaction mixture in an amount from about 0.05 equivalents to about 5 equivalents of the copper reagent relative to the aromatic compound.

In some embodiments, the amount of the copper reagent is from about 0.1 equivalents to about 2.0 equivalents such as about 1.1 equivalents.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIGS. 2A-2D) Two-step procedures for the synthesis of primary arylamines (4) from the corresponding arylmetals (2 & 2c) using electrophilic aminating agents (1, 5 & 7). (FIG. 2D) Conversion of arylmagnesium halides (2a) to phenols (12) using molecular oxygen in a flow system. (FIG. 2E) A sterically bulky secondary amine (13) does not undergo deprotonation even by n-butyllithium at elevated temperatures. (FIGS. 2F & 2G) Camphor- and fenchone-derived N—H oxaziridines (16 & 18) react with 2-naphthylmagnesium bromide (15) directly at low temperature and under protective Argon atmosphere to afford 2-naphthylamine (17) upon simple aqueous workup. (FIG. 2H) Camphor-derived N-Me oxaziridine (19a) reacts with 15 directly to give 2-napthol (20) upon workup.

FIG. 7C Trapping experiments conducted with either with simultaneous addition of benzaldehyde and aminating agent or benzaldehyde added 5 seconds and 2 hours after the aminating agent.

DESCRIPTION OF ILLUSTRATIVE EMBODIMENTS

Figure 1:
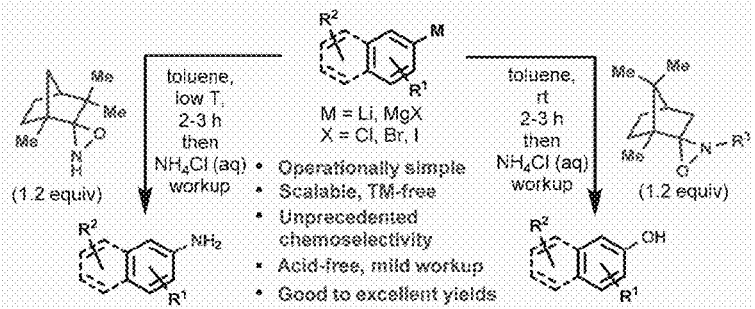
FIG. 1 shows the direct synthesis of anilines and phenols from arylmetals. The low temperature, direct, one-step preparation of primary arylamines and phenols from structurally diverse aryllithiums and arylmagnesium halides is now possible using bench stable N—H and N-alkyl oxaziridines, respectively.

In some aspects, the present disclosure provides methods of preparing aromatic compounds which have been functionalized with an amine group or a hydroxy group using an oxaziridine compound in the presence of a metal aromatic compound. In some embodiments, the use of an oxaziridine compound with a hydrogen atom on the nitrogen atom (secondary amine) results in the production of an amino-aromatic compound. In other embodiments, the use of an oxaridine compound with an aliphatic or aromatic group on the nitrogen atom (tertiary amine) results in the formation of the hydroxyaromatic compound. In some embodiments, the methods described herein may result in higher yield, use milder conditions, resist the chemical degradation of one or more other functional groups on the molecule, or not require the use of a transition metal catalyst.

I. AROMATIC COMPOUNDS

In one aspect, the present methods relating to reacting an aromatic compound. In some embodiments, the aromatic compound is a metal aromatic compound. A metal aromatic compound is a compound containing one or more aromatic ring which has a metal carbon bond. As used herein, an aromatic compound is any compound containing one aromatic ring containing 4n+2 electrons in a ring in which each atom of the ring is sp² hybridized and the ring is planar. The aromatic compound may also further comprise one or more aliphatic or aromatic compounds which may be attached in a pendant fashion or may be fused to the aromatic ring. The aromatic compound may contain from 1 aromatic ring to 8 aromatic rings. The aromatic compound may further comprise from 1 additional aliphatic or aromatic group to 10 additional aliphatic or aromatic groups. These groups include alkyl group, a cycloalkyl group, an alkenyl group, an alkynyl group, aryl, heteroaryl, heterocycloalkyl, or a substituted version of any of these groups wherein the group consists of less than 12 carbon atoms. In some embodiments, the aromatic compound is substituted with another non carbon group such as amino, aminosulfonyl, carboxy, cyano, halo, hydroxy, hydroxyamino, hydroxysulfonyl, mercapto, nitro, oxo, or thio; or acyl$_{(C\leq8)}$, alkoxy$_{(C\leq8)}$, cycloalkoxy$_{(C\leq8)}$, alkenyloxy$_{(C\leq8)}$, aryloxy$_{(C\leq8)}$, aralkoxy$_{(C\leq8)}$, acyloxy$_{(C\leq8)}$, cycloalkylalkoxy$_{(C\leq8)}$, heterocycloalkylalkoxy$_{(C\leq8)}$, heterocycloalkoxy$_{(C\leq8)}$, alkylthio$_{(C\leq8)}$, cycloalkylthio$_{(C\leq8)}$, amido$_{(C\leq8)}$, alkylamino$_{(C\leq8)}$, dialkylamino$_{(C\leq8)}$, alkylsulfonyl$_{(C\leq8)}$, arylsulfonyl$_{(C\leq8)}$, or a substituted version of these groups, or a protected amine group, a protected hydroxyl group, or a protected thiol group. The aromatic compound may be substituted 1, 2, 3, 4, 5, 6, 7, 8, 9, or 10 times with these groups. In some embodiments, the aromatic compound has from 6 carbon atoms to 100 carbon atoms, from 6 carbon atoms to 50 carbon atoms, from 6 carbon atoms to 30 carbon atoms, or from 6, 7, 8, 9, 10, 11, 12, 13, 14, 15, 16, 17, 18, 19, 20, 21, 22, 23, 24, 25, 26, 27, 28, 29, or 30 carbon atoms, or any range derivable therein.

In some embodiments, the metal of the metal aromatic compound is a metal of Group 1 or Group 2 and may be further substituted with one or more monovalent anions such as a halide. The metal may be a magnesium halide or lithium. In other aspects, the methods result in the preparation of an aminoaromatic group. As described herein, an aminoaromatic group is an aromatic compound containing at least one nitrogen carbon bond at the location of the previous metal carbon bond. In some embodiments, the nitrogen atom of the nitrogen carbon bond further comprises two hydrogen, aliphatic or aromatic groups. These aliphatic or aromatic groups may contain less than 12 carbon atoms each. Similarly, hydroxyaromatic group contains an oxygen carbon bond instead of a nitrogen carbon bond and the oxygen atom may further comprise a hydrogen atom or an aliphatic or aromatic group.

In some aspects, the present methods produce an anionic intermediate which may be protonated to obtain the desired aminoaromatic group and hydroxyaromatic group. In some embodiments, the anionic intermediate is a negatively charged amine group. In other embodiments, the anionic intermediate is a negatively charged hydroxy group.

II. OXAZIRIDINE COMPOUNDS

In some aspects, the present methods describe the use of an oxaziridine compound as a reaction component in the instant methods. The oxaziridine compound consist of a compound with at least one three membered ring containing one carbon atom, one nitrogen atom, and one oxygen atom. In some aspects, the oxaziridine compound contains two alkyl groups attached to the carbon atom. The carbon atom of the oxaziridine compound may be taken together through a C1-C12 alkanediyl or cycloalkanediyl. In other embodiments, the carbon atom is attached to two other aliphatic or aromatic groups such as an alkyl group, a cycloalkyl group, an alkenyl group, an alkynyl group, an aryl group, or an aralkyl group wherein each one of these groups contains 18 or less carbon atoms. In some embodiments, the groups contain 12 or fewer carbon atoms. These groups may be optional substituted as that term is defined herein. Furthermore, one or more of the carbon atoms adjacent to the carbon atom of the oxaziridine group is a quartnary carbon atom. In some embodiments, the carbon atom is substituted with one or more aliphatic groups such as an alkyl group, a cycloalkyl group, an alkenyl group, an alkynyl group, or a substituted version of any of these groups. In some embodiments, the quartnary carbon atom is substituted with alkyl or cycloalkyl groups containing 8 or fewer carbon atoms. In some embodiments, both of the adjacent carbon atoms may be substituted with an alkyl group such as a methyl, ethyl, isopropyl, or t-butyl group. In another aspect, the nitrogen atom of the oxaziridine group is joined to a hydrogen atom. In other aspects, the nitrogen atom is substituted with one or more aliphatic or aromatic group containing 12 or fewer carbon atoms such as methyl or benzyl group. Some non-limiting examples of an oxaziridine compound include those of the formula:

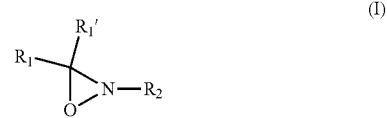

wherein:

R$_1$ and R$_1$' are each independently alkyl$_{(C\leq12)}$, cycloalkyl$_{(C\leq12)}$, aryl$_{(C\leq12)}$, or a substituted version of any of these groups, or R$_1$ and R$_1$' are taken together and are a cycloalkanediyl$_{(C\leq18)}$ or substituted cycloalkanediyl$_{(C\leq18)}$; and R$_2$ is hydrogen or alkyl$_{(C\leq12)}$, aryl$_{(C\leq12)}$, aralkyl$_{(C\leq12)}$, or a substituted version of any of these three groups.

Additional examples include:

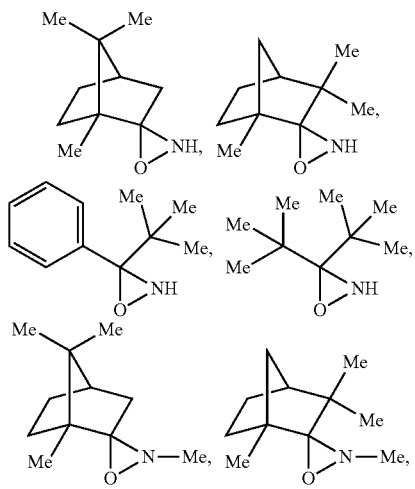

-continued

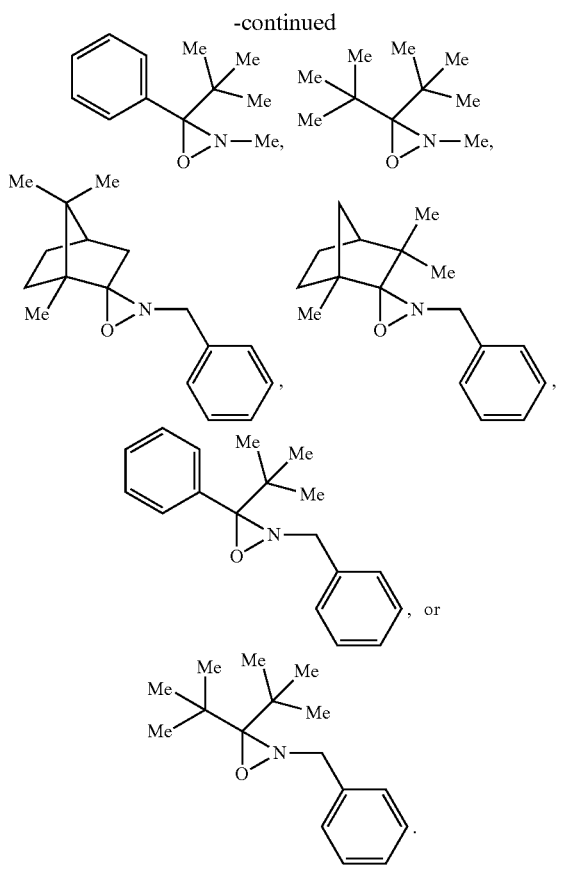

In some embodiments, the methods described herein include using from about 0.1 to about 10 equivalents of the oxaziridine compound to the aromatic compound. The amount of the oxaziridine compound may be from about 0.5 to about 5 equivalents or from 0.5, 0.6, 0.7, 0.8, 0.9, 1.0, 1.1, 1.2, 1.3, 1.4, 1.5, 1.75, 2.0, 2.25, 2.5, 3, 4, to about 5 equivalents of the oxaziridine compound. In some embodiments, the methods use about 1.2 equivalents of the oxaziridine compound to the aromatic compound. In other embodiments, the methods use about 1.5 equivalents of the oxaziridine compound.

III. REACTION CONDITIONS

In some embodiments, the methods described herein may further comprise adjusting the conditions of a reaction mixture. Some non-limiting examples of such conditions include temperature, the amount of one or more components of the reaction mixture, the organic solvent, or the time period in which the reaction is run. In some embodiments, the temperature of the reaction mixture is a temperature from about −100° C. to about 25° C., from about −85° C. to about 0° C., or from about −80° C. to about −25° C. The temperature of the reaction mixture may be from about −100° C., −95° C., −90° C., −85° C., −80° C., −75° C., −70° C., −65° C., −60° C., −55° C., −50° C., −45° C., −40° C., −35° C., −30° C., −25° C., −20° C., −10° C., 0° C., 10° C., to about 25° C., or any range derivable therein. In some embodiments, the temperature is about −45° C. In other embodiments, the temperature is about −78° C.

In another aspect, the methods described herein may further comprise an organic solvent. Some non-limiting examples of organic solvents which may be used in the presence methods include an ether such as diethyl ether or tetrahydrofuran. In other embodiments, the organic solvent is a polar aprotic solvent such as tetrahydrofuran, ethyl acetate, acetone, dimethylformamide, acetonitrile, or dimethyl sulfoxide. In other embodiments, the methods use a non-polar solvent such as 1,4-dioxane, chloroform, diethyl ether, or dichloromethane. In some embodiments, the methods use a mixture of two or more solvents. In some embodiments, the organic solvent has a dipole moment of greater than 0.5 D.

In another aspect, the methods described herein may further comprise adding from about 0.5 equivalents to about 5 equivalents of the metal aromatic compound. The methods, in some embodiments, comprise from about 0.75 equivalents to about 2.5 equivalents of the metal aromatic compound. In some embodiments, the amount of the metal aromatic compound is from about 0.75 equivalents, 0.8 equivalents, 0.9 equivalents, 1.0 equivalent, 1.1 equivalent, 1.2 equivalents, 1.3 equivalents, 1.4 equivalents, 1.5 equivalents, 1.75 equivalents, or 2.0 equivalents, or any range derivable therein. The amount of the metal aromatic compound is from about 1.0 equivalent to about 1.5 equivalents of the metal aromatic compound. In other aspects, the oxaziridine compound may be added from about 0.5 equivalents to about 5 equivalents. In some embodiments, the amount of the oxaziridine compound is from about 0.75 equivalents to about 2.5 equivalents of the oxaziridine compound. In some embodiments, the amount of the metal aromatic compound is from about 0.75 equivalents, 0.8 equivalents, 0.9 equivalents, 1.0 equivalent, 1.1 equivalent, 1.2 equivalents, 1.3 equivalents, 1.4 equivalents, 1.5 equivalents, 1.6 equivalents, 1.7 equivalents, 1.8 equivalents, 1.9 equivalents, or 2.0 equivalents, or any range derivable therein.

In other aspect, the methods contemplate a reaction which is run for a time period from about 15 minutes to about 24 hours. In some embodiments, the time period is from 30 minutes to about 18 hours or 1 hour to about 12 hours. In some embodiments, the time period is from about 15 minutes, 30 minutes, 45 minutes, 1 hour, 1.5 hours, 2 hours, 2.5 hours, 3 hours, 3.5 hours, 4 hours, 4.5 hours, 5 hours, 6 hours, 8 hours, 10 hours to about 12 hours, or any range derivable therein. In some embodiments, the time period is about 2 hours. In other embodiments, the time period is about 4 hours.

IV. SYNTHETIC METHODS

In some aspects, the compounds of this disclosure can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of the biaryl compounds.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo" means independently —F, —Cl, —Br or —I; "amino" means —NH₂; "hydroxyamino" means —NHOH; "nitro" means —NO₂; imino means =NH; "cyano" means —CN; "isocyanate" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; and "thio" means =S; "hydroxysulfonyl" means —SO₃H, "aminosulfonyl" means —S(O)₂NH₂, "sulfonyl" means —S(O)₂—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the formula

includes

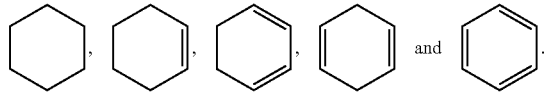

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀⦀⦀" means a single bond where the group attached to the thick end of the wedge is "into the page". The symbol "⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

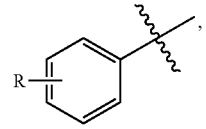

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

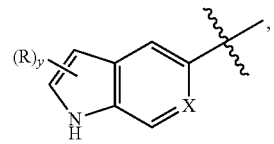

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$-(methylene), —CH$_2$CH$_2$—, —CH$_2$C(CH$_3$)$_2$CH$_2$—, and —CH$_2$CH$_2$CH$_2$—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forms part of one or more non-aromatic ring structures, a cyclo or cyclic structure, no carbon-carbon double or triple bonds, and no atoms other than carbon and hydrogen. Non-limiting examples of cycloalkyl groups include: —CH(CH$_2$)$_2$ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, said carbon atom(s) forms part of one or more non-aromatic ring structures, a cyclo or cyclic structure, no carbon-carbon double or triple bonds, and no atoms other than carbon and hydrogen.

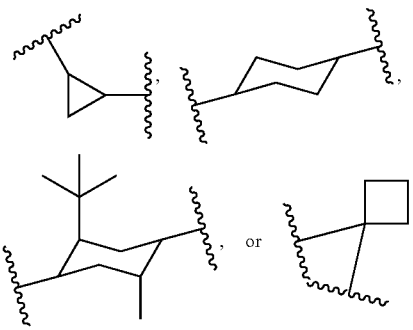

are non-limiting examples of cycloalkanediyl groups. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted cycloalkyl groups: —C(OH)(CH$_2$)$_2$,

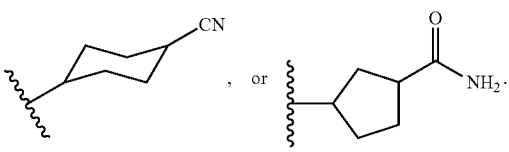 [SMILES: *C1CCC(C#N)CC1 ; *C1CCC(C(N)=O)C1]

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, and —CH=CHCH$_2$—, are non-limiting examples of alkenediyl groups. It is noted that while the alkenediyl group is aliphatic, once connected at both ends, this group is not precluded from forming part of an aromatic structure. The terms "alkene" and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

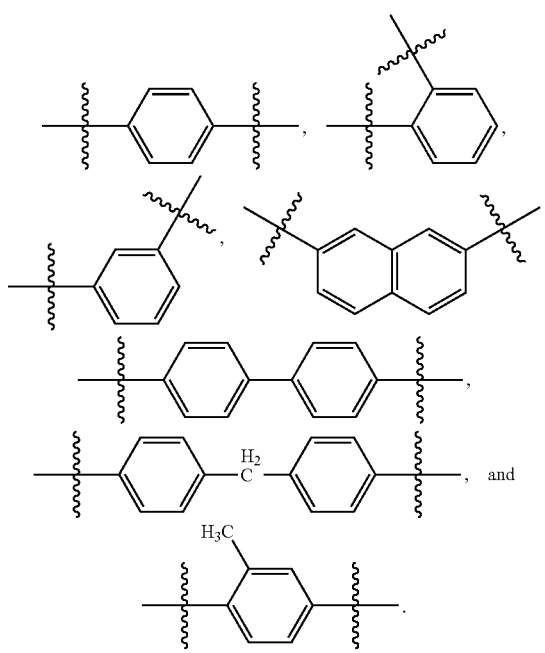

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can each independently be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$.

The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane or cycloalkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "halocarboxylic acid" when used without the "substituted" modifier refers to the group RCO$_2$R', in which R is a haloalkyl and R is hydrogen or alkyl, as those terms is defined above. Non-limiting examples include: trifluoroacetic acid or 2,2,2-trifluoropropionic acid. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth).

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Amination of Arylmetal Compounds

Figures 2A, 2B, 2C, 2D, 2E, 2F, 2G, 2H:
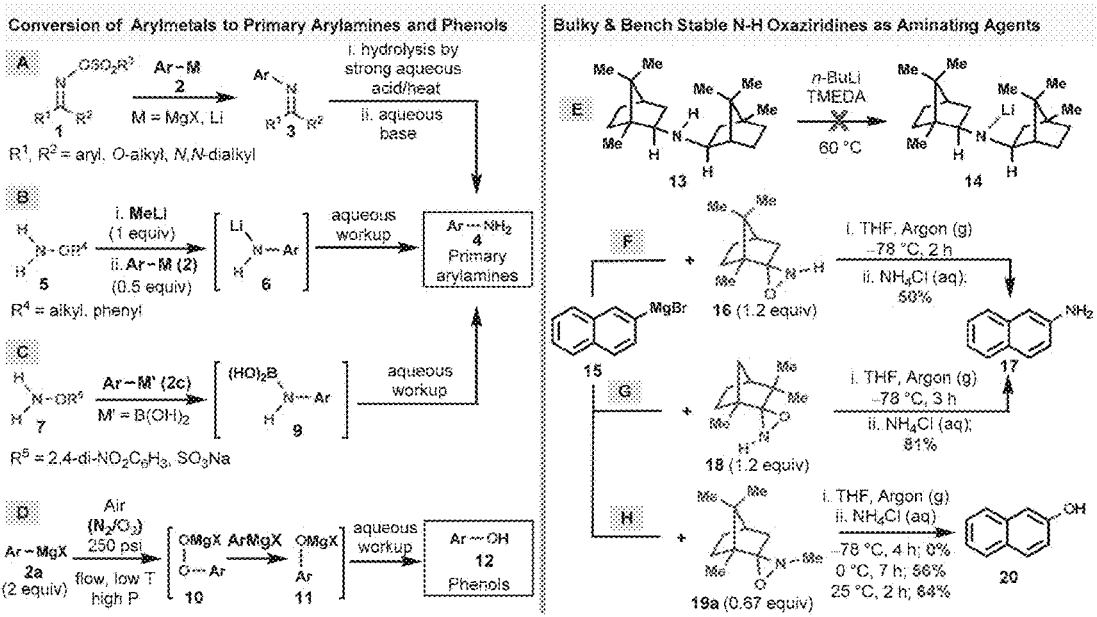
FIGS. 2A-2H shows the primary arylamine and phenol synthesis.

Given that highly sterically hindered secondary amines tend to be resistant to N—H deprotonation (Corey and Gross, 1985), even in the presence of excess alkyllithium reagents at elevated temperatures, (FIG. 2, E), N—H oxaziridines, such as 16 and 18, were tested for their potential to undergo amination moiety with arylmetal reagents faster than the deprotonation of the N—H functionality of the N—H oxaziridines. The camphor-derived N—H oxaziridine 16 was found to be an efficient N—H-transfer agent and reacted smoothly with 2-naphthylmagnesium bromide (15) to afford, after simple aqueous workup, the corresponding 2-naphthylamine (17) directly in its unprotected free-base form (FIG. 2, F). With this reaction method, the use of either a large excess of aminating reagent (16) or arylmetal substrate (15) was not required in order to obtain a synthetically useful isolated yield (50%; 1 mmol scale) in this direct primary amination reaction. The main side product was the protonated aryl-Grignard reagent (naphthalene, 25% isolated yield), suggesting a competing deprotonation of the N—H group. This undesired deprotonation pathway could be suppressed by increasing the steric bulk of the oxaziridine moiety as shown in the reaction of the more sterically hindered fenchone-derived N—H oxaziridine (18) with 2-naphthylmagnesium bromide (15) which furnished 2-naphthylamine (17) in a significantly improved isolated yield (FIG. 2, G). The extent of N—H deprotonation was less than in the case of 18 compared to 16. Both 16 and 18 acted as exclusive N-transfer agents with only trace amounts (<1%) of oxygenated arenes, such as phenols, detected in the resultant products. These oxygenated arenes were likely the result of air oxidation.

Figure 3:
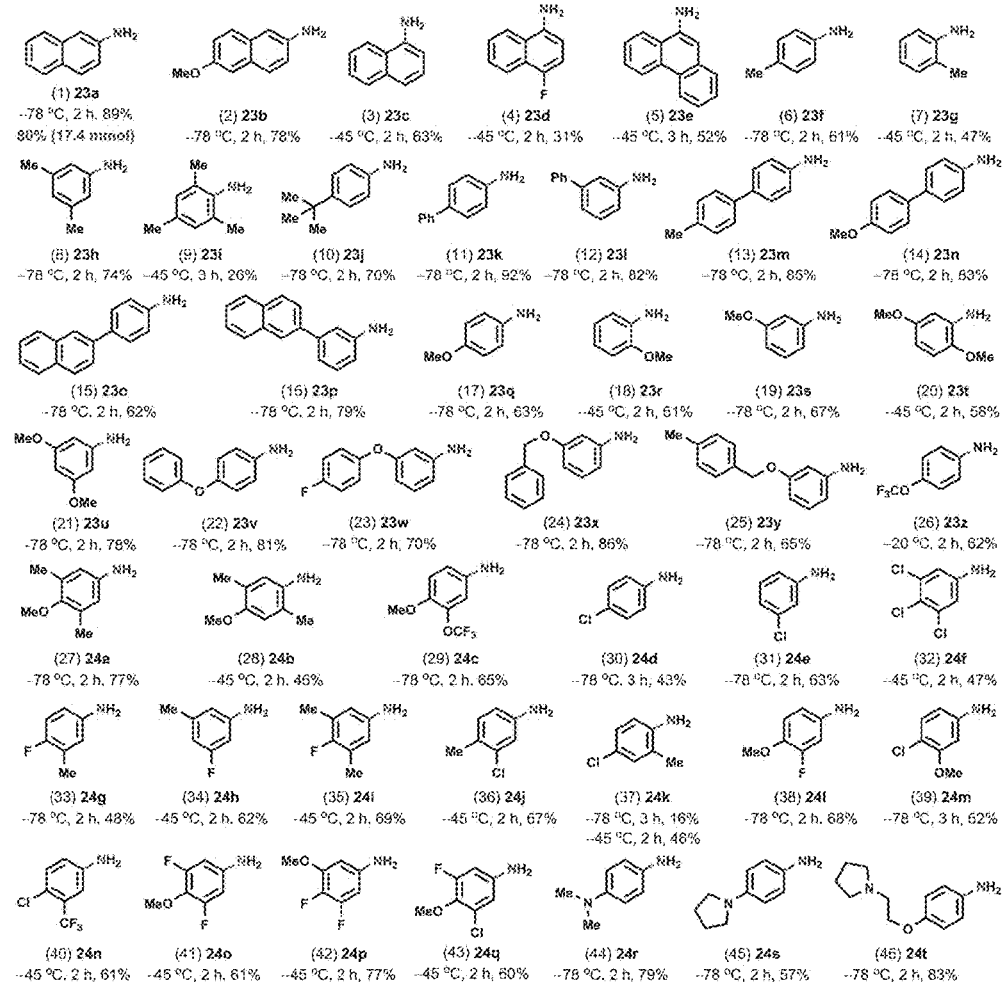
FIG. 3 shows the scope of substrates using fenchone-derived N—H oxaziridine (18) as an efficient primary aminating agent. All aromatic Grignard reagents (21) have been prepared from the corresponding aryl halides using turnings of freshly activated Mg metal and THF as the solvent. The concentration of the arylmetal solution was targeted to be around 0.5 M but was carefully determined by titration immediately before use. The amination reactions were conducted on a 1 mmol scale at the indicated temperature and considered complete upon the full consumption of the aminating agent (18) by TLC analysis; a number of experiments showed that 18 undergoes decomposition in the presence of strong metal bases.
Figure 4:
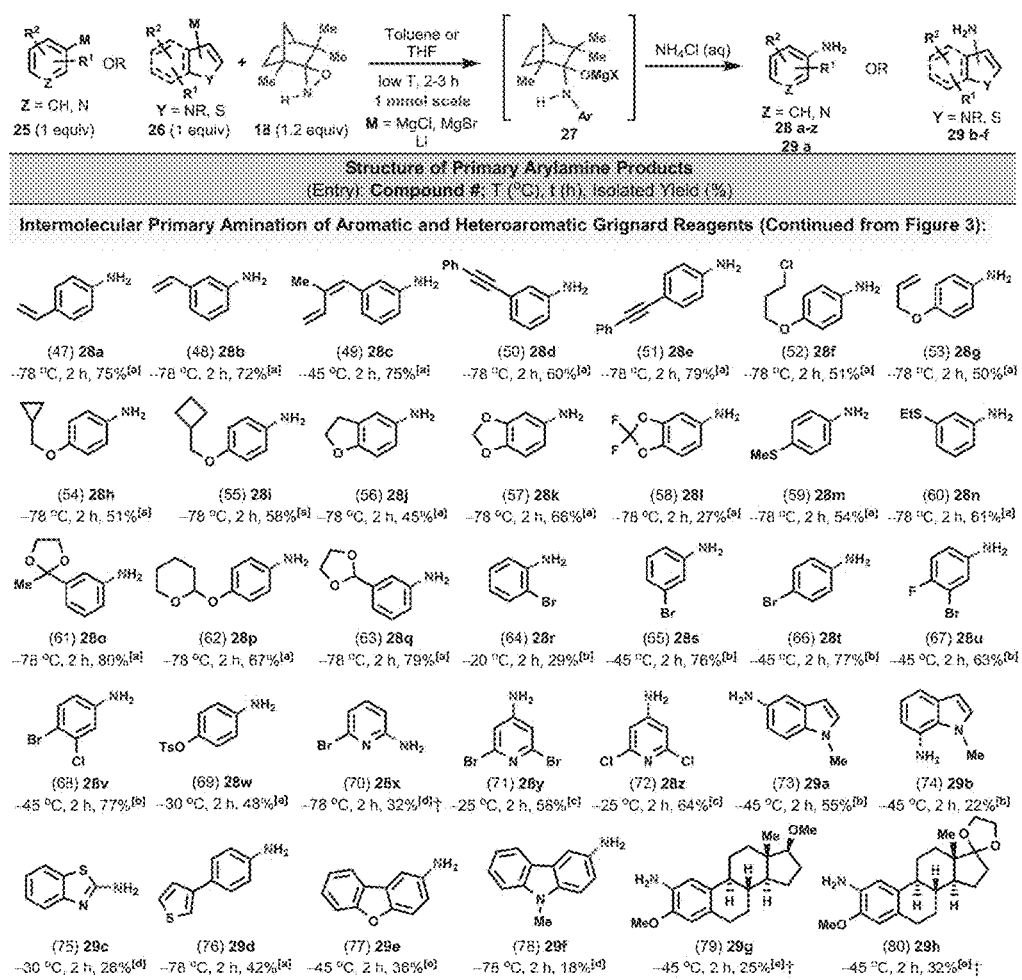
FIG. 4 shows the scope of substrates using fenchone-derived N—H oxaziridine (18) as an efficient primary aminating agent. The aromatic and heteroaromatic metal reagents (25 & 26) have been prepared using one of the following methods: [a] from aryl halides using activated Mg metal; [b] from aryl halides using i-PrMgCl.LiCl complex (Knochel's procedure); [c] direct C—H deprotonation with TMPMgCl.LiCl; [d] performed with the aryllithium reagent via Li/hal exchange and [e] Li/Br exchange followed by transmetallation with $MgBr_2$. †=The primary amination was performed with N—H oxaziridine 30.

Encouraged by these initial results, thorough optimization studies were conducted (See Example 3) which concluded that the highest isolated yields were obtained at a temperature of −78° C. in toluene/THF mixture when using a 1/1.2 ratio of arylmetal and aminating agent (oxaziridine). With the optimum reaction conditions in hand, the scope and limitations of this method was evaluated by subjecting dozens of substituted arylmetal reagents to primary amination (FIGS. 3 & 4). The initially tested forty-six (46) arylmetal reagents represent an extensive sampling of both fused- and monocyclic aromatic rings as well as electron-rich and electron-deficient examples (FIG. 3.). Fused aromatic rings (entries 1-5, FIG. 3) and biaryl systems (entries 11-16) underwent smooth primary amination with good to excellent isolated yields except for one instance (entry 4) in which an electronegative fluorine atom was in the para position of the carbon-magnesium (C—Mg) bond which only showed an isolated yield of 31%. Ring-halogenated substrates (entries 30-43, FIG. 3) furnished the corresponding primary anilines in moderate to good yields and clearly illustrate the true complementary nature of this method to transition metal-catalyzed aminations given that halogens atoms are well-tolerated.

When one or more alkyl substituents are located adjacent to the aryl-metal bond (ortho positions), primary aminations proceed in fair to moderate yields (entries 7, 9, 28 & 37, FIG. 3), however, substrates with o-methoxy substituents (entries 18 & 20, FIG. 3) furnished the primary arylamines in good isolated yields. It is likely that when both the substrate and the aminating agent are sterically bulky, the rate and efficiency of primary amination are reduced—in these cases the elevation of reaction temperature (−45° C. instead of −78° C.) was necessary to observe synthetically useful reaction times and isolated yields (see specifically entry 37, FIG. 3). It is worth pointing out that substrates having tertiary amine moieties (—$NR_2$), that are usually quite sensitive to oxidation, furnished the corresponding primary arylamines in good to excellent yields (entries 44-46, FIG. 3). These cases highlight the remarkable chemoselectivity of aminating agent 18.

In order to further illustrate the unprecedented mildness of this direct primary amination method, thirty-two (32) aromatic and heteroaromatic substrates were selected that have redox- or hydrolytically-sensitive moieties (FIG. 4) such as a primary alkyl halide (entry 52), isolated and conjugated olefins (entries 47, 48 & 53), a 1,3-diene (entry 49), alkynes (entries 50-51), ethers and thioethers (entries 54-60), acetals and ketals (entries 61-63), one or more halogen atoms (entries 64-71) and electron-rich heterocycles (entries 73-77). Most of these functionalities are well-tolerated under the reaction conditions—especially noteworthy is the high isolated yields of anilines featuring either highly acid-sensitive acetal or ketal functionalities (entries 61-63) or oxidatively highly sensitive thioether moieties (entries 59-60). In a few of cases (entries 58, 64, 69, 73, 74 & 77), the isolated yields were poor (e.g., <30%) that can be attributed to a combination of steric and electronic factors or to the volatility of the product (entry 58). This methodology can also be used for the late-stage functionalization of structurally complex and pharmaceutically relevant intermediates (e.g., estradiol derivative 29 g, entry 78).

Figure 5:
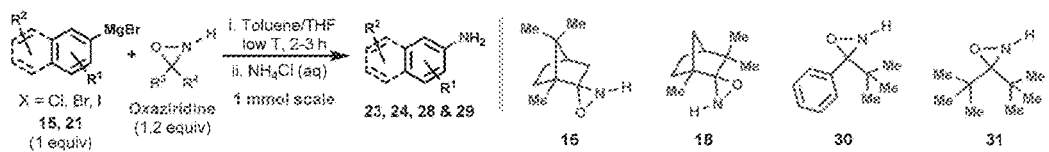
FIG. 5 shows studies noting the improving the efficiency of primary amination for sterically hindered (e.g., ortho-substituted) arylmetals. Four bench stable NH-oxaziridines (16, 18, 30 & 31) were evaluated as aminating agents under the indicated reaction conditions.
Figure 6:
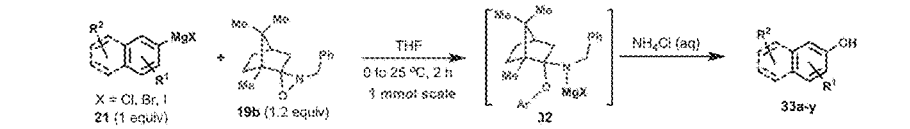
FIG. 6 shows that the N-Benzyl derivative of camphor-derived oxaziridine (19b) serves as an exclusive 0-transfer agent when reacted with arylmetals. Reaction with aryl-Grignard reagents were conducted between 0-25° C. followed by mild workup with aqueous $NH_4Cl$ solution.

Given the reduced primary amination performance of N—H oxaziridine 18 with sterically hindered substrates such as those with substituents in the ortho position, the impact of reducing the steric bulk around the oxaziridine moiety was explored (FIG. 5). To this end, two additional N—H oxaziridines (30 & 31) were prepared that are sterically less hindered than N—H oxaziridines 16 & 18 and were contemplated to improve the isolated yields of primary arylamines for some of the more challenging substrates (Scheme 5). Based upon studying these four N—H oxaziridines, it was found that as the steric bulk of the N—H oxaziridines was reduced, their primary amination performance improved markedly with sterically hindered arylmetals. In contrast, the primary amination of sterically unencumbered arylmetals (e.g., 15→23a) became less efficient with the decreasing steric bulk of the N—H oxaziridines. The tentative order of bulkiness for the N—H oxaziridine 18>30>16>31, and the change in activity may be presumably due to easier N—H deprotonation. It appears that N—H oxaziridine 18 can efficiently transfer the primary amino group (—NH$_2$) to most arylmetals as long as the arylmetals do not have ortho substituents and there are not many electron-withdrawing substituents on the aromatic rings to diminish the nucleophilicity/reactivity of the carbon-metal bond. From the results in FIG. 5 indicate that one can readily find a suitable and sufficiently reactive N—H oxaziridine aminating agent for both sterically demanding and less nucleophilic arylmetals. Without wishing to be bound by any theory, it is believed that the proposed mechanistic pathway is shown in FIG. 6.

Example 2—Oxygen Substituted Arylmetals

The direct N-alkyl-transfer, a highly coveted transformation, was also a possibility by utilizing the N-alkyl versions of oxaziridines 16 and 18. Unfortunately, the N-Me oxaziridine 19a (the N-Me analogue of 16) did not react at all with 2-naphthylmagnesium bromide (15) at −78° C. However, at 0-25° C., the N-Me oxaziridine acted as an effective O-transfer agent and converted 15 to the corresponding phenol 20 in good isolated yield (FIG. 2, H). Analysis of the reaction mixture revealed that the oxygen transfer was exclusive and none of the N-transfer product could be detected by LC-MS analysis. A control experiment under argon atmosphere, and in the absence of 19, led to the formation of only trace amounts of 20, indicating that the origin of oxygen atom in phenol 20 is the oxaziridine (19) and not the adventitious oxygen (02) from air.

Figures 7A, 7B, 7C:
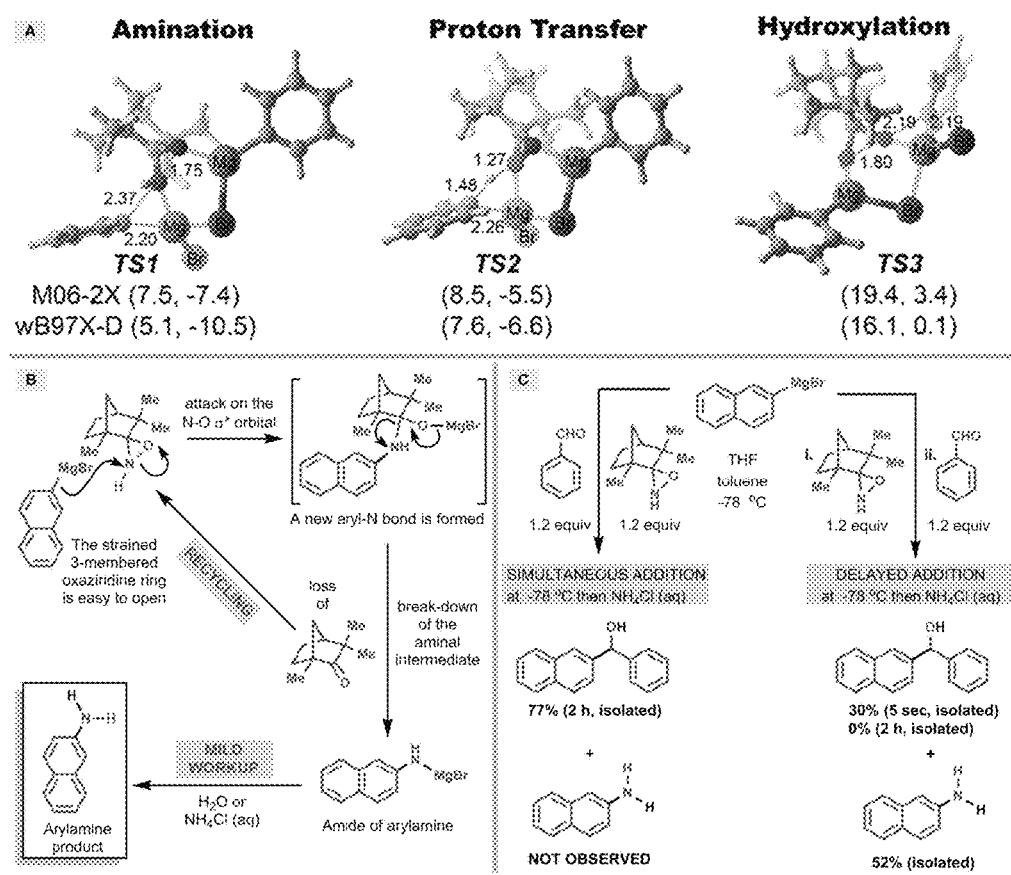
FIGS. 7A-7C show the FIG. 7A 3D representation of competitive amination and proton-transfer transition states. Free energy barriers, enthalpy barriers in kcal/mol. (Top row numbers correspond to M06-2X with the bottom row to wB97X-D.) FIG. 7B Proposed mechanism of the direct primary amination of aryl-metals using bench-stable NH-oxaziridines.

For the direct hydroxylation of arylmetals, several N-alkyl oxaziridines have been prepared and evaluated. N-Benzyl oxaziridine 19b was selected for further testing as the initial hydroxylation reagent given its ease of synthesis, bench stability and chemoselectivity. The examples in FIG. 7 are sufficient to illustrate the functional group tolerance of this reagent as both oxidatively (entries 9, 17, 19, 20, 21 & 24) and hydrolytically (entries 22 & 23) sensitive functionalities remained untouched during the amination and hydroxylation processes. It is worth pointing out that phenols themselves are usually highly oxidatively sensitive even without additional electron-donating groups on their aromatic rings—the fact that most of the hydroxyarene products were isolated in good yield attests to the mildness of this method.

Example 3—Reaction Condition Optimization

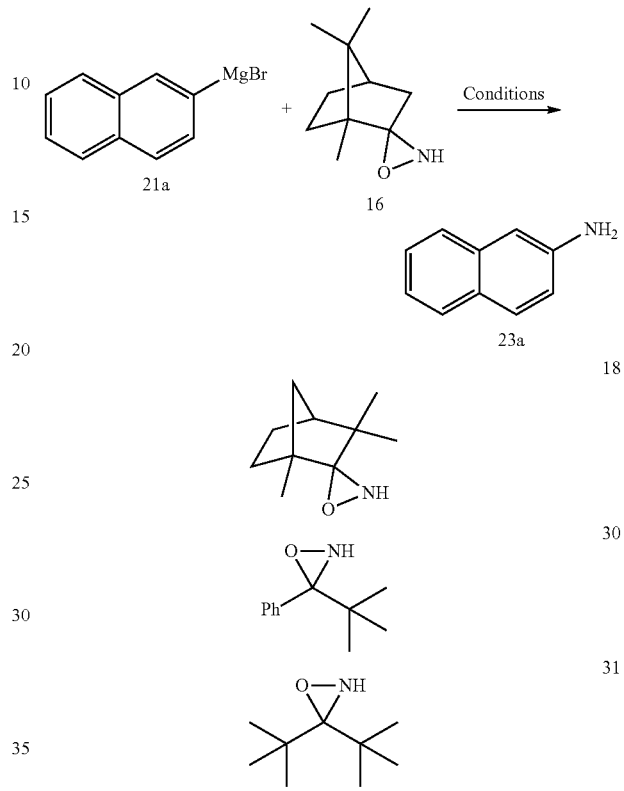

TABLE 1

Reaction Condition Optimization for Amination Reaction

| Entry | Equiv of 21a | Equiv of NH | Additives 1.2 equiv | Solvent | Temperature | Time | Yield of 23a |
|---|---|---|---|---|---|---|---|
| 1 | 2.0 | 16, 1.0 | — | THF | −45° C. | 1 h | 59% |
| 2 | 2.0 | 16, 1.0 | — | THF | −78° C. | 5 h | 58% |
| 3 | 2.0 | 16, 1.0 | — | THF | −78° C. | 1 h | 43% |
| 4 | 2.0 | 16, 1.0 | — | THF | 0° C. | 1 h | 25% |
| 5 | 1.5 | 16, 1.0 | — | THF | −45° C. | 1 h | 54% |
| 6 | 1.0 | 16, 1.5 | — | THF | −45° C. | 1 h | 65% |
| 7 | 1.0 | 16, 1.5 | — | THF | −45° C. | 2 h | 57% |
| 8 | 1.0 | 16, 1.2 | — | THF | −78° C. | 2 h | 50% |
| 9 | 1.0 | 16, 1.2 | — | THF | −45° C. | 2 h | 63% |
| 10 | 1.0 | 16, 1.2 | TMEDA | THF | −45° C. | 2 h | 42% |
| 11 | 1.0 | 16, 1.2 | DMPU | THF | −45° C. | 2 h | 45% |
| 12 | 1.0 | 16, 1.2 | HMPA | THF | −45° C. | 2 h | 46% |
| 13 | 1.0 | 16, 1.5 | — | Et$_2$O | −45° C. | 2 h | 43% |
| 14 | 1.0 | 16, 1.5 | — | Toluene | −45° C. | 2 h | 41% |
| 15 | 1.0 | 16, 1.5 | — | CH$_2$Cl$_2$ | −45° C. | 2 h | 33% |
| 16 | 1.0 | 18, 1.2 | — | THF | −45° C. | 2 h | 77% |
| 17 | 1.0 | 18, 1.2 | — | THF | −78° C. | 2 h | 81% |
| 18 | 1.0 | 18, 1.2 | — | THF | −0° C. | 2 h | 68% |
| 19 | 1.0 | 18, 1.5 | — | THF | −45° C. | 2 h | 69% |
| 20 | 1.0 | 18, 1.5 | — | THF | −78° C. | 2 h | 68% |
| 21 | 1.0 | 18, 1.2 | — | Et$_2$O | −78° C. | 2 h | 76% |
| 22 | 1.0 | 18, 1.2 | — | Toluene | −78° C. | 2 h | 89% |
| 23 | 1.0 | 18, 1.2 | — | CH$_2$Cl$_2$ | −78° C. | 2 h | 83% |
| 24 | 1.0 | 30, 1.2 | — | Toluene | −78° C. | 2 h | 83% |
| 25 | 1.0 | 31, 1.2 | — | Toluene | −78° C. | 2 h | 46% |

TABLE 2

Optimization of the Hydroxylation Reaction Conditions

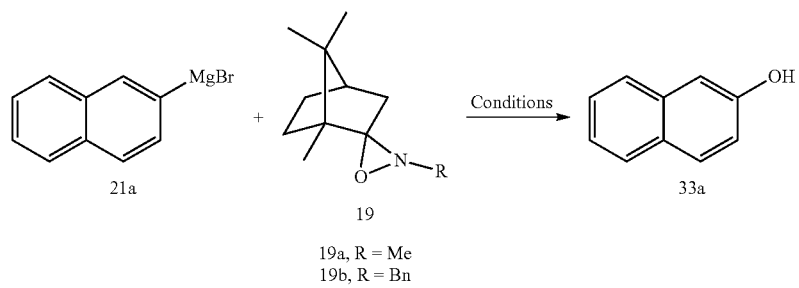

19a, R = Me
19b, R = Bn

| Entry | Equiv of 21a | Equiv of 19 | Solvent | Temperature | Time | Yield of 3a |
|---|---|---|---|---|---|---|
| 1 | 1.5 | 19a, 1.0 | THF | −78° C. | 4 h | N.R. |
| 2 | 1.5 | 19a, 1.0 | THF | 0° C. | 7 h | 56% |
| 3 | 1.5 | 19a, 1.0 | THF | r.t. | 7 h | 78% |
| 4 | 1.0 | — | THF | r.t. | 7 h | <5% |
| 5 | 1.0 | — | THF | r.t. (Air) | 7 h | 32% |
| 6 | 1.5 | 19a, 1.0 | THF | r.t. | 2 h | 64% |
| 7 | 1.0 | 19a, 1.5 | THF | r.t. | 2 h | 83% |
| 8 | 1.0 | 19a, 1.5 | THF | r.t. (Air) | 2 h | 84% |
| 9 | 1.0 | 19a, 1.5 | THF | r.t. | 2 h | 78% |
| 10 | 1.0 | 19a, 1.2 | THF | r.t. | 2 h | 71% |
| 11 | 1.0 | 19b, 1.5 | THF | r.t. | 2 h | 86% |
| 12 | 1.0 | 19b, 1.2 | THF | r.t. | 2 h | 77% |
| 13 | 1.0 | 19b, 1.5 | DCM | r.t. | 2 h | 75% |
| 14 | 1.0 | 19b, 1.5 | Et$_2$O | r.t. | 2 h | 79% |
| 15 | 1.0 | 19b, 1.5 | Toluene | r.t. | 2 h | 85% |

Example 4—Compound Characterization

Solvents were dried by passage through an activated alumina column under argon. Liquids and solutions were transferred via syringe. All halogen-substituted arene reagents were purchased from Sigma-Aldrich Co. and used without further purification. All reactions were carried out in flame-dried glassware under an atmosphere of argon with magnetic stirring. All Grignard reagents were freshly prepared and the concentration of the Grignard reagents was titrated by literature reported method (Love and Jones, 2009). All reactions were monitored by thin-layer chromatography (TLC) with E. Merck silica gel 60 F254 pre-coated plates (0.25 mm). Silica gel (particle size 0.032-0.063 mm) purchased from SiliCycle was used for flash chromatography.

Proton ($^1$H) and carbon ($^{13}$C) NMR spectra were recorded on a Bruker AV-400 or a Bruker DRX-600 spectrometer operating at 400 MHz (or 600 MHz) for proton and 100 MHz (or 151 MHz) for carbon nuclei using CDCl$_3$ as solvent, respectively. Chemical shifts are expressed as parts per million (δ, ppm) and are referenced to 7.26 (CDCl$_3$) for $^1$H NMR and 77.00 (CDCl$_3$) for $^{13}$C NMR. Proton signal data uses the following abbreviations: s=singlet, d=doublet, t=triplet, q=quartet, m=multiplet, br=broad and J=coupling constant. High Resolution Mass Spectrometry was performed on a Shimadzu LCMS-IT-TOF under the conditions of electrospray ionization (ESI) in both positive and negative mode.

A. Synthesis of Oxaziridines

Synthesis of Camphoryl N—H Oxaziridine 16 [Adapted from Literature Procedure (Page, et al., 2000)]

Scheme 1- Synthesis of Camphoryl N—H Oxaziridine 16

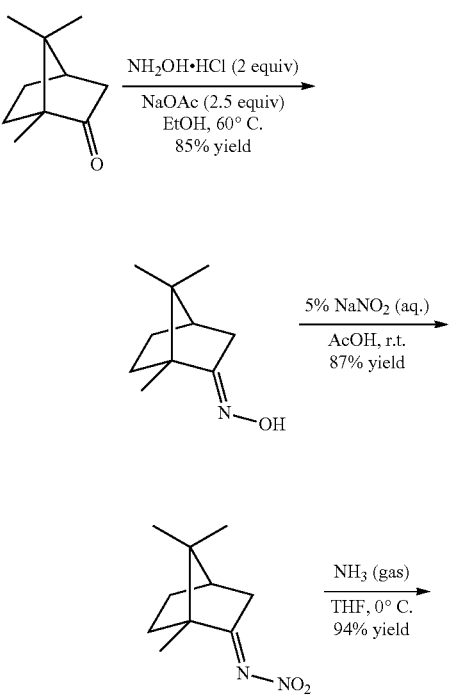

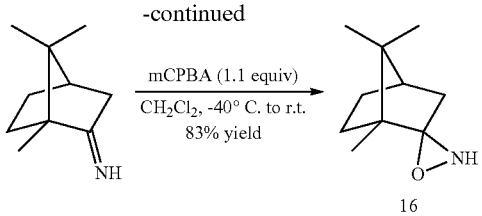

(±)-Camphor Oxime.

To a 1 L round flask charged with a stirring bar, hydroxylamine hydrochloride (79 g, 1.0 mol), (±)-camphor (79.2 g, 0.5 mol) and ethanol (0.6 L) were added. Sodium acetate (103 g, 1.25 mol) was added into the reaction mixture and stirred at 60° C. for 24 hours. After cooling, most of the ethanol in the reaction mixture was removed in vacuo. Water was then added, causing the crude oxime to precipitate from the solution as colorless crystals, which were isolated by filtration and washed with distilled water. The crystalline material was collected, dried under vacuum and recrystallized from absolute ethanol to afford (±)-camphor oxime (71.2 g, 85%); $R_f$=0.30 (Hexanes:EtOAc=5:1); $^1$H NMR (400 MHz, CDCl$_3$): δ 9.41 (br s, 1H), 2.53 (dt, J=18.0, 4.0 Hz, 1H), 2.03 (d, J=18.0 Hz, 1H), 1.89 (t, J=4.8 Hz, 1H), 1.87-1.75 (m, 1H), 1.74-1.63 (m, 1H), 1.48-1.38 (m, 1H), 1.26-1.16 (m, 1H), 0.98 (s, 3H), 0.89 (s, 3H), 0.77 (s, 3H); $^{13}$C NMR (100 MHz, CDCl$_3$): δ 169.8, 51.8, 48.3, 43.6, 33.1, 32.5, 27.2, 19.4, 18.5, 11.0.

(±)-Camphor Nitrimine.

(±)-Camphor oxime (33 g, 0.2 mol) in glacial acetic acid (900 mL) was treated with 5% aqueous sodium nitrite (500 mL). A bright yellow color developed and dispersed over 30 minutes. After a further 1.5 hours, the crude product was precipitated as a colorless solid by the addition of water and isolated by filtration. After drying under high vacuum, the crude product (34.2 g, 87%) was directly used for the next step reaction without further purification. $R_f$=0.40 (Hexanes:EtOAc=10:1); $^1$H NMR (400 MHz, CDCl$_3$): δ 2.74-2.64 (m, 1H), 2.13 (d, J=18.4, 1H), 2.03 (t, J=4.4 Hz, 1H), 1.97-1.79 (m, 2H), 1.65-1.50 (m, 1H), 1.38-1.28 (m, 1H), 1.04 (s, 3H), 0.98 (s, 3H), 0.88 (s, 3H).

(±)-Camphor N—H Imine.

A solution of (±)-camphor nitrimine (11.8 g, 60 mmol) in dry tetrahydrofuran (100 mL) was treated at 0° C. with a slow stream of ammonia gas for 6 hours. The solvent was removed in vacuo (keeping the water bath below 30° C.) to give the (±)-camphor imine as a pale yellow solid (8.6 g, 94%). $R_f$=0.30 (Hexanes:EtOAc=3:1); $^1$H NMR (400 MHz, CDCl$_3$): δ 8.18 (br s, 1H), 2.46-2.35 (m, 1H), 1.93 (d, J=17.2 Hz, 1H), 1.89-1.75 (m, 2H), 1.66-1.56 (m, 1H), 1.36-1.18 (m, 2H), 0.89 (s, 3H), 0.88 (s, 3H), 0.75 (s, 3H); $^{13}$C NMR (100.6 MHz, CDCl$_3$): δ 193.8, 54.6, 47.2, 43.6, 40.3, 32.0, 27.3, 19.5, 18.9, 10.3. The unpurified imine is homogeneous by spectroscopic analysis and is identical to that previously described. It was used immediately for the next step reaction without further purification.

(±)-Camphoryl N—H Oxaziridine 16.

A solution of purified m-CPBA (10.4 g, 60 mmol) in dry dichloromethane (250 mL) was cooled to −40° C., causing some of the peracid to crystallize from the solution. On addition of a solution of the (±)-camphor imine (8.32 g, 55 mmol) in dry dichloromethane (50 mL) to this solution over a period of 10 minutes, this solution became homogeneous. This reaction mixture was then stirred overnight at between −30° C. and −40° C. and allowed to reach room temperature. The reaction mixture was stirred at room temperature for a further 2 hours until all of the peracid had reacted (TLC), by which time much of the m-chlorobenzoic acid by-product had crystallized from the solution. The solution was concentrated in vacuo until approximately 25% of the original volume remained. Hexanes (200 mL) was added and the solution again concentrated in vacuo until approximately 25% of the original volume remained. This process was repeated once more and finally hexanes (300 mL) was added to the mixture. The precipitated m-chlorobenzoic acid was removed by filtration, and the rest of this by-product washed out of the resulting solution with aqueous sodium hydroxide (1.0 M, 3×100 mL). The organic solution was dried (Na$_2$SO$_4$) and the solvent was removed in vacuo to give the crude oxaziridine, which can be further purified by column chromatography (Hexanes:EtOAc=20:1) over silica gel to give (±)-camphoryl N—H oxaziridine 16 as a colorless solid (7.63 g, 83%).

(±)-Camphoryl N—H oxaziridine 16 was found by NMR spectroscopy to exist as a pair of diastereoisomers (A and B) at N—H in a 60:40 ratio (the major isomer is represented by A); $^1$H NMR (400 MHz, CDCl$_3$): δ 4.21 (br s, 1H$_A$), 3.74 (br s, 1H$_B$), 2.33-2.21 (m, 1H$_{A+B}$), 1.87-1.26 (m, 6H$_{A+B}$), 0.93 (s, 3H$_B$), 0.91 (s, 3H$_A$), 0.88 (s, 6H$_{A+B}$), 0.63 (s, 3H$_B$), 0.62 (s, 3H$_A$); $^{13}$C NMR (100 MHz, CDCl$_3$): δ 89.7, 89.4, 48.1, 47.8, 47.7, 47.5, 44.3, 44.2, 37.7, 36.5, 30.4, 29.5, 27.2, 27.0, 19.6, 19.5, 19.4, 19.3, 8.7, 8.4.

Synthesis of Fenchyl N—H Oxaziridine 18
[Adapted from literature procedure (58)]

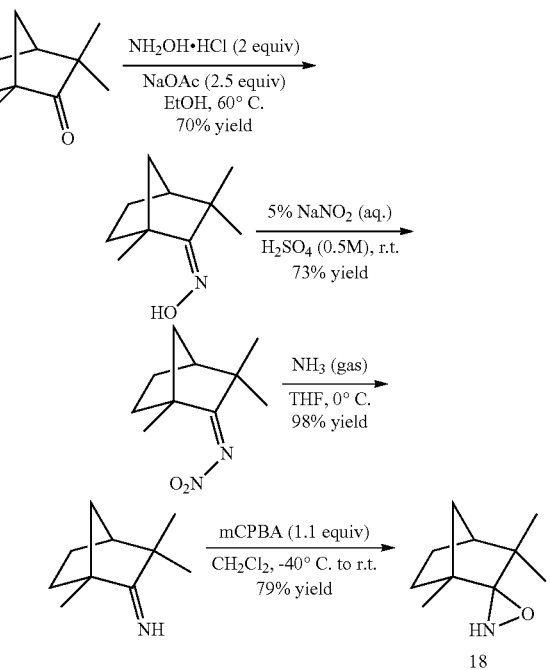

Scheme 2- Synthesis of Fenchyl N—H Oxaziridine 18

(−)-Fenchone Oxime.

To a 1 L round flask charged with a stirring bar, hydroxylamine hydrochloride (79 g, 1.0 mol), (−)-fenchone (77.7 g, 0.5 mol) and ethanol (0.6 L) were added. Sodium acetate (103 g, 1.25 mol) was added into the reaction mixture and stirred at 60° C. for 24 hours. After cooling, most of the ethanol in the reaction mixture was removed in vacuo. Water was then added, causing the crude oxime to precipitate from the solution as colorless crystals, which were isolated by filtration and washed with distilled water. The crystalline material was collected, dried under vacuum and recrystallized from absolute ethanol to afford (−)-fenchone oxime (58.2 g, 70%); $R_f$=0.30 (Hexanes:EtOAc=5:1); $^1$H NMR (400 MHz, CDCl$_3$): δ 8.82 (br s, 1H), 1.86-1.69 (m, 3H), 1.64-1.40 (m, 3H), 1.36-1.33 (m, 1H), 1.32 (s, 3H), 1.29 (s, 3H), 1.22 (s, 3H); $^{13}$C NMR (100 MHz, CDCl$_3$): δ 172.5, 50.1, 48.5, 44.2, 43.2, 34.1, 25.2, 22.8, 22.1, 17.1.

(−)-Fenchone Nitrimine.

A solution of sodium nitrite (23.5 g, 0.34 mol, 1.7 equiv) in water (150 mL) was added to a solution of (−)-fenchone oxime (33.5 g, 0.2 mol) in diethyl ether (300 mL) in a 1 L flask. A solution of 0.5 M sulfuric acid (330 mL) was added with occasional vigorous swirling over 2 hours at r.t. The mixture was allowed to stand for a further 3 hours, and the ether layer was separated, washed with saturated aqueous sodium hydrogen carbonate (2×100 mL), dried (Na$_2$SO$_4$) and the solvent removed in vacuo. After drying under high vacuum, the crude product (28.5 g, 73%) was directly used for the next step reaction without further purification. $R_f$=0.30 (Hexanes:EtOAc=10:1); The (−)-fenchone nitrimine was shown by NMR spectroscopy to be a mixture of syn and anti diastereoisomers (A and B) present in an approximately 2:1 ratio (the major isomer is represented by A): $^1$H NMR (400 MHz, CDCl$_3$): δ 2.03-1.52 (m, 6H$_{A+B}$), 1.47 (d, J=10.4 Hz, 1H$_A$), 1.36 (d, J=10.4 Hz, 1H$_B$), 1.28 (s, 3H$_{A+B}$), 1.24 (s, 3H$_A$), 1.21 (s, 3H$_B$), 1.18 (s, 3H$_A$), 1.16 (s, 3H$_B$); $^{13}$C NMR (100 MHz, CDCl$_3$): δ 189.9, 189.8, 53.6, 52.3, 49.7, 47.3, 46.7, 45.5, 45.0, 42.1, 34.0, 33.6, 26.0, 25.1, 24.6, 24.4, 23.7, 22.6, 16.1, 15.1.

(−)-Fenchone N—H Imine.

A solution of (−)-fenchone nitrimine (10.2 g, 52 mmol) in dry tetrahydrofuran (100 mL) was treated at 0° C. with a slow stream of ammonia gas for 6 hours. The solvent was removed in vacuo (keeping the water bath below 30° C.) to give the (−)-fenchone imine as an unstable pale yellow liquid (7.7 g, 98%). $R_f$=0.30 (Hexanes:EtOAc=3:1); $^1$H NMR (400 MHz, CDCl$_3$): δ 8.20 (br s, 1H), 2.01-1.95 (m, 1H), 1.75-1.69 (m, 1H), 1.68-1.55 (m, 2H), 1.49 (td, J=12.0, 3.6 Hz, 1H), 1.38 (dd, J=10.4, 1.6 Hz, 1H), 1.34-1.23 (m, 1H), 1.18 (s, 3H), 1.08 (s, 3H), 1.05 (s, 3H); $^{13}$C NMR (100 MHz, CDCl$_3$): δ 199.9, 51.9, 46.1, 44.8, 42.6, 33.3, 26.0, 25.0, 23.6, 16.0. The unpurified imine is homogeneous by spectroscopic analysis and is identical to that previously described. It was used immediately for the next step reaction without further purification.

(−)-Fenchyl N—H Oxaziridine 18.

A solution of purified m-CPBA (9.7 g, 56 mmol) in dry dichloromethane (250 mL) was cooled to −40° C., causing some of the peracid to crystallize from the solution. On addition of a solution of the (−)-fenchone imine (7.7 g, 51 mmol) in dry dichloromethane (50 mL) to this solution over a period of 10 minutes, this solution became homogeneous. This reaction mixture was then stirred overnight at between −30° C. and −40° C. and allowed to reach room temperature. The reaction mixture was stirred at room temperature for a further 2 hours until all of the peracid had reacted (TLC), by which time much of the m-chlorobenzoic acid by-product had crystallized from the solution. The solution was concentrated in vacuo until approximately 25% of the original volume remained. Hexanes (200 mL) was added and the solution again concentrated in vacuo until approximately 25% of the original volume remained. This process was repeated once more and finally hexanes (300 mL) was added to the mixture. The precipitated m-chlorobenzoic acid was removed by filtration, and the rest of this by-product washed out of the resulting solution with aqueous sodium hydroxide (1.0 M, 3×100 mL). The organic solution was dried (Na$_2$SO$_4$) and the solvent was removed in vacuo to give the crude oxaziridine, which can be further purified by column chromatography (Hexanes:EtOAc=20:1) over silica gel to give (−)-fenchyl N—H oxaziridine 18 as a colorless oil (6.9 g, 79%).

(−)-Fenchyl N—H oxaziridine was found by NMR spectroscopy to exist as a pair of diastereoisomers (A and B) at N—H in a 60:40 ratio (the major isomer is represented by A); $^1$H NMR (600 MHz, CDCl$_3$): δ 3.82 (br s, 1H$_B$), 3.70 (br s, 1H$_A$), 1.98-1.90 (m, 1H$_{A+B}$), 1.88-1.68 (m, 2H$_A$/B), 1.62-1.26 (m, 4H$_{A+B}$), 0.96 (s, 3H$_A$/B), 0.94 (s, 3H$_{A+B}$), 0.88 (s, 3H$_A$/B), 0.87 (s, 3H$_{A+B}$); $^{13}$C NMR (151 MHz, CDCl$_3$): δ 93.4, 92.9, 47.3, 47.2, 46.60, 41.8, 41.1, 39.8, 31.7, 31.1, 25.2, 23.3, 23.2, 22.6, 22.4, 14.0, 13.0.

Synthesis of Camphoryl N-Me Oxaziridine 19a
[Adapted from Literature Procedure (58)]

Scheme 3- Synthesis of Camphoryl N—Me Oxaziridine 19a

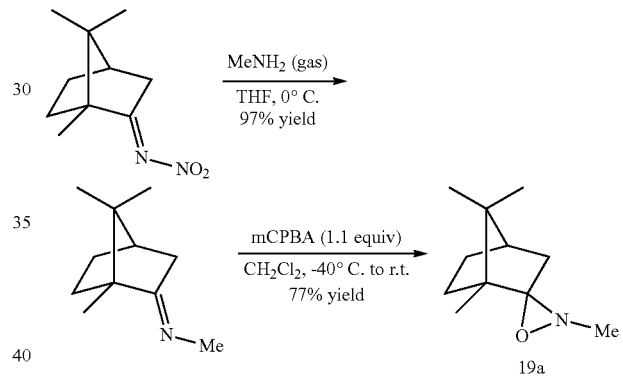

(±)-Camphor N-Me Imine.

A solution of (±)-camphor nitrimine (9.5 g, 48 mmol) in dry tetrahydrofuran (100 mL) was treated at 0° C. with a slow stream of methanamine gas for 5 hours. The solvent was removed in vacuo (keeping the water bath below 30° C.) to give the (±)-camphor N-Me imine as a pale yellow liquid (7.7 g, 97%). $R_f$=0.30 (Hexanes:EtOAc=3:1); $^1$H NMR (400 MHz, CDCl$_3$): δ 3.00 (s, 3H), 2.35-2.25 (m, 1H), 1.92 (t, J=4.0 Hz, 1H), 1.89-1.75 (m, 2H), 1.62 (td, J=12.4, 4.4 Hz, 1H), 1.36-1.24 (m, 1H), 1.20-1.10 (m, 1H), 0.93 (s, 3H), 0.88 (s, 3H), 0.70 (s, 3H); $^{13}$C NMR (100 MHz, CDCl$_3$): δ 184.7, 53.7, 47.2, 43.7, 38.9, 35.2, 31.9, 27.3, 19.4, 18.8, 11.2.

(±)-Camphoryl N-Me Oxaziridine 19a.

A solution of purified m-CPBA (5.7 g, 33 mmol) in dry dichloromethane (120 mL) was cooled to −40° C., causing some of the peracid to crystallize from the solution. On addition of a solution of the (±)-camphor N-Me imine (4.96 g, 30 mmol) in dry dichloromethane (30 mL) to this solution over a period of 10 minutes, this solution became homogeneous. This reaction mixture was then stirred overnight at between −30° C. and −40° C. and allowed to reach room temperature. The reaction mixture was stirred at room temperature for a further 2 hours until all of the peracid had reacted (TLC), by which time much of the m-chlorobenzoic acid by-product had crystallized from the solution. The solution was concentrated in vacuo until approximately 25% of the original volume remained. Hexanes (100 mL) was added and the solution again concentrated in vacuo until approximately 25% of the original volume remained. This process was repeated once more and finally hexanes (150 mL) was added to the mixture. The precipitated m-chlorobenzoic acid was removed by filtration, and the rest of this by-product washed out of the resulting solution with aqueous sodium hydroxide (1.0 M, 3×50 mL). The organic solution was dried (Na$_2$SO$_4$) and the solvent was removed in vacuo to give the crude oxaziridine, which can be further purified by column chromatography (Hexanes:EtOAc=20:1) over silica gel to give (±)-camphoryl N-Me oxaziridine 19a as a colorless solid (4.2 g, 77%). $^1$H NMR (400 MHz, CDCl$_3$): δ 2.58 (s, 3H), 2.28-2.20 (m, 1H), 1.90-1.75 (m, 2H), 1.63-1.50 (m, 1H), 1.48-1.25 (m, 3H), 0.89 (s, 3H), 0.81 (s, 3H), 0.61 (s, 3H); $^{13}$C NMR (100 MHz, CDCl$_3$): δ 94.1, 49.2, 46.7, 44.3, 42.1, 32.3, 29.3, 27.2, 19.4, 19.3, 9.2.

Synthesis of Camphoryl N-Bn Oxaziridine 19b
[Adapted from Literature Procedure (58)]

Scheme 4- Synthesis of Camphoryl N—Bn Oxaziridine 19b

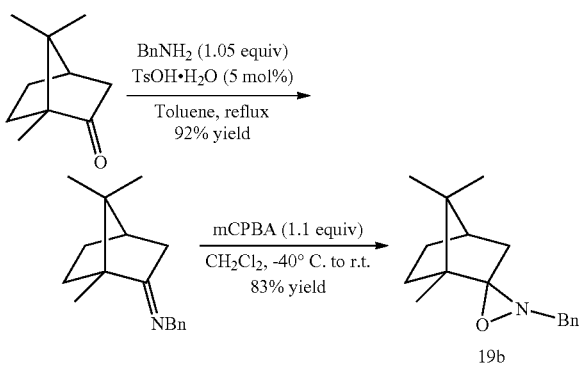

(+)-Camphor N-Bn Imine

A solution of (±)-camphor (7.6 g, 50 mmol), benzylamine (5.6 g, 52.5 mmol, 1.05 equiv) and p-toluenesulfonic acid monohydrate (0.48 g, 2.5 mmol, 0.05 equiv) in toluene (100 mL) was treated at 130° C. with a Dean-Stark for 12 hours. After cooling, most of the toluene in the reaction mixture was removed in vacuo. The precipitates from the solution were removed by filtration. The organic solution was washed by saturated NaHCO$_3$ solution (2×100 mL) and brine (100 mL), dried over Na$_2$SO$_4$. The solvent was removed in vacuo to give the (±)-camphor N-Bn imine as a colorless liquid (11.1 g, 92%). R$_f$=0.30 (Hexanes:EtOAc=5:1); $^1$H NMR (400 MHz, CDCl$_3$): δ 7.38-7.26 (m, 4H), 7.25-7.18 (m, 1H), 4.51 (d, J=14.8 Hz, 1H), 4.44 (d, J=14.8 Hz, 1H), 2.48-2.35 (m, 1H), 2.00-1.80 (m, 3H), 1.71 (td, J=12.4, 4.0 Hz, 1H), 1.48-1.35 (m, 1H), 1.30-1.15 (m, 1H), 1.05 (s, 3H), 0.95 (s, 3H), 0.78 (s, 3H); $^{13}$C NMR (100 MHz, CDCl$_3$): δ 183.6, 140.4, 128.2, 127.4, 126.3, 55.5, 53.9, 47.1, 43.8, 35.8, 32.2, 27.4, 19.6, 19.0, 11.4.

(+)-Camphoryl N-Bn Oxaziridine 19b.

A solution of purified m-CPBA (7.9 g, 46 mmol) in dry dichloromethane (150 mL) was cooled to −40° C., causing some of the peracid to crystallize from the solution. On addition of a solution of the (±)-camphor N-Bn imine (10.5 g, 44 mmol) in dry dichloromethane (50 mL) to this solution over a period of 15 minutes, this solution became homogeneous. This reaction mixture was then stirred overnight at between −30° C. and −40° C. and allowed to reach room temperature. The reaction mixture was stirred at room temperature for a further 2 hours until all of the peracid had reacted (TLC), by which time much of the m-chlorobenzoic acid by-product had crystallized from the solution. The solution was concentrated in vacuo until approximately 25% of the original volume remained. Hexanes (150 mL) was added and the solution again concentrated in vacuo until approximately 25% of the original volume remained. This process was repeated once more and finally hexanes (200 mL) was added to the mixture. The precipitated m-chlorobenzoic acid was removed by filtration, and the rest of this by-product washed out of the resulting solution with aqueous sodium hydroxide (1.0 M, 3×100 mL). The organic solution was dried (Na$_2$SO$_4$) and the solvent was removed in vacuo to give the crude oxaziridine, which can be further purified by column chromatography (Hexanes:EtOAc=20:1) over silica gel to give (±)-camphoryl N-Bn oxaziridine 19b as a colorless solid (9.4 g, 83%). $^1$H NMR (400 MHz, CDCl$_3$): δ 7.43 (d, J=7.6 Hz, 2H), 7.35 (t, J=7.2 Hz, 2H), 7.28 (d, J=7.2 Hz, 1H), 3.86 (d, J=14.8 Hz, 1H), 3.64 (d, J=14.0 Hz, 1H), 2.48-2.37 (m, 1H), 1.91 (t, J=4.8 Hz, 1H), 1.88-1.78 (m, 1H), 1.68-1.54 (m, 2H), 1.52-1.32 (m, 2H), 0.91 (s, 3H), 0.76 (s, 3H), 0.67 (s, 3H); $^{13}$C NMR (100 MHz, CDCl$_3$): δ 136.6, 128.52, 128.45, 127.4, 94.2, 59.4, 49.3, 46.9, 44.4, 33.2, 29.4, 27.1, 19.4, 19.3, 9.3.

Synthesis of Oxaziridine 30 [Adapted from Literature Procedure (60)]

Scheme 5-Synthesis of oxaziridine 30

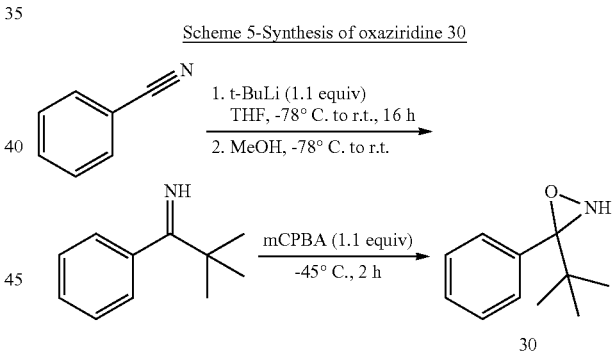

tert-Butyllithium (1.7 M, 16.4 mL, 28 mmol, 1.1 eq.) was slowly added to a solution of benzonitrile (2.58 g, 25 mmol, 1.0 eq.) in 50 mL THF at −78° C. The reaction was allowed to reach room temperature. After 16 h, the reaction mixture was cooled back to −78° C. and 5 mL of anhydrous MeOH was added. After reaching room temperature, the reaction mixture was diluted with 50 mL hexanes and filtered through a pad of celite. The filtrate was concentrated under reduced pressure. The crude imine was re-dissolved in 25 mL of anhydrous DCM and slowly added to a suspension of m-CPBA (4.75 g, 27.5 mmol, 1.1 eq.) in 125 mL anhydrous DCM at −45° C. After 2 h at −45° C., the reaction mixture was allowed to reach room temperature. The solvent was carefully evaporated under reduced temperature, and 50 mL hexanes was added to the residue. The suspension was filtered and the solid was washed with additional hexanes (2×50 mL) before being discarded. The combined filtrate was washed once with 100 mL saturated aqueous NaHCO$_3$ and dried over anhydrous $Na_2SO_4$. The solvent was removed under reduced pressure and the residue was purified by silica gel chromatography (Hexanes:EtOAc=25:1) to give 31 as a colorless oil (2.6 g, 58% over 2 steps). The product exists as a single pair of diastereomers (A and B). $^1$H NMR (600 MHz, $CDCl_3$) δ 7.41-7.30 (m, 5H, A & B), 4.40 (s, 1H, A), 3.85 (s, 1H, B), 1.07 (s, 9H, A), 1.03 (s, 9H, B); $^{13}$C NMR (151 MHz, $CDCl_3$) δ 138.0, 132.7, 132.1, 129.1, 128.5, 128.0, 127.6, 127.6, 127.4, 86.2, 35.0, 25.5, 25.5.

Synthesis of Di-t-Butyl Oxaziridine 31 [Adapted from Literature Procedure (57)]

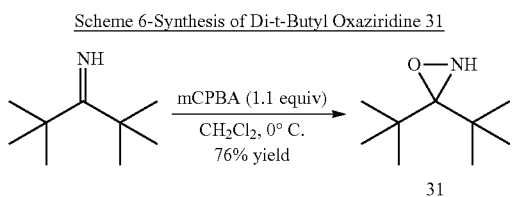

Scheme 6-Synthesis of Di-t-Butyl Oxaziridine 31

To a solution of 2,2,4,4-tetramethylpentan-3-imine (5 g, 35 mmol) in 20 mL of $CH_2Cl_2$ was added dropwise a solution of m-CPBA (7.1 g, 39 mmol, 1.1 equiv) in 80 mL of $CH_2Cl_2$ at 0° C. The reaction mixture was stirred at 0° C. for 3 hours, and then concentrated in vacuo to remove half of the solvent and filtered the m-chlorobenzoic acid by-product from the mixture. Hexanes (50 mL) was added and the solution again concentrated in vacuo until approximately 25% of the original volume remained. This process was repeated once more and finally hexanes (50 mL) was added to the mixture. The precipitated m-chlorobenzoic acid was removed by filtration, and the rest of this by-product washed out of the resulting solution with aqueous sodium hydroxide (1.0 M, 3×50 mL). The organic solution was dried ($Na_2SO_4$) and the solvent was removed in vacuo to give the crude oxaziridine, which can be further purified by column chromatography (Hexanes:EtOAc=40:1) over silica gel to give di-t-butyl oxaziridine 31 as a colorless oil (4.2 g, 76%). $^1$H NMR (600 MHz, $CDCl_3$): δ 3.78 (br s, 1H), 1.13 (s, 9H), 1.09 (s, 9H); $^{13}$C NMR (151 MHz, $CDCl_3$): δ 85.2, 37.5, 28.1, 27.9.

B. Amination of Arylmetals

Method A:

To a flame-dried 25 mL round bottom flask was charged activated Mg (7.5 mmol, 1.5 eq.) and 5 mL anhydrous THF. To this suspension was added 2 drops of 1,2-dibromoethane. After 5 min, a solution of Aryl bromide (5 mmol, 1.0 eq.) in 5 mL anhydrous THF was slowly added to the suspension of Mg at room temperature. The reaction was mildly exothermic. The Grignard reagent was titrated and 1 mmol of this reagent was added to a flame-dried reaction vial. The solution was diluted with 3 mL anhydrous toluene and after cooling to the target temperature T, a solution of oxaziridine (1.2 mmol, 1.2 eq.) in 1 mL anhydrous toluene was added. The reaction was maintained at the targeted temperature T for time t before being quenched with saturated aqueous $NH_4Cl$. (The actual temperature/reaction time is listed for each substrate.)

Method B:

To a flame-dried reaction vial was added iPrMgCl.LiCl (1.1 mmol, 1.1 eq., commercially-available THF solution from Aldrich). A solution of aryl iodide (1.0 mmol, 1.0 eq.) in 2 mL THF was added at −45° C. After 2 h, 3 mL of anhydrous toluene was added at −45° C., followed by a solution of oxaziridine (1.2 mmol, 1.2 eq.) in 1 mL anhydrous toluene. The reaction temperature was maintained at −45° C. for 2 h before being quenched with saturated aqueous $NH_4Cl$.

Method C:

To a flame-dried reaction vial was added TMPMgCl.LiCl (1.1 mmol, 1.1 eq., commercially-available THF solution from Aldrich). A solution of aromatic or hetero-aromatic substrate (1.0 mmol, 1.0 eq.) in 2 mL THF was added at the temperature $T_1$. After target time $t_1$, the solution was cooled to temperature T2 and 3 mL anhydrous toluene was added, followed by a solution of oxaziridine (1.2 mmol, 1.2 eq.) in 1 mL anhydrous toluene. The reaction was maintained at the targeted temperature $T_2$ for $t_2$ before being quenched with saturated aqueous $NH_4Cl$. (The actual temperature/reaction time is listed for each substrate.)

Method D:

To a flame-dried reaction vial was added a solution of aryl bromide (1.0 mmol, 1.0 eq.) in 2 mL anhydrous THF. A solution of n-BuLi in hexanes (1.1 mmol, 1.1 eq.) was slowly added at −78° C. and the temperature was maintained. After 30 min, a solution of oxaziridine (1.2 mmol, 1.2 eq.) in 4 mL anhydrous toluene was added at −78° C. The reaction was allowed to proceed at −78° C. for 2 h before being quenched with saturated aqueous $NH_4Cl$.

Method E:

To a flame-dried reaction vial was added a solution of aryl bromide (1.0 mmol, 1.0 eq.) in 2 mL anhydrous THF. A solution of n-BuLi in hexanes (1.1 mmol, 1.1 eq.) was slowly added at −78° C. and the temperature was maintained at −78° C. After 30 min, this aryl lithium solution was transferred to a suspension of $MgBr_2$ (1.0 mmol, 1.0 eq., freshly prepared from Mg and $BrCH_2CH_2Br$) at −78° C. The reaction mixture was allowed to reach room temperature over 30 min before being cooled to the target temperature T. A solution of oxaziridine (1.2 mmol, 1.2 eq.) in 4 mL anhydrous toluene was added to the reaction mixture at T. The reaction was maintained at the targeted temperature T for 2 h before being quenched with saturated aqueous $NH_4Cl$. (The actual temperature/reaction time is listed for each substrate.)

Workup and Purification:

After quenching, the reaction was diluted with 20 mL saturated aqueous NaCl and 20 mL EtOAc. The organic layer was separated and the aqueous layer was extracted with EtOAc (2×20 mL). The combined organic layer was dried over anhydrous $Na_2SO_4$, filtered and concentrated under reduced pressure. The residue was purified with flash chromatography.

a. Naphthalen-2-amine (23a)

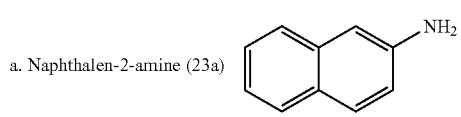 [SMILES: Nc1ccc2ccccc2c1]

Method A, T=−78° C., t=2 h; Yield=89%; $R_f$=0.25 (Hexanes:EtOAc=4:1); $^1$H NMR (400 MHz, $CDCl_3$): δ 7.75 (d, J=8.0 Hz, 1H), 7.70 (d, J=8.4 Hz, 1H), 7.64 (d, J=8.4 Hz, 1H), 7.43 (t, J=7.2 Hz, 1H), 7.29 (t, J=7.2 Hz, 1H), 7.02-6.94 (m, 2H), 3.82 (br s, 2H); $^{13}$C NMR (100 MHz, $CDCl_3$): δ 144.0, 134.8, 129.1, 127.9, 127.6, 126.3, 125.7, 122.4, b. 6-Methoxynaphthalen-2-amine (23b)

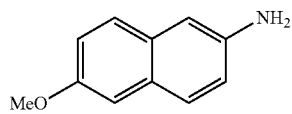

Method A, T=−78° C., t=2 h; Yield=78%; $R_f$=0.30 (Hexanes:EtOAc=3:1); $^1$H NMR (400 MHz, CDCl$_3$): δ 7.58 (d, J=8.8 Hz, 1H), 7.52 (d, J=8.8 Hz, 1H), 7.11-7.03 (m, 2H), 6.98-6.90 (m, 2H), 3.89 (s, 3H), 3.73 (br s, 2H); $^{13}$C NMR (100 MHz, CDCl$_3$): δ 155.3, 142.3, 130.2, 128.6, 127.9, 127.3, 118.9, 118.7, 109.2, 106.0, 55.2. Spectral data is in accordance with the literature report (Lee, et al., 2001).

c. Naphthalen-1-amine (23c)

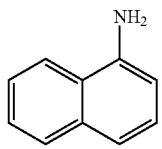

Method A, T=−45° C., t=2 h; Yield=63%; $R_f$=0.25 (Hexanes:EtOAc=4:1); $^1$H NMR (400 MHz, CDCl$_3$): δ 7.89-7.80 (m, 2H), 7.55-7.46 (m, 2H), 7.41-7.31 (m, 2H), 6.81 (dd, J=6.8, 1.2 Hz, 1H), 4.12 (br s, 2H); $^{13}$C NMR (100 MHz, CDCl$_3$): δ 142.0, 134.3, 128.5, 126.3, 125.8, 124.8, 123.5, 120.7, 118.8, 109.6. Spectral data is in accordance with the literature report (Zhu, et al., 2012).

d. 4-Fluoronaphthalen-1-amine (23d)

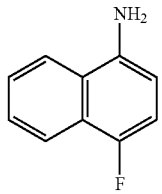

Method A, T=−45° C., t=2 h; Yield=31%; $R_f$=0.30 (Hexanes:EtOAc=4:1); $^1$H NMR (400 MHz, CDCl$_3$): δ 8.09 (dd, J=7.2, 2.4 Hz, 1H), 7.85-7.80 (m, 1H), 7.58-7.50 (m, 2H), 6.98 (dd, J=10.4, 8.0 Hz, 1H), 6.66 (dd, J=8.4, 4.4 Hz, 1H), 3.99 (br s, 2H); $^{13}$C NMR (100 MHz, CDCl$_3$): δ 152.6 (d, J=240.9 Hz), 138.1 (d, J=2.9 Hz), 126.1 (d, J=2.2 Hz), 125.8, 124.5 (d, J=16.8 Hz), 124.1 (d, J=16.8 Hz), 121.1, 121.0, 109.4 (d, J=20.5 Hz), 108.6 (d, J=8.0 Hz); $^{19}$F NMR (376 MHz, CDCl$_3$): δ −134.6 (m). Spectral data is in accordance with the literature report (Kitching, et al., 1977)

e.

(23e)

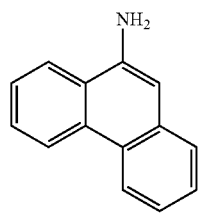

Phenanthren-9-amine

Method A, T=−45° C., t=3 h; Yield=52%; $R_f$=0.30 (Hexanes:EtOAc=4:1); $^1$H NMR (400 MHz, CDCl$_3$): δ 8.73 (dd, J=8.4, 1.2 Hz, 1H), 8.59 (d, J=8.0 Hz, 1H), 7.93 (dd, J=8.0, 1.2 Hz, 1H), 7.73-7.61 (m, 3H), 7.56-7.50 (m, 1H), 7.49-7.42 (m, 1H), 6.99 (s, 1H), 4.14 (br s, 2H); $^{13}$C NMR (100 MHz, CDCl$_3$): δ 139.8, 133.2, 131.1, 126.8, 126.6, 126.3, 126.2, 126.1, 125.4, 123.4, 123.3, 122.4, 121.2, 107.4. Spectral data is in accordance with the literature report (Zhu, et al., 2012).

f.

(23f)

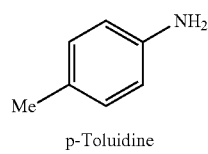

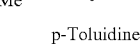

p-Toluidine

Method A, T=−78° C., t=2 h; Yield=61%; $R_f$=0.35 (Hexanes:EtOAc=4:1); $^1$H NMR (400 MHz, CDCl$_3$): δ 6.97 (d, J=8.0 Hz, 2H), 6.62 (d, J=8.8 Hz, 2H), 3.53 (br s, 2H), 2.25 (s, 3H); $^{13}$C NMR (100 MHz, CDCl$_3$): δ 143.8, 129.7, 127.8, 115.2, 20.4. Spectral data is in accordance with the literature report (Lee, et al., 2001).

g.

(23g)

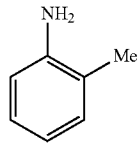

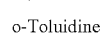

o-Toluidine

Method A, T=−45° C., t=2 h; Yield=47%; $R_f$=0.30 (Hexanes:EtOAc=4:1); $^1$H NMR (400 MHz, CDCl$_3$): δ 7.11-7.04 (m, 2H), 6.79-6.68 (m, 2H), 3.61 (br s, 2H), 2.20 (s, 3H); $^{13}$C NMR (100 MHz, CDCl$_3$): δ 144.5, 130.4, 126.9, 122.2, 118.5, 114.9, 17.3. Spectral data is in accordance with the literature report (Xu and Wolf, 2009).

h.

(23h)

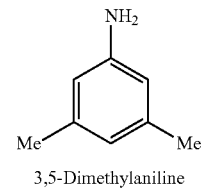

3,5-Dimethylaniline

Method A, T=−78° C., t=2 h; Yield=74%; $R_f$=0.35 (Hexanes:EtOAc=4:1); $^1$H NMR (400 MHz, CDCl$_3$): δ 6.50 (s, 1H), 6.39 (s, 2H), 3.63 (br s, 2H), 2.31 (s, 6H); $^{13}$C NMR (100 MHz, CDCl$_3$): δ 146.1, 138.8, 120.4, 113.0, 21.2. Spectral data is in accordance with the literature report (Xu and Wolf, 2009).

i.

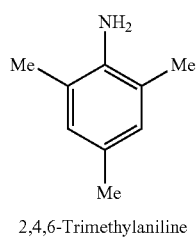

2,4,6-Trimethylaniline (23i)

Method A, T=−45° C., t=3 h; Yield=26%; $R_f$=0.30 (Hexanes:EtOAc=4:1); $^1$H NMR (400 MHz, CDCl$_3$): δ 6.81 (s, 2H), 3.48 (br s, 2H), 2.25 (s, 3H), 2.19 (s, 6H); $^{13}$C NMR (100 MHz, CDCl$_3$): δ 140.1, 128.8, 127.1, 121.8, 20.3, 17.5. Spectral data is in accordance with the literature report (Zhu, et al., 2012).

j.

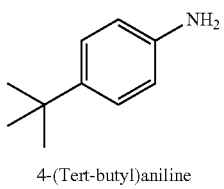

4-(Tert-butyl)aniline (23j)

Method A, T=−78° C., t=2 h; Yield=70%; $R_f$=0.30 (Hexanes:EtOAc=4:1); $^1$H NMR (600 MHz, CDCl$_3$): δ 7.21 (d, J=8.4 Hz, 2H), 6.67 (d, J=8.4 Hz, 2H), 3.52 (br s, 2H), 1.31 (s, 9H); $^{13}$C NMR (150 MHz, CDCl$_3$): δ 143.7, 141.4, 126.0, 114.9, 33.9, 31.5. Spectral data is in accordance with the literature report (Lee, et al., 2001).

k.

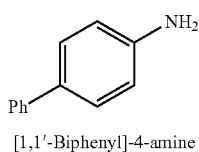

[1,1′-Biphenyl]-4-amine (23k)

Method A, T=−78° C., t=2 h; Yield=92%; $R_f$=0.25 (Hexanes:EtOAc=4:1); $^1$H NMR (400 MHz, CDCl$_3$): δ 7.57 (d, J=7.6 Hz, 2H), 7.48-7.40 (m, 4H), 7.30 (t, J=7.6 Hz, 1H), 6.78 (d, J=8.4 Hz, 2H), 3.73 (br s, 2H); $^{13}$C NMR (100 MHz, CDCl$_3$): δ 145.8, 141.1, 131.5, 128.6, 128.0, 126.3, 126.2, 115.3. Spectral data is in accordance with the literature report (Lee, et al., 2001).

l.

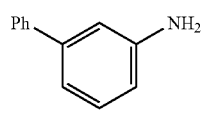

[1,1′-Biphenyl]-3-amine (23l)

Method A, T=−78° C., t=2 h; Yield=82%; $R_f$=0.35 (Hexanes:EtOAc=4:1); $^1$H NMR (400 MHz, CDCl$_3$): δ 7.60-7.55 (m, 2H), 7.43 (t, J=7.2 Hz, 2H), 7.37-7.33 (m, 1H), 7.24 (t, J=8.4 Hz, 1H), 7.03-6.98 (m, 1H), 6.92 (t, J=2.0 Hz, 1H), 6.72-6.66 (m, 1H), 3.74 (br s, 2H); $^{13}$C NMR (100 MHz, CDCl$_3$): δ 146.7, 142.4, 141.4, 129.6, 128.6, 127.2, 127.1, 117.7, 114.1, 113.9. Spectral data is in accordance with the literature report (Sharma, et al., 2014).

m.

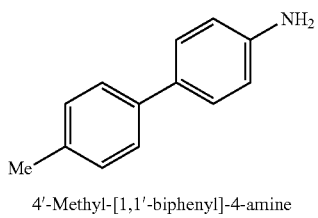

4′-Methyl-[1,1′-biphenyl]-4-amine (23m)

Method A, T=−78° C., t=2 h; Yield=85%; $R_f$=0.35 (Hexanes:EtOAc=4:1); $^1$H NMR (400 MHz, CDCl$_3$): δ 7.55 (d, J=8.4 Hz, 2H), 7.50 (d, J=8.4 Hz, 2H), 7.32 (d, J=8.0 Hz, 2H), 6.81 (d, J=8.8 Hz, 2H), 3.71 (br s, 2H), 2.48 (s, 3H); $^{13}$C NMR (100 MHz, CDCl$_3$): δ 145.5, 138.2, 135.7, 131.3, 129.3, 127.7, 126.1, 115.3, 20.9. Spectral data is in accordance with the literature report (Borzenko, et al., 2015).

n.

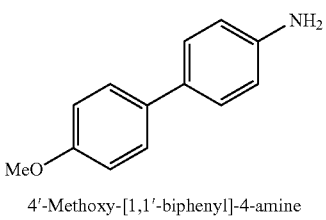

4′-Methoxy-[1,1′-biphenyl]-4-amine (23n)

Method A, T=−78° C., t=2 h; Yield=83%; $R_f$=0.35 (Hexanes:EtOAc=3:1); $^1$H NMR (600 MHz, CDCl$_3$): δ 7.58 (d, J=7.2 Hz, 2H), 7.48 (d, J=7.2 Hz, 2H), 7.06 (d, J=7.8 Hz, 2H), 6.86 (d, J=7.2 Hz, 2H), 3.96 (s, 3H), 3.81 (br s, 2H); $^{13}$C NMR (151 MHz, CDCl$_3$): δ 158.4, 145.3, 133.9, 131.3, 127.6, 127.4, 115.4, 114.1, 55.3. Spectral data is in accordance with the literature report (Borenko, et al., 2015).

o.

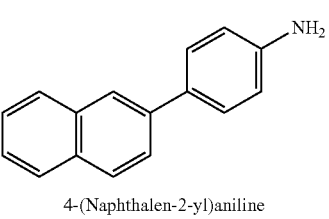

4-(Naphthalen-2-yl)aniline (23o)

Method A, T=−78° C., t=2 h; Yield=62%; $R_f$=0.30 (Hexanes:EtOAc=4:1); $^1$H NMR (400 MHz, CDCl$_3$): δ 7.98 (s, 1H), 7.91-7.83 (m, 3H), 7.73 (dd, J=8.8, 2.0 Hz, 1H), 7.57 (dd, J=6.4, 2.0 Hz, 2H), 7.51-7.44 (m, 2H), 6.81 (dd, J=6.8, p.

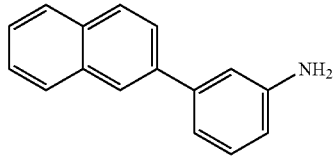

3-(Naphthalen-2-yl)aniline

Method A, T=−78° C., t=2 h; Yield=79%; $R_f$=0.30 (Hexanes:EtOAc=4:1); $^1$H NMR (400 MHz, CDCl$_3$): δ 8.05 (s, 1H), 7.94-7.86 (m, 3H), 7.75 (dd, J=8.4, 1.6 Hz, 1H), 7.54-7.48 (m, 2H), 7.30 (t, J=8.0 Hz, 1H), 7.15 (d, J=8.0 Hz, 1H), 7.05 (t, J=2.0 Hz, 1H), 6.76-6.70 (m, 1H), 3.73 (br s, 2H); $^{13}$C NMR (100 MHz, CDCl$_3$): δ 146.8, 142.3, 138.7, 133.6, 132.6, 129.7, 128.2, 128.1, 127.6, 126.2, 125.8, 125.64, 125.60, 117.9, 114.2, 114.1. Spectral data is in accordance with the literature report (Chen, et al., 2011).

q.

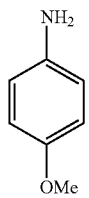

4-Methoxyaniline

Method A, T=−78° C., t=2 h; Yield=63%; $R_f$=0.32 (Hexanes:EtOAc=4:1); $^1$H NMR (400 MHz, CDCl$_3$): δ 6.79-6.72 (m, 2H), 6.68-6.61 (m, 2H), 3.75 (s, 3H), 3.43 (br s, 2H); $^{13}$C NMR (100 MHz, CDCl$_3$): δ 152.6, 139.8, 116.3, 114.6, 55.6. Spectral data is in accordance with the literature report (Lee, et al., 2001).

r.

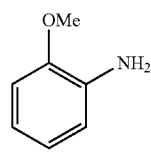

2-Methoxyaniline

Method A, T=−45° C., t=2 h; Yield=61%; $R_f$=0.30 (Hexanes:EtOAc=4:1); $^1$H NMR (400 MHz, CDCl$_3$): δ 6.87-6.81 (m, 2H), 6.80-6.73 (m, 1H), 3.88 (s, 3H), 3.82 (br s, 2H); $^{13}$C NMR (100 MHz, CDCl$_3$): δ 147.2, 136.1, 120.0, 118.3, 114.9, 110.3, 55.3. Spectral data is in accordance with the literature report (Green and Hartwig, 2014).

s.

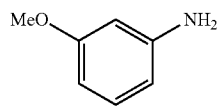

3-Methoxyaniline

Method A, T=−78° C., t=2 h; Yield=67%; $R_f$=0.30 (Hexanes:EtOAc=4:1); $^1$H NMR (400 MHz, CDCl$_3$): δ 7.09 (t, J=8.4 Hz, 1H), 6.39-6.29 (m, 2H), 6.27 (t, J=2.4 Hz, 1H), 3.78 (s, 3H), 3.71 (br s, 2H); $^{13}$C NMR (100 MHz, CDCl$_3$): δ 160.6, 147.6, 129.9, 107.8, 103.8, 100.9, 54.9. Spectral data is in accordance with the literature report (Lee, et al., 2001).

t.

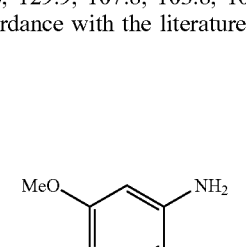

2,5-Dimethoxyaniline

Method A, T=−45° C., t=2 h; Yield=58%; $R_f$=0.35 (Hexanes:EtOAc=3:1); $^1$H NMR (400 MHz, CDCl$_3$): δ 6.70 (d, J=8.8 Hz, 1H), 6.34 (d, J=2.8 Hz, 1H), 6.25 (dd, J=8.4, 2.8 Hz, 1H), 3.84 (br s, 2H), 3.81 (s, 3H), 3.73 (s, 3H); $^{13}$C NMR (100 MHz, CDCl$_3$): δ 154.3, 141.8, 137.2, 111.2, 101.9, 101.8, 56.0, 55.4. Spectral data is in accordance with the literature report (Markiewicz, et al., 2010).

u.

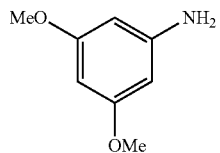

3,5-Dimethoxyaniline

Method A, T=−78° C., t=2 h; Yield=78%; $R_f$=0.25 (Hexanes:EtOAc=4:1); $^1$H NMR (400 MHz, CDCl$_3$): δ 5.93 (t, J=2.0 Hz, 1H), 5.87 (d, J=2.4 Hz, 2H), 3.73 (s, 6H), 3.67 (s, 2H); $^{13}$C NMR (100 MHz, CDCl$_3$): δ 161.5, 148.4, 93.6, 90.7, 55.0. Spectral data is in accordance with the literature report (Fan, et al., 2015).

v.

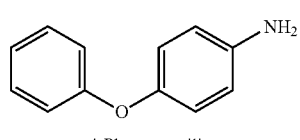

4-Phenoxyaniline

Method A, T=−78° C., t=2 h; Yield=81%; $R_f$=0.50 (Hexanes:EtOAc=3:1); $^1$H NMR (600 MHz, CDCl$_3$): δ 7.35-7.28

(m, 2H), 7.04 (t, J=7.4 Hz, 1H), 6.96 (d, J=8.0 Hz, 2H), 6.90 (d, J=8.7 Hz, 2H), 6.69 (d, J=8.7 Hz, 2H), 3.59 (br s, 2H); $^{13}$C NMR (151 MHz, CDCl$_3$): δ 158.8, 148.5, 142.6, 129.5, 122.0, 121.0, 117.2, 116.2. Spectral data is in accordance with the literature report (Lee, et al., 2001).

w.

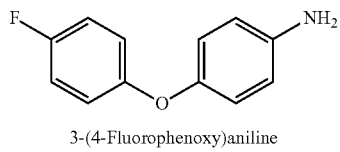

3-(4-Fluorophenoxy)aniline (23w)

Method A, T=−78° C., t=2 h; Yield=70%; R$_f$=0.6 (Hexanes:EtOAc=3:1); $^1$H NMR (600 MHz, CDCl$_3$): δ 7.09 (t, J=8.4 Hz, 1H), 7.07-6.95 (m, 4H), 6.43 (dd, J=8.0, 1.8 Hz, 1H), 6.36 (dd, J=8.4, 1.8 Hz, 1H), 6.31 (d, J=2.4 Hz, 1H), 3.76 (br s, 2H); $^{13}$C NMR (151 MHz, CDCl$_3$): δ 159.6, 158.8, 158.0, 147.6, 130.4, 120.7, 120.6, 116.2, 116.1, 110.1, 108.4, 105.0. Spectral data is in accordance with the literature report (Maiti, et al., 2009).

x.

3-(Benzyloxy)aniline (23x)

Method A, T=−78° C., t=2 h; Yield=86%; R$_f$=0.40 (Hexanes:EtOAc=3:1); $^1$H NMR (600 MHz, CDCl$_3$): δ 7.45 (d, J=6.6 Hz, 2H), 7.40 (t, J=7.8 Hz, 2H), 7.34 (t, J=7.2 Hz, 1H), 7.09 (t, J=7.8 Hz, 1H), 6.43 (dd, J=7.8, 2.4 Hz, 1H), 6.38-6.30 (m, 2H), 5.04 (s, 2H), 3.72 (br s, 2H); $^{13}$C NMR (151 MHz, CDCl$_3$): δ 160.0, 147.6, 137.2, 130.1, 128.5, 127.8, 127.4, 108.2, 104.9, 102.0, 69.8. Spectral data is in accordance with the literature report (Lundgren, et al., 2010).

y.

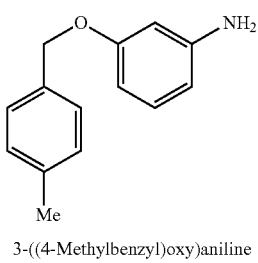

3-((4-Methylbenzyl)oxy)aniline (23y)

Method A, T=−78° C., t=2 h; Yield=65%; R$_f$=0.55 (Hexanes:EtOAc=3:1); $^1$H NMR (600 MHz, CDCl$_3$): δ 7.33 (d, J=6.6 Hz, 2H), 7.20 (d, J=7.8 Hz, 2H), 7.08 (t, J=8.4 Hz, 1H), 6.45-6.40 (m, 1H), 6.37-6.29 (m, 2H), 4.99 (s, 2H), 3.73 (br s, 2H), 2.38 (s, 3H); $^{13}$C NMR (151 MHz, CDCl$_3$): δ 160.0, 147.5, 137.6, 134.1, 130.1, 129.2, 127.5, 108.2, 105.0, 102.1, 69.7, 21.2. Spectral data is in accordance with the literature report (Kumaran and Leong, 2015)

z.

4-(Trifluoromethyoxy)aniline (23z)

Method A, T=−20° C., t=2 h; Yield=62%; R$_f$=0.70 (Hexanes:EtOAc=3:1); $^1$H NMR (600 MHz, CDCl$_3$): δ 7.01 (d, J=8.4 Hz, 2H), 6.67-6.60 (m, 2H), 3.68 (br s, 2H); $^{13}$C NMR (151 MHz, CDCl$_3$): δ 145.2, 141.3, 122.4, 120.64 (q, J=255.3 Hz), 115.4. Spectral data is in accordance with the literature report (Feiring, 1979).

aa.

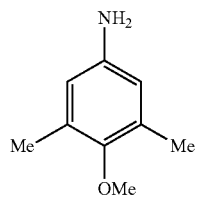

4-Methoxy-3,5-dimethylaniline (24a)

Method A, T=−78° C., t=2 h; Yield=77%; R$_f$=0.25 (Hexanes:EtOAc=4:1); $^1$H NMR (400 MHz, CDCl$_3$): δ 6.37 (s, 2H), 3.68 (s, 3H), 3.51 (br s, 2H), 2.23 (s, 6H); $^{13}$C NMR (100 MHz, CDCl$_3$): δ 149.5, 141.9, 131.3, 115.2, 59.8, 15.9. Spectral data is in accordance with the literature report (Cheemala, et al., 2007).

bb.

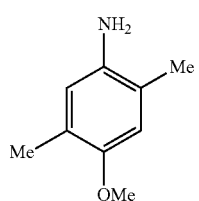

4-Methoxy-2,5-dimethylaniline (24b)

Method A, T=−45° C., t=2 h; Yield=46%; R$_f$=0.35 (Hexanes:EtOAc=4:1); $^1$H NMR (400 MHz, CDCl$_3$): δ 6.61 (s, 1H), 6.52 (s, 1H), 3.78 (s, 3H), 3.29 (br s, 2H), 2.17 (s, 6H); $^{13}$C NMR (100 MHz, CDCl$_3$): δ 150.7, 137.6, 124.9, 120.3, 118.1, 113.3, 56.0, 17.3, 15.7. Spectral data is in accordance with the literature report (Hartz, et al., 2009)

cc.

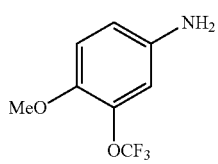

4-Methoxy-3-(trifluoromethoxy)aniline (24c)

Method A, T=−78° C., t=2 h; Yield=65%; $R_f$=0.35 (Hexanes:EtOAc=2:1); $^1$H NMR (600 MHz, CDCl$_3$): δ 6.89 (d, J=3.0 Hz, 1H), 6.84 (d, J=9.0 Hz, 1H), 6.81-6.76 (m, 1H), 3.81 (s, 3H), 3.50 (br s, 2H); $^{13}$C NMR (150 MHz, CDCl$_3$): δ 150.2, 139.6, 123.6 (q, J=270.2 Hz), 119.3, 119.2 (q, J=30.6 Hz), 114.0, 113.8 (q, J=4.4 Hz), 56.5. Spectral data is in accordance with the literature report.

dd.

4-Chloroaniline (24d)

Method A, T=−78° C., t=2 h; Yield=43%; $R_f$=0.40 (Hexanes:EtOAc=4:1); $^1$H NMR (400 MHz, CDCl$_3$): δ 7.10 (d, J=8.8 Hz, 2H), 6.60 (d, J=8.8 Hz, 2H), 3.58 (br s, 2H); $^{13}$C NMR (100 MHz, CDCl$_3$): δ 144.9, 129.0, 123.0, 116.2. Spectral data is in accordance with the literature report (Markiewicz, et al., 2010)

ee.

3-Chloroaniline (24e)

Method A, T=−78° C., t=2 h; Yield=63%; $R_f$=0.40 (Hexanes:EtOAc=4:1); $^1$H NMR (400 MHz, CDCl$_3$): δ 7.07 (t, J=8.0 Hz, 1H), 6.77-6.71 (m, 1H), 6.67 (t, J=2.0 Hz, 1H), 6.57-6.51 (m, 1H), 3.72 (br s, 2H); $^{13}$C NMR (100 MHz, CDCl$_3$): δ 147.6, 134.7, 130.2, 118.3, 114.8, 113.1. Spectral data is in accordance with the literature report (Xu and Wolf, 2009).

ff.

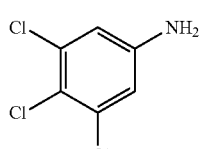

3,4,5-Trichloroaniline (24f)

Method A, T=−45° C., t=2 h; Yield=47%; $R_f$=0.35 (Hexanes:EtOAc=4:1); $^1$H NMR (400 MHz, CDCl$_3$): δ 6.67 (s, 2H), 3.78 (br s, 2H); $^{13}$C NMR (100 MHz, CDCl$_3$): δ 145.6, 134.1, 119.7, 115.0. Spectral data is in accordance with the literature report (Garcia, et al., 2012).

gg.

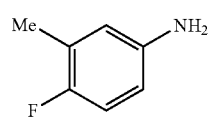

4-Fluoro-3-methylaniline (24g)

Method A, T=−78° C., t=2 h; Yield=48%; $R_f$=0.40 (Hexanes:EtOAc=4:1); $^1$H NMR (400 MHz, CDCl$_3$): δ 6.80 (t, J=8.8 Hz, 1H), 6.52-6.40 (m, 2H), 3.44 (br s, 2H), 2.20 (d, J=1.6 Hz, 3H); $^{13}$C NMR (100 MHz, CDCl$_3$): δ 147.6, 134.7, 130.2, 118.3, 114.8, 113.1. Spectral data is in accordance with the literature report (Tordeux and Wakselman, 1995).

hh.

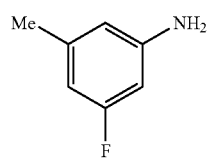

3-Fluoro-5-methylaniline (24h)

Method A, T=−45° C., t=2 h; Yield=62%; $R_f$=0.35 (Hexanes:EtOAc=3:1); $^1$H NMR (600 MHz, CDCl$_3$): δ 6.32-6.25 (m, 2H), 6.20 (d, J=10.2 Hz, 1H), 3.68 (br s, 2H), 2.25 (s, 3H); $^{13}$C NMR (151 MHz, CDCl$_3$): δ 163.8 (d, J=242.2 Hz), 147.8 (d, J=11.0 Hz), 141.0 (d, J=10.0 Hz), 111.3, 105.9 (d, J=19.8 Hz), 99.2 (d, J=24.3 Hz), 21.4.

ii.

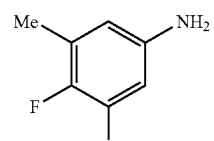

4-Fluoro-3,5-dimethylaniline (24i)

Method A, T=−45° C., t=2 h; Yield=69%; $R_f$=0.25 (Hexanes:EtOAc=4:1); $^1$H NMR (600 MHz, CDCl$_3$): δ 6.33 (s, 1H), 6.32 (s, 1H), 3.34 (br s, 2H), 2.19 (s, 3H), 2.18 (s, 3H); $^{13}$C NMR (151 MHz, CDCl$_3$): δ 153.6 (d, J=233.3 Hz), 141.5 (d, J=3.3 Hz), 124.8 (d, J=18.7 Hz), 115.1 (d, J=3.3 Hz), 14.62, 14.59.

jj.

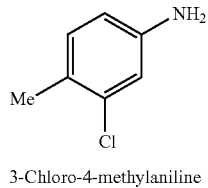

3-Chloro-4-methylaniline

Method A, T=−45° C., t=2 h; Yield=67%; $R_f$=0.30 (Hexanes:EtOAc=4:1); $^1$H NMR (600 MHz, CDCl$_3$): δ 6.99 (d, J=7.8 Hz, 1H), 6.71 (d, J=2.4 Hz, 1H), 6.49 (dd, J=7.8, 2.4 Hz, 1H), 3.59 (br s, 2H), 2.26 (s, 3H); $^{13}$C NMR (151 MHz, CDCl$_3$): δ 145.3, 134.6, 131.3, 125.4, 115.5, 113.6, 18.9. Spectral data is in accordance with the literature report (Ahammed, et al., 2011).

kk.

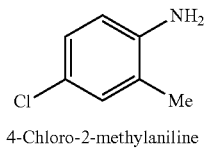

4-Chloro-2-methylaniline

Method A, T=−45° C., t=2 h; Yield=46%; $R_f$=0.35 (Hexanes:EtOAc=4:1); $^1$H NMR (400 MHz, CDCl$_3$): δ 7.03 (d, J=2.4 Hz, 1H), 6.99 (dd, J=8.4, 2.4 Hz, 1H), 6.58 (d, J=8.4 Hz, 1H), 3.56 (br s, 2H), 2.13 (s, 3H); $^{13}$C NMR (100 MHz, CDCl$_3$): δ 143.1, 129.9, 126.5, 123.9, 122.7, 115.8, 17.2. Spectral data is in accordance with the literature report (Zhu, et al., 2012)

ll.

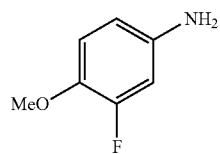

3-Fluoro-4-methoxylaniline

Method A, T=−78° C., t=2 h; Yield=68%; $R_f$=0.35 (Hexanes:EtOAc=2:1); $^1$H NMR (600 MHz, CDCl3): δ 6.78 (t, J=9.0 Hz, 1H), 6.45 (dd, J=13.2, 3.0 Hz, 1H), 6.39-6.34 (m, 1H), 3.79 (s, 3H), 3.49 (br s, 2H); $^{13}$C NMR (151 MHz, CDCl$_3$): δ 153.1 (d, J=244.5 Hz), 141.0 (d, J=8.9 Hz), 140.1 (d, J=12.1 Hz), 115.7 (d, J=3.3 Hz), 110.2 (d, J=3.3 Hz), 104.1 (d, J=20.8 Hz), 57.3. Spectral data is in accordance with the literature report (Blair, et al., 2000).

mm.

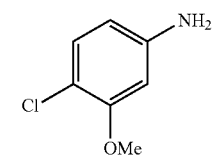

4-Chloro-3-methoxyaniline

Method A, T=−78° C., t=3 h; Yield=62%; $R_f$=0.30 (Hexanes:EtOAc=4:1); $^1$H NMR (400 MHz, CDCl$_3$): δ 7.08 (d, J=8.4 Hz, 1H), 6.25 (d, J=2.4 Hz, 1H), 6.23-6.17 (m, 1H), 3.81 (s, 3H), 3.69 (br s, 2H); $^{13}$C NMR (100 MHz, CDCl$_3$): δ 155.4, 146.4, 130.3, 111.2, 107.7, 99.6, 55.8. Spectral data is in accordance with the literature report (Cross, et al., 2010).

nn.

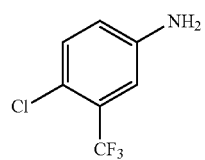

4-Chloro-3-(trifluoromethyl)aniline

Method A, T=−45° C., t=2 h; Yield=61%; $R_f$=0.30 (Hexanes:EtOAc=4:1); $^1$H NMR (400 MHz, CDCl$_3$): δ 7.22 (d, J=8.8 Hz, 1H), 6.95 (d, J=2.8 Hz, 1H), 6.74-6.69 (m, 1H), 3.84 (br s, 2H); $^{13}$C NMR (100 MHz, CDCl$_3$): δ 145.1, 132.0, 128.6 (q, J=30.6 Hz), 122.8 (q, J=271.6 Hz), 120.1, 118.6, 113.6 (q, J=5.1 Hz); $^{19}$F NMR (376 MHz, CDCl$_3$): δ −62.8. Spectral data is in accordance with the literature report (Fan, et al., 2015).

oo.

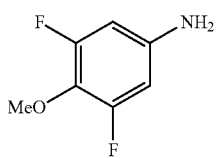

3,5-Difluoro-4-methoxyaniline

Method A, T=−45° C., t=2 h; Yield=61%; $R_f$=0.30 (Hexanes:EtOAc=4:1); $^1$H NMR (600 MHz, CDCl$_3$): δ 6.24-6.14 (m, 2H), 3.85 (s, 3H), 3.68 (br s, 2H); $^{13}$C NMR (151 MHz, CDCl$_3$): δ 155.6 (dd, J=245.5, 8.8 Hz), 142.6 (t, J=12.1 Hz), 128.3 (t, J=15.4 Hz), (98.79, 98.77, 98.74, 98.64, 98.61, 98.59), 62.2 (t, J=3.3 Hz). Spectral data is in accordance with the literature report (Qin, et al., 1999).

pp.

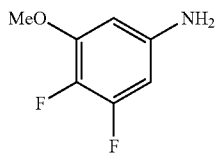

3,4-Difluoro-5-methoxyaniline

Method A, T=−45° C., t=2 h; Yield=77%; $R_f$=0.30 (Hexanes:EtOAc=4:1); $^1$H NMR (600 MHz, CDCl$_3$): δ 6.10-6.01 (m, 2H), 3.83 (s, 3H), 3.60 (br s, 2H); $^{13}$C NMR (151 MHz, CDCl$_3$): δ 152.4, 152.3, 150.8, 150.7, 149.5, 149.5, 149.4, 149.4, 142.3, 142.2, 135.5, 135.4, 133.9, 133.8, 95.8, 95.4, 95.3, 56.4. Spectral data is in accordance with the literature report (Van Brandt, et al., 2012).

qq.

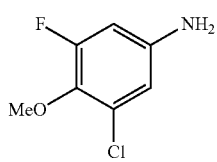

3-Chloro-5-fluoro-4-methoxyaniline

Method A, T=−45° C., t=2 h; Yield=60%; $R_f$=0.30 (Hexanes:EtOAc=4:1); $^1$H NMR (600 MHz, CDCl$_3$): δ 6.45 (t, J=2.3 Hz, 1H), 6.33 (dd, J=12.0, 2.7 Hz, 1H), 3.83 (s, 3H), 3.64 (br s, 2H); $^{13}$C NMR (151 MHz, CDCl$_3$): δ 156.8 (d, J=247.8 Hz), 143.0 (d, J=11.0 Hz), 136.4 (d, J=14.2 Hz), 129.0 (d, J=5.4 Hz), 111.3 (d, J=3.3 Hz), 102.3 (d, J=22.0 Hz), 61.7 (d, J=3.3 Hz).

rr.

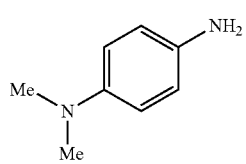

N′,N′-dimethylbenzene-1,4-diamine

Method A, T=−78° C., t=2 h; Yield=79%; $R_f$=0.20 (Hexanes:EtOAc=1:1); $^1$H NMR (600 MHz, Acetone-d$_6$): δ 6.68-6.62 (m, 2H), 6.61-6.55 (m, 2H), 4.02 (br s, 2H), 2.76 (s, 6H); $^{13}$C NMR (151 MHz, Acetone-d$_6$): δ 143.9, 140.0, 115.6, 115.5, 41.5. Spectral data is in accordance with the literature report (Green and Hartwig, 2014).

ss.

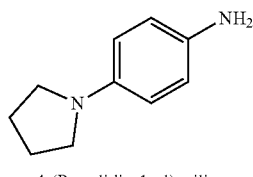

4-(Pyrrolidin-1-yl)aniline

Method A, T=−78° C., t=2 h; Yield=57%; $R_f$=0.25 (Hexanes:EtOAc=1:1); $^1$H NMR (600 MHz, Acetone-d$_6$): δ 6.64-6.53 (m, 2H), 6.45-6.38 (m, 2H), 3.87 (br s, 2H), 3.26-3.11 (m, 4H), 2.03-1.90 (m, 4H); $^{13}$C NMR (151 MHz, Acetone-d$_6$): δ 141.6, 138.3, 116.1, 113.0, 48.1, 24.9. Spectral data is in accordance with the literature report (Irie, et al., 2009).

tt.

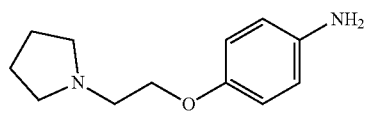

4-(2-(Pyrrolidin-1-yl)ethoxy)aniline

Method A, T=−78° C., t=2 h; Yield=83%; $R_f$=0.2 (5% MeOH in DCM); $^1$H NMR (600 MHz, CDCl$_3$): δ 6.78-6.68 (m, 2H), 6.67-6.55 (m, 2H), 4.18-3.92 (m, 2H), 3.43 (br s, 2H), 2.98-2.77 (m, 2H), 2.75-2.53 (m, 4H), 1.88-1.71 (m, 4H); $^{13}$C NMR (151 MHz, CDCl$_3$): δ 152.0, 140.0, 116.3, 115.8, 67.6, 55.2, 54.7, 23.5. Spectral data is in accordance with the literature report (Guagnano, et al., 2011).

uu.

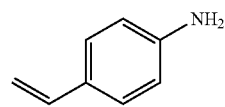

4-Vinylaniline

Method A, T=−78° C., t=2 h; Yield=75%; $R_f$=0.20 (Hexanes:EtOAc=5:1); $^1$H NMR (400 MHz, CDCl$_3$): δ 7.30-7.26 (m, 2H), 6.72-6.63 (m, 3H), 5.61 (dd, J=17.6, 1.2 Hz, 1H), 5.10 (dd, J=10.8, 1.2 Hz, 1H), 3.70 (br s, 2H); $^{13}$C NMR (100 MHz, CDCl$_3$): δ 146.1, 136.5, 128.2, 127.2, 114.9, 109.9. Spectral data is in accordance with the literature report (Cheung, et al., 2013).

vv.

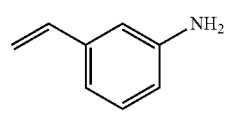

3-Vinylaniline

Method A, T=−78° C., t=2 h; Yield=72%; $R_f$=0.20 (Hexanes:EtOAc=5:1); $^1$H NMR (400 MHz, CDCl$_3$): δ 7.16 (t, J=8.0 Hz, 1H), 6.87 (d, J=7.6 Hz, 1H), 6.76 (t, J=2.0 Hz, 1H), 6.73-6.59 (m, 2H), 5.74 (dd, J=17.6, 1.2 Hz, 1H), 5.25 (dd, J=11.2, 0.8 Hz, 1H), 3.63 (br s, 2H); $^{13}$C NMR (100 MHz, CDCl$_3$): δ 146.5, 138.5, 136.9, 129.3, 116.8, 114.7, 113.5, 112.6. Spectral data is in accordance with the literature report (Fountoulaki, et al., 2014).

ww.

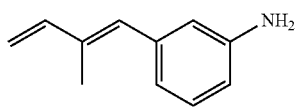

(28c)

(E)-3-(2-Methylbuta-1,3-dien-1-yl)aniline

Method A, T=−45° C., t=2 h; Yield=75%; R$_f$=0.35 (Hexanes:EtOAc=4:1); $^1$H NMR (600 MHz, CDCl$_3$): δ 7.16 (t, J=7.8 Hz, 1H), 6.75 (d, J=7.4 Hz, 1H), 6.65 (t, J=2.0 Hz, 1H), 6.62-6.51 (m, 2H), 6.47 (s, 1H), 5.32 (d, J=17.3 Hz, 1H), 5.15 (d, J=10.6 Hz, 1H), 3.65 (br s, 2H), 2.02 (d, J=1.3 Hz, 3H); $^{13}$C NMR (151 MHz, CDCl$_3$): δ 146.0, 141.9, 138.7, 135.8, 131.8, 128.9, 119.8, 115.8, 113.6, 112.7, 13.2.

xx.

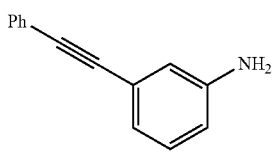

(28d)

3-(Phenylethynyl)aniline

Method A, T=−78° C., t=2 h; Yield=60%; R$_f$=0.20 (Hexanes:EtOAc=5:1); $^1$H NMR (400 MHz, CDCl$_3$): δ 7.59-7.54 (m, 2H), 7.41-7.32 (m, 3H), 7.16 (t, J=8.0 Hz, 1H), 6.99 (d, J=8.0 Hz, 1H), 6.88 (s, 1H), 6.67 (dd, J=8.0, 1.6 Hz, 1H), 3.63 (br s, 2H); $^{13}$C NMR (100 MHz, CDCl$_3$): δ 146.2, 131.5, 129.2, 128.3, 128.1, 123.8, 123.3, 122.0, 117.7, 115.3, 89.6, 88.7. Spectral data is in accordance with the literature report (Zhao, et al., 2010).

yy.

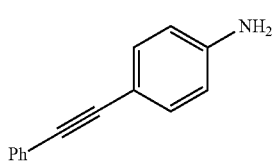

(28e)

4-(Phenylethynyl)aniline

Method A, T=−78° C., t=2 h; Yield=74%; R$_f$=0.20 (Hexanes:EtOAc=5:1); $^1$H NMR (400 MHz, CDCl$_3$): δ 7.51 (d, J=6.8 Hz, 2H), 7.38-7.27 (m, 5H), 6.64 (d, J=8.0 Hz, 2H), 3.81 (br s, 2H); $^{13}$C NMR (100 MHz, CDCl$_3$): δ 146.6, 132.9, 131.3, 128.2, 127.6, 123.9, 114.7, 112.6, 90.1, 87.3. Spectral data is in accordance with the literature report (Phetrak, et al., 2013).

zz.

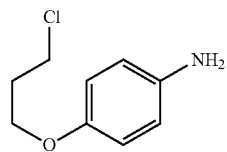

(28f)

4-(3-Chloropropoxy)aniline

Method A, T=−78° C., t=2 h; Yield=51%; R$_f$=0.20 (Hexanes:EtOAc=2:1); $^1$H NMR (600 MHz, CDCl$_3$): δ 6.80-6.71 (m, 2H), 6.69-6.62 (m, 2H), 4.04 (t, J=6.0 Hz, 2H), 3.74 (t, J=6.0 Hz, 2H), 3.47 (br s, 2H), 2.19 (p, J=6.0 Hz, 2H); $^{13}$C NMR (151 MHz, CDCl$_3$): δ 152.0, 139.9, 116.5, 115.7, 65.0, 41.6, 32.4. Spectral data is in accordance with the literature report (U.S. Pat. No. 5,104,892).

aaa.

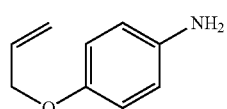

(28g)

4-(Allyloxy)aniline

Method A, T=−78° C., t=2 h; Yield=50%; R$_f$=0.30 (Hexanes:EtOAc=2:1); $^1$H NMR (600 MHz, CDCl$_3$): δ 6.80-6.70 (m, 2H), 6.66-6.60 (m, 2H), 6.12-5.98 (m, 1H), 5.44-5.35 (m, 1H), 5.30-5.20 (m, 1H), 4.50-4.40 (m, 2H), 3.32 (br s, 2H); $^{13}$C NMR (151 MHz, CDCl$_3$): δ 151.7, 140.1, 133.8, 117.3, 116.3, 115.9, 69.6. Spectral data is in accordance with the literature report (Green and Hartwig, 2014).

bbb.

(28h)

4-(Cyclopropylmethoxy)aniline

Method A, T=−78° C., t=2 h; Yield=51%; R$_f$=0.20 (Hexanes:EtOAc=2:1); $^1$H NMR (600 MHz, CDCl$_3$): δ 6.75 (dd, J=6.6, 1.8 Hz, 2H), 6.63 (dd, J=6.6, 2.4 Hz, 2H), 3.72 (d, J=6.6 Hz, 2H), 3.38 (br s, 2H), 1.27-1.17 (m, 1H), 0.67-0.56 (m, 2H), 0.40-0.24 (m, 2H); $^{13}$C NMR (151 MHz, CDCl$_3$): δ 152.2, 139.8, 116.4, 115.8, 73.5, 10.4, 3.1. Spectral data is in accordance with the literature report (Lau, et al., 2007).

ccc.

(28i)

4-(Cyclobutylmethoxy)aniline

Method A, T=−78° C., t=2 h; Yield=58%; $R_f$=0.25 (Hexanes:EtOAc=2:1); $^1$H NMR (600 MHz, CDCl$_3$): δ 6.75 (d, J=8.4 Hz, 2H), 6.64 (d, J=8.4 Hz, 2H), 3.86 (d, J=6.6 Hz, 2H), 3.37 (br s, 2H), 2.73 (p, J=7.2 Hz, 1H), 2.13 (dtd, J=12.6, 8.4, 4.2 Hz, 2H), 2.04-1.76 (m, 4H); $^{13}$C NMR (151 MHz, CDCl$_3$): δ 152.5, 139.6, 116.4, 116.4, 115.8, 73.0, 34.8, 24.9, 18.6. Spectral data is in accordance with the literature report (US Patent Publication No. 2010/0190747).

ddd.

2,3-Dihydrobenzofuran-5-amine (28j)

Method A, T=−78° C., t=2 h; Yield=45%; $R_f$=0.35 (Hexanes:EtOAc=3:1); $^1$H NMR (600 MHz, CDCl$_3$): δ 6.65-6.56 (m, 2H), 6.46 (dd, J=8.4, 2.4 Hz, 1H), 4.49 (t, J=8.4 Hz, 2H), 3.37 (br s, 2H), 3.12 (t, J=8.4 Hz, 2H); $^{13}$C NMR (151 MHz, CDCl$_3$): δ 153.1, 139.8, 127.7, 114.6, 112.6, 109.2, 70.8, 30.2. Spectral data is in accordance with the literature report (Patel, et al., 2014).

eee.

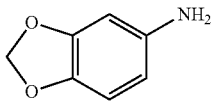

Benzo[d][1,3]dioxol-5-amine (28k)

Method A, T=−78° C., t=2 h; Yield=66%; $R_f$=0.35 (Hexanes:EtOAc=4:1); $^1$H NMR (400 MHz, CDCl$_3$): δ 6.62 (d, J=8.4 Hz, 1H), 6.28 (d, J=2.4 Hz, 1H), 6.11 (dd, J=8.0, 2.0 Hz, 1H), 5.84 (s, 2H), 3.46 (br s, 2H); $^{13}$C NMR (100 MHz, CDCl$_3$): δ 148.0, 141.3, 140.1, 108.4, 106.7, 100.5, 97.9. Spectral data is in accordance with the literature report (Fan, et al., 2015).

fff.

2,2-Difluorobenzo[d][1,3]dioxol-5-amine (28l)

Method A, T=−78° C., t=2 h; Yield=27%; $R_f$=0.40 (Hexanes:EtOAc=3:1); $^1$H NMR (600 MHz, CDCl$_3$): δ 6.81 (d, J=8.4 Hz, 1H), 6.43 (d, J=2.4 Hz, 1H), 6.32 (dd, J=8.4, 2.4 Hz, 1H), 3.58 (br s, 2H); $^{13}$C NMR (151 MHz, CDCl$_3$): δ 144.4, 143.0, 136.6, 133.4, 131.7, 130.0, 109.7, 108.8, 97.7. Spectral data is in accordance with the literature report (Hagooly and Rozen, et al., 2008).

ggg.

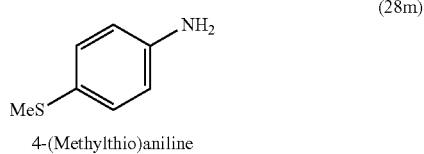

4-(Methylthio)aniline (28m)

Method A, T=−78° C., t=2 h; Yield=54%; $R_f$=0.35 (Hexanes:EtOAc=4:1); $^1$H NMR (400 MHz, CDCl$_3$): δ 7.21-7.15 (m, 2H), 6.66-6.60 (m, 2H), 3.67 (br s, 2H), 2.41 (s, 3H); $^{13}$C NMR (100 MHz, CDCl$_3$): δ 145.0, 130.9, 125.6, 115.6, 18.7. Spectral data is in accordance with the literature report (Fan, et al., 2015).

hhh.

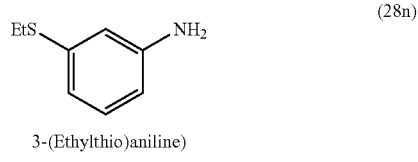

3-(Ethylthio)aniline (28n)

Method A, T=−78° C., t=2 h; Yield=61%; $R_f$=0.30 (Hexanes:EtOAc=4:1); $^1$H NMR (600 MHz, CDCl$_3$): δ 7.06 (t, J=7.8 Hz, 1H), 6.82-6.68 (m, 1H), 6.66 (t, J=2.4 Hz, 1H), 6.49 (ddd, J=7.8, 2.4, 0.6 Hz, 1H), 3.56 (br s, 2H), 2.92 (q, J=7.8 Hz, 2H), 1.31 (t, J=7.4 Hz, 3H); $^{13}$C NMR (151 MHz, CDCl$_3$): δ 146.7, 137.5, 129.6, 118.9, 115.2, 112.7, 27.3, 14.4. Spectral data is in accordance with the literature report (EP 2336107).

iii.

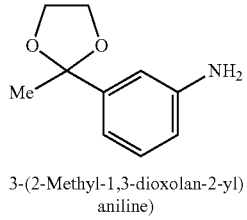

3-(2-Methyl-1,3-dioxolan-2-yl)aniline (28o)

Method A, T=−78° C., t=2 h; Yield=80%; $R_f$=0.30 (Hexanes:EtOAc=3:1); $^1$H NMR (600 MHz, CDCl$_3$): δ 7.12 (t, J=7.8 Hz, 1H), 6.92-6.85 (m, 1H), 6.82 (t, J=2.4 Hz, 1H), 6.61 (dd, J=7.8, 2.4 Hz, 1H), 4.06-3.96 (m, 2H), 3.83-3.74 (m, 2H), 3.69 (br s, 2H), 1.64 (s, 3H); $^{13}$C NMR (151 MHz, CDCl$_3$): δ 146.2, 144.5, 129.1, 115.5, 114.4, 112.0, 108.7, 64.3, 27.5. Spectral data is in accordance with the literature report (Petersen, 1999).

jjj.

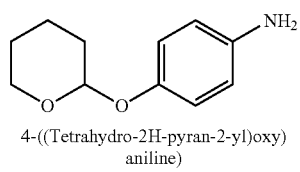

4-((Tetrahydro-2H-pyran-2-yl)oxy)aniline (28p)

Method A, T=−78° C., t=2 h; Yield=67%; R$_f$=0.25 (Hexanes:EtOAc=3:1); $^1$H NMR (600 MHz, CDCl$_3$): δ 6.89 (d, J=9.0 Hz, 2H), 6.62 (d, J=9.0 Hz, 2H), 5.24 (t, J=3.0 Hz, 1H), 4.00-3.90 (m, 1H), 3.62-3.55 (m, 1H), 3.54 (br s, 2H), 2.02-1.95 (m, 1H), 1.91-1.80 (m, 2H), 1.70-1.50 (m, 3H); $^{13}$C NMR (151 MHz, CDCl$_3$): δ 150.0, 140.6, 117.9, 116.2, 97.4, 62.0, 30.4, 25.2, 18.9. Spectral data is in accordance with the literature report (Surry and Buchwald, 2007).

kkk.

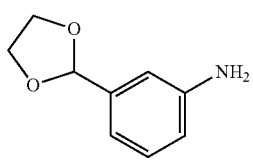

3-(1,3-Dioxolan-2-yl)aniline (28q)

Method A, T=−78° C., t=2 h; Yield=79%; R$_f$=0.30 (Hexanes:EtOAc=1:1); $^1$H NMR (600 MHz, CDCl$_3$): δ 7.16 (t, J=7.8 Hz, 1H), 6.87 (d, J=7.2 Hz, 1H), 6.81 (t, J=1.8 Hz, 1H), 6.70-6.60 (m, 1H), 5.74 (s, 1H), 4.18-4.06 (m, 2H), 4.05-3.95 (m, 2H), 3.57 (br s, 2H); $^{13}$C NMR (151 MHz, CDCl$_3$): δ 146.4, 139.0, 129.3, 116.6, 115.9, 112.8, 103.6, 65.2. Spectral data is in accordance with the literature report (Lee, et al. 2001).

lll.

2-Bromoaniline (28r)

Method B. Yield=29%; R$_f$=0.40 (Hexanes:EtOAc=5:1); $^1$H NMR (600 MHz, CDCl$_3$): δ 7.41 (dd, J=7.8, 1.2 Hz, 1H), 7.20-7.04 (m, 1H), 6.77 (d, J=8.4 Hz, 1H), 6.63 (td, J=7.2, 1.2 Hz, 1H), 4.01 (br s, 2H); $^{13}$C NMR (151 MHz, CDCl$_3$): δ 144.0, 132.5, 128.3, 119.4, 115.7, 109.3. Spectral data is in accordance with the literature report (Zhu, et al., 2012).

mmm.

3-Bromoaniline (28s)

Method B. Yield=76%; R$_f$=0.35 (Hexanes:EtOAc=3:1); $^1$H NMR (600 MHz, CDCl$_3$): δ 7.00 (t, J=7.8 Hz, 1H), 6.87 (d, J=7.8 Hz, 1H), 6.83 (s, 1H), 6.59 (dd, J=7.8, 1.2 Hz, 1H), 3.69 (br s, 2H); $^{13}$C NMR (151 MHz, CDCl$_3$): δ 147.8, 130.6, 123.0, 121.3, 117.8, 113.6. Spectral data is in accordance with the literature report (Lee, et al., 2001).

nnn.

4-Bromoaniline (28t)

Method B. Yield=77%; R$_f$=0.35 (Hexanes:EtOAc=3:1); $^1$H NMR (600 MHz, CDCl$_3$): δ 7.23 (d, J=8.4 Hz, 2H), 6.55 (d, J=9.0 Hz, 2H), 3.59 (br s, 2H); $^{13}$C NMR (151 MHz, CDCl$_3$): δ 145.4, 131.9, 116.6, 110.1. Spectral data is in accordance with the literature report (Lee, et al., 2001).

ooo.

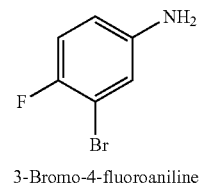

3-Bromo-4-fluoroaniline (28u)

Method B. Yield=63%; R$_f$=0.30 (Hexanes:EtOAc=4:1); $^1$H NMR (600 MHz, CDCl$_3$): δ 6.89 (t, J=8.4 Hz, 1H), 6.86-6.81 (m, 1H), 6.59-6.50 (m, 1H), 3.58 (br s, 2H); $^{13}$C NMR (151 MHz, CDCl$_3$): δ 152.5 (d, J=236.6 Hz), 143.4, 119.1, 116.6 (d, J=23.1 Hz), 115.0 (d, J=6.6 Hz), 108.9 (d, J=22.0 Hz). Spectral data is in accordance with the literature report (Austin, et al., 1981).

ppp.

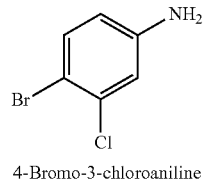

4-Bromo-3-chloroaniline (28v)

Method B Yield=77%; R$_f$=0.30 (Hexanes:EtOAc=4:1); $^1$H NMR (600 MHz, CDCl$_3$): δ 7.30 (d, J=8.4 Hz, 1H), 6.76 (d, J=3.0 Hz, 1H), 6.43 (dd, J=8.4, 2.4 Hz, 1H), 3.74 (br s, 2H); $^{13}$C NMR (151 MHz, CDCl$_3$): δ 146.6, 134.5, 133.8, 116.3, 114.9, 109.6. Spectral data is in accordance with the literature report (Fattori, et al., 2009).

qqq.

4-Aminophenyl
4-methylbenzenesulfonate (28w)

Method A, T=−30° C., t=2 h; Yield=48%; R$_f$=0.25 (Hexanes:EtOAc=2:1); $^1$H NMR (600 MHz, CDCl$_3$): δ 7.67 (d, J=8.4 Hz, 2H), 7.28 (d, J=7.8 Hz, 2H), 6.71 (dd, J=6.6, 1.8 Hz, 2H), 6.54-6.47 (m, 2H), 3.68 (br s, 2H), 2.43 (s, 3H); $^{13}$C NMR (151 MHz, CDCl$_3$): δ 145.4, 145.0, 141.5, 132.4, 129.6, 128.5, 123.1, 115.3, 21.6. Spectral data is in accordance with the literature report (Bahrami, et al., 2012).

rrr.

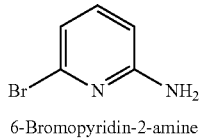

(28x)

6-Bromopyridin-2-amine

Method D. Yield=32%; R$_f$=0.35 (Hexanes:EtOAc=2:1); $^1$H NMR (600 MHz, DMSO-d$_6$) δ 7.26 (d, J=7.7 Hz, 1H), 6.62 (d, J=7.4 Hz, 1H), 6.40 (d, J=8.1 Hz, 1H), 6.37 (s, 2H); $^{13}$C NMR (151 MHz, DMSO-d$_6$) δ 160.7, 140.3, 139.9, 114.5, 107.1. Spectral data is in accordance with the literature report (Zhang, et al., 2009).

sss.

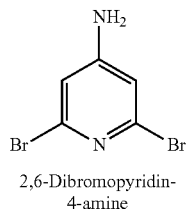

(28y)

2,6-Dibromopyridin-4-amine

Method C, T$_1$=25° C., t$_1$=6 min., T$_2$=−25° C., t$_2$=2 h; Yield=58%; R$_f$=0.30 (Hexanes:EtOAc=2:1); $^1$H NMR (600 MHz, CDCl$_3$): δ 6.67 (s, 2H), 4.33 (br s, 2H); $^{13}$C NMR (151 MHz, CDCl$_3$): δ 155.4, 140.9, 112.0. Spectral data is in accordance with the literature report (Hay, et al., 2011).

ttt.

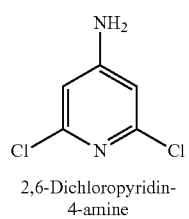

(28z)

2,6-Dichloropyridin-4-amine

Method C, T$_1$=25° C., t$_1$=6 min., T$_2$=−25° C., t$_2$=2 h; Yield=64%; R$_f$=0.2 (Hexanes:EtOAc=3:1); $^1$H NMR (600 MHz, DMSO-d$_6$) δ 6.76 (br s, 2H), 6.50 (s, 2H); $^{13}$C NMR (151 MHz, DMSO-d$_6$) δ 159.1, 149.7, 107.0. Spectral data is in accordance with the literature report (Altenbach, et al., 2008).

uuu.

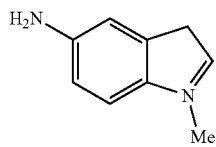

(29a)

1-Methyl-1H-indol-5-amine

Method B. Yield=55%; R$_f$=0.30 (Hexanes:EtOAc=2:1); $^1$H NMR (400 MHz, CDCl$_3$): δ 7.18 (d, J=8.8 Hz, 1H), 7.03-6.96 (m, 2H), 6.74 (dd, J=8.8, 2.4 Hz, 1H), 6.37 (d, J=3.2 Hz, 1H), 3.74 (s, 3H), 3.47 (s, 2H); $^{13}$C NMR (100 MHz, CDCl$_3$): δ 139.1, 131.7, 129.2, 129.0, 112.3, 109.6, 105.5, 99.3, 32.6. Spectral data is in accordance with the literature report (Gasparotto, et al., 2007).

vvv.

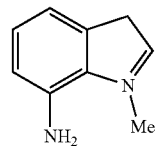

(29b)

1-Methyl-1H-indol-7-amine

Method B. Yield=22%; R$_f$=0.30 (Hexanes:EtOAc=2:1); $^1$H NMR (400 MHz, CDCl$_3$): δ 7.18-7.14 (m, 1H), 6.95-6.88 (m, 2H), 6.49 (dd, J=7.2, 0.8 Hz, 1H), 6.42 (d, J=3.2 Hz, 1H), 4.10 (s, 3H), 3.66 (s, 2H); $^{13}$C NMR (100 MHz, CDCl$_3$): δ 132.6, 130.9, 130.2, 127.3, 120.2, 113.1, 109.7, 101.1, 36.2.

www.

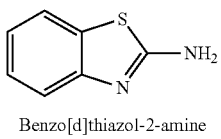

(29c)

Benzo[d]thiazol-2-amine

Method D, T$_1$=0° C., t$_1$=6 min., T$_2$=−30° C., t$_2$=2 h; Yield=26%; R$_f$=0.30 (Hexanes:EtOAc=1:1); $^1$H NMR (600 MHz, CDCl$_3$): δ 7.59 (d, J=7.8 Hz, 1H), 7.54 (d, J=7.8 Hz, 1H), 7.31 (t, J=8.4 Hz, 1H), 7.13 (t, J=7.8 Hz, 1H), 5.55 (br s, 2H); $^{13}$C NMR (151 MHz, CDCl$_3$): δ 166.0, 151.8, 131.5, 126.0, 122.3, 120.9, 119.1. Spectral data is in accordance with the literature report (Cheung, et al., 2013).

xxx.

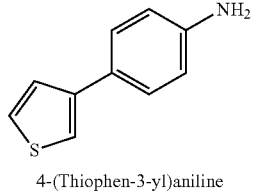

4-(Thiophen-3-yl)aniline (29d)

Method A, T=−78° C., t=2 h; Yield=42%; $R_f$=0.30 (Hexanes:EtOAc=3:1); $^1$H NMR (400 MHz, CDCl$_3$): δ 7.46-7.41 (m, 2H), 7.38-7.34 (m, 2H), 7.33-7.30 (m, 1H), 6.72 (dd, J=6.4, 2.4 Hz, 2H), 3.70 (s, 2H); $^{13}$C NMR (100 MHz, CDCl$_3$): δ 145.5, 142.3, 127.4, 126.6, 126.1, 125.8, 118.0, 115.3. Spectral data is in accordance with the literature report (Djukic, et al., 2011).

yyy.

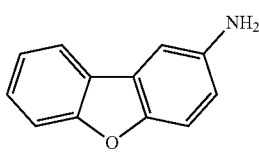

Dibenzo[b,d]furan-2-amine (29e)

Method E, T=−45° C.; Yield=36%; $R_f$=0.30 (Hexanes:EtOAc=2:1); $^1$H NMR (600 MHz, CDCl$_3$): δ 7.86 (d, J=7.2 Hz, 1H), 7.53 (d, J=8.4 Hz, 1H), 7.43 (td, J=7.2, 1.2 Hz, 1H), 7.37 (d, J=8.4 Hz, 1H), 7.30 (td, J=7.2, 0.6 Hz, 1H), 7.22 (d, J=2.4 Hz, 1H), 6.82 (dd, J=8.4, 2.4 Hz, 1H), 3.57 (br s, 2H); $^{13}$C NMR (151 MHz, CDCl$_3$): δ 156.7, 150.3, 142.0, 126.9, 124.8, 124.2, 122.2, 120.5, 115.7, 111.8, 111.6, 105.9.

zzz.

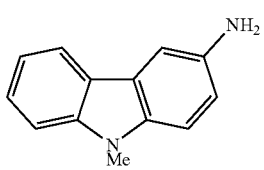

9-Methyl-9H-carbazol-3-amine (29f)

Method D. Yield=18%; $R_f$=0.30 (Hexanes:EtOAc=2:1); $^1$H NMR (600 MHz, CDCl$_3$): δ 8.00 (d, J=7.8 Hz, 1H), 7.49-7.49 (m, 2H), 7.34 (d, J=8.4 Hz, 1H), 7.22 (d, J=8.4 Hz, 1H), 7.17 (t, J=7.2 Hz, 1H), 6.93 (dd, J=8.4, 1.8 Hz, 1H), 3.79 (s, 3H), 3.31 (br s, 2H); $^{13}$C NMR (151 MHz, CDCl$_3$): δ 141.4, 138.9, 135.7, 125.5, 123.5, 122.3, 120.2, 118.1, 115.6, 108.9, 108.3, 106.2, 29.1. Spectral data is in accordance with the literature report (Dey, et al., 2014)

aaaa.

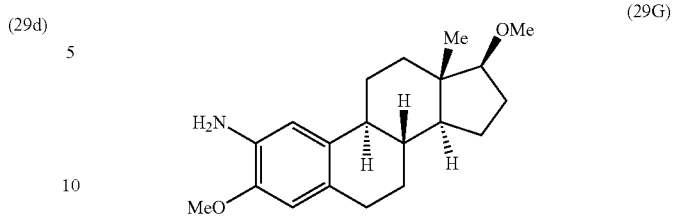

(8R,9S,13S,14S,17S)-3,17-Dimethoxy-13-methyl-7,8,9,11,12,13,14,15,16,17-decahydro-6H-cyclopenta[a]phenanthren-2-amine (29G)

Method E, T=−45° C.; Yield=25%; $R_f$=0.25 (Hexanes:EtOAc=4:1); $^1$H NMR (400 MHz, CDCl$_3$): δ 6.69 (s, 1H), 6.51 (s, 1H), 3.82 (s, 3H), 3.54 (br s, 2H), 3.38 (s, 3H), 3.31 (t, J=8.4 Hz, 1H), 2.85-2.70 (m, 2H), 2.27-2.16 (m, 1H), 2.15-2.11 (m, 1H), 2.10-2.00 (m, 2H), 1.93-1.82 (m, 1H), 1.74-1.65 (m, 1H), 1.60-1.25 (m, 6H), 1.24-1.15 (m, 1H), 0.79 (s, 3H); $^{13}$C NMR (151 MHz, CDCl$_3$): δ 145.6, 133.6, 132.5, 126.5, 112.4, 111.0, 90.8, 57.9, 55.5, 50.3, 44.0, 43.2, 38.7, 38.1, 29.2, 27.8, 27.5, 26.5, 23.0, 11.5. Spectral data is in accordance with the literature report (Hostetler, et al., 1999).

bbbb.

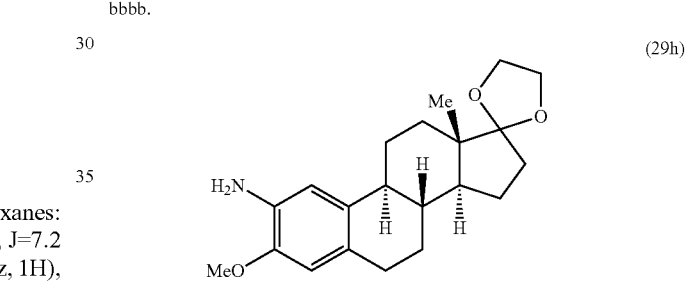

(8R,9S,13S,14S)-3-Methoxy-13-methyl-6,7,8,9,11,12,13,14,15,16-decahydrospiro[cyclopenta[a]phenanthrene-17,2'-[1,3]dioxolan]-2-amine (29h)

Method E, T=−45° C.; Yield=32%; $R_f$=0.50 (Hexanes:EtOAc=3:1); $^1$H NMR (600 MHz, CDCl$_3$): δ 6.69 (s, 1H), 6.51 (s, 1H), 4.01-3.86 (m, 4H), 3.82 (s, 3H), 3.42 (br s, 2H), 2.85-2.72 (m, 2H), 2.29-2.16 (m, 2H), 2.08-1.98 (m, 1H), 1.92-1.81 (m, 2H), 1.80-1.71 (m, 2H), 1.68-1.59 (m, 1H), 1.57-1.50 (m, 1H), 1.50-1.29 (m, 4H), 0.89 (s, 3H); $^{13}$C NMR (151 MHz, CDCl3): δ 145.6, 133.6, 132.5, 126.6, 119.4, 112.4, 111.0, 65.2, 64.5, 55.5, 49.3, 46.1, 43.7, 39.1, 34.2, 30.8, 29.2, 27.2, 26.2, 22.3, 14.3.

C. Hydroxylation of Arylmetals

To a flame-dried 25 mL round bottom flask was charged Activated Mg (7.5 mmol, 1.5 eq.) and 5 mL anhydrous THF. To this suspension was added 2 drops of 1,2-dibromoethane. After 5 min, a solution of Aryl bromide (5 mmol, 1.0 eq.) in 5 mL anhydrous THF was slowly added to the suspension of Mg at room temperature. The reaction was mildly exothermic. The Grignard reagent was titrated and 1 mmol of this reagent was added to a flame-dried reaction vial. The solution was diluted with 3 mL anhydrous THF and after cooling to 0° C. in an ice bath, a solution of oxaziridine (1.5 mmol, 1.5 eq.) in 1 mL anhydrous THF was added. The ice bath was removed and the reaction was allowed to reach room temperature. After time t, the reaction was quenched with saturated aqueous NH$_4$Cl. The reaction mixture was diluted with 20 mL saturated aqueous NaCl and 20 mL EtOAc. The organic layer was separated and the aqueous layer was extracted with EtOAc (2×20 mL). The combined organic layer was dried over anhydrous Na$_2$SO$_4$, filtered and concentrated under reduced pressure. The residue was purified with flash chromatography.

a.

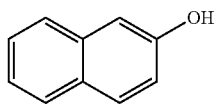

Naphthalen-2-ol
(33a)

t=2 h. Yield=86%; R$_f$=0.40 (Hexanes:EtOAc=4:1); $^1$H NMR (400 MHz, CDCl$_3$): δ 7.85-7.72 (m, 2H), 7.68 (d, J=8.4, 1H), 7.45 (td, J=8.4, 1.2 Hz, 1H), 7.35 (td, J=8.4, 1.2 Hz, 1H), 7.20-7.10 (m, 2H), 5.74 (br s, 1H); $^{13}$C NMR (100 MHz, CDCl$_3$): δ 153.3, 134.5, 129.8, 128.9, 127.7, 126.5, 126.3, 123.6, 117.7, 109.5. Spectral data is in accordance with the literature report (Tlili, et al., 2009).

b.

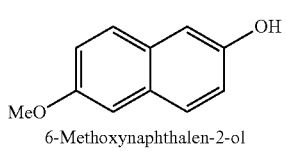

6-Methoxynaphthalen-2-ol
(33b)

t=4 h. Yield=75%; R$_f$=0.30 (Hexanes:EtOAc=4:1); $^1$H NMR (400 MHz, CDCl$_3$): δ 7.65 (d, J=8.4 Hz, 1H), 7.59 (d, J=8.8 Hz, 1H), 7.15-7.05 (m, 4H), 3.90 (s, 3H); $^{13}$C NMR (100 MHz, CDCl$_3$): δ 156.1, 151.7, 129.8, 129.7, 128.5, 127.8, 119.3, 118.0, 109.7, 106.0, 55.3. Spectral data is in accordance with the literature report (Schulz, et al., 2009).

c.

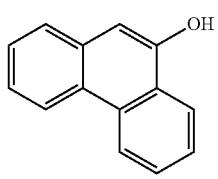

Phenanthren-9-ol
(33c)

t=4 h. Yield=57%; R$_f$=0.30 (Hexanes:EtOAc=4:1); $^1$H NMR (400 MHz, CDCl$_3$): δ 8.71-8.67 (m, 1H), 8.63-8.59 (m, 1H), 8.35-8.30 (m, 1H), 7.74-7.63 (m, 3H), 7.57-7.49 (m, 2H), 7.01 (s, 1H), 5.33 (br s, 1H); $^{13}$C NMR (100 MHz, CDCl$_3$): δ 149.4, 132.6, 131.5, 127.2, 126.9, 126.7, 126.4, 125.5, 124.3, 122.7, 122.6, 122.3, 106.11, 106.08. Spectral data is in accordance with the literature report (Guastavino and Rossi, 2012).

d.

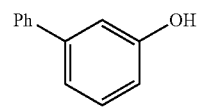

[1,1'-Biphenyl]-3-ol
(33d)

t=2 h. Yield=78%; R$_f$=0.35 (Hexanes:EtOAc=4:1); $^1$H NMR (400 MHz, CDCl$_3$): δ 7.62-7.58 (m, 2H), 7.49-7.43 (m, 2H), 7.42-7.31 (m, 2H), 7.25-7.20 (m, 1H), 7.13 (t, J=2.0 Hz, 1H), 6.91-6.86 (m, 1H), 5.41 (br s, 1H); $^{13}$C NMR (100 MHz, CDCl$_3$): δ 155.8, 143.0, 140.7, 130.1, 128.8, 127.5, 127.2, 119.8, 114.4, 114.2. Spectral data is in accordance with the literature report (Schmidt and Riemer, 2014)

e.

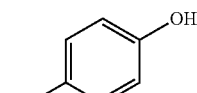

[1,1'-Biphenyl]-4-ol
(33e)

t=2 h. Yield=79%; R$_f$=0.40 (Hexanes:EtOAc=4:1); $^1$H NMR (400 MHz, CDCl$_3$): δ 7.57-7.53 (m, 2H), 7.49 (dd, J=6.8, 2.4 Hz, 2H), 7.45-7.40 (m, 2H), 7.35-7.28 (m, 1H), 6.92 (dd, J=6.4, 2.0 Hz, 2H); $^{13}$C NMR (100 MHz, CDCl$_3$): δ 155.0, 140.7, 134.0, 128.7, 128.4, 126.7 (2C), 115.6. Spectral data is in accordance with the literature report (Tlili, et al., 2009).

f.

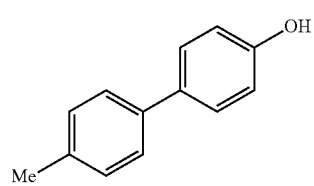

4'-Methyl-[1,1'-biphenyl]-4-ol
(33f)

t=2 h. Yield=61%; R$_f$=0.35 (Hexanes:EtOAc=4:1); $^1$H NMR (400 MHz, CDCl$_3$): δ 7.49-7.43 (m, 4H), 7.23 (d, J=8.8 Hz, 2H), 6.89 (dd, J=6.8, 2.0 Hz, 2H), 2.39 (s, 3H); $^{13}$C NMR (100 MHz, CDCl$_3$): δ 154.8, 137.9, 136.4, 134.0, 129.4, 128.2, 126.5, 115.6, 21.0. Spectral data is in accordance with the literature report (Edwards, et al., 2014)

g.

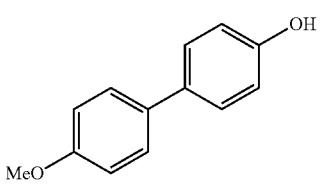

4'-Methoxy-[1,1'-biphenyl]-4-ol
(33g)

t=2 h. Yield=66%; R$_f$=0.40 (Hexanes:EtOAc=3:1); $^1$H NMR (600 MHz, CDCl$_3$): δ 7.47 (d, J=8.4 Hz, 2H), 7.43 (d, J=8.4 Hz, 2H), 6.96 (d, J=8.4 Hz, 2H), 6.88 (d, J=8.4 Hz, 2H), 3.85 (s, 3H); $^{13}$C NMR (151 MHz, CDCl$_3$): δ 158.7, 154.6, 133.8, 133.4, 128.0, 127.7, 115.6, 114.2, 55.3. Spectral data is in accordance with the literature report (Schmidt and Riemer, 2014)

h.

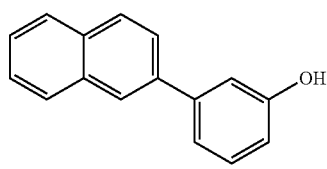

3-(Naphthalen-2-yl)phenol t=2 h. Yield=64%; R$_f$=0.35 (Hexanes:EtOAc=4:1); $^1$H NMR (400 MHz, CDCl$_3$): δ 8.03 (d, J=1.2 Hz, 1H), 7.93-7.85 (m, 3H), 7.72 (dd, J=8.8, 2.0 Hz, 1H), 7.56-7.48 (m, 2H), 7.41-7.30 (m, 2H), 7.21 (t, J=2.0 Hz, 1H), 6.91-6.85 (m, 1H), 5.24 (br s, 1H); $^{13}$C NMR (100 MHz, CDCl$_3$): δ 155.8, 142.9, 138.0, 133.6, 132.7, 130.1, 128.4, 128.2, 127.6, 126.3, 126.0, 125.8, 125.4, 120.0, 114.32, 114.30. Spectral data is in accordance with the literature report (Kikushima and Nishina, 2013).

i.

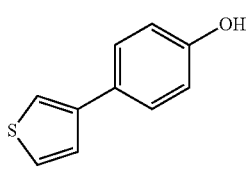

4-(Thiophen-3-yl)phenol t=2 h. Yield=31%; R$_f$=0.30 (Hexanes:EtOAc=4:1); $^1$H NMR (400 MHz, CDCl$_3$): δ 7.48 (dd, J=6.8, 2.0 Hz, 2H), 7.39-7.31 (m, 3H), 6.86 (dd, J=6.4, 2.0 Hz, 2H), 4.87 (br s, 1H); $^{13}$C NMR (100 MHz, CDCl$_3$): δ 154.8, 141.9, 129.0, 127.8, 126.2, 126.1, 119.0, 115.6. Spectral data is in accordance with the literature report (Cravino, et al., 2002).

j.

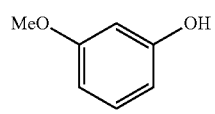

3-Methoxyphenol t=3 h. Yield=75%; R$_f$=0.35 (Hexanes:EtOAc=4:1); $^1$H NMR (400 MHz, CDCl$_3$): δ 7.14 (t, J=8.0 Hz, 1H), 6.54-6.43 (m, 3H), 5.84 (br s, 1H), 3.78 (s, 3H); $^{13}$C NMR (100 MHz, CDCl$_3$): δ 160.7, 156.7, 130.2, 107.9, 106.4, 101.5, 55.3. Spectral data is in accordance with the literature report (Tlili, et al., 2009).

k.

3-Methoxyphenol t=2 h. Yield=65%; R$_f$=0.35 (Hexanes:EtOAc=4:1); $^1$H NMR (400 MHz, CDCl$_3$): δ 6.82-6.75 (m, 4H), 5.46 (br s, 1H), 3.77 (s, 3H); $^{13}$C NMR (100 MHz, CDCl$_3$): δ 153.5, 149.5, 116.1, 114.9, 55.9. Spectral data is in accordance with the literature report (Tlili, et al., 2009).

l.

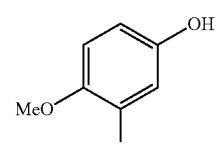

3-Fluoro-4-methoxyphenol

Yield=46%; R$_f$=0.40 (Hexanes:EtOAc=2:1); $^1$H NMR (600 MHz, CDCl$_3$): δ 6.83 (t, J=9.0 Hz, 1H), 6.64 (dd, J=12.6, 3.0 Hz, 1H), 6.58-6.50 (m, 1H), 5.68 (br s, 1H), 3.83 (s, 3H). $^{13}$C NMR (151 MHz, CDCl$_3$): δ 152.8 (d, J=245.7 Hz), 149.9 (d, J=10.0 Hz), 141.5 (d, J=11.0 Hz), 115.2 (d, J=3.3 Hz), 110.4 (d, J=3.3 Hz), 104.7 (d, J=20.8 Hz), 57.3. Spectral data is in accordance with the literature report (Freedman, et al., 2009).

m.

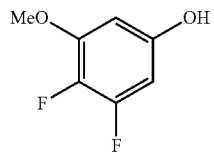

3,4-Difluoro-5-methoxyphenol t=2 h. Yield=35%; R$_f$=0.25 (Hexanes:EtOAc=1:1); $^1$H NMR (600 MHz, CDCl$_3$): δ 6.30-6.18 (m, 2H), 5.23 (br s, 1H), 3.85 (s, 3H); $^{13}$C NMR (151 MHz, CDCl$_3$): δ 151.9, 151.2, 151.14, 151.08, 151.06 150.4, 150.3, 149.43, 149.40, 149.38, 149.3, 136.9, 136.8, 135.3, 135.2, 96.68, 96.67, 96.4, 96.2, 56.6.

n.

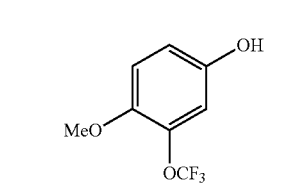

4-Methoxy-3-(trifluoromethoxy)phenol t=2 h. Yield=37%; $R_f$=0.35 (Hexanes:EtOAc=3:1); $^1$H NMR (600 MHz, CDCl$_3$): δ 7.06 (d, J=3.0 Hz, 1H), 6.96 (dd, J=9.0, 3.0 Hz, 1H), 6.89 (d, J=8.4 Hz, 1H), 3.84 (s, 3H); $^{13}$C NMR (151 MHz, CDCl$_3$): δ 151.6 (q, J=2.3 Hz), 148.7, 123.2 (q, J=272.0 Hz), 119.6, 119.5 (q, J=28.5 Hz), 114.3 (q, J=5.4 Hz), 113.9, 56.6.

o.

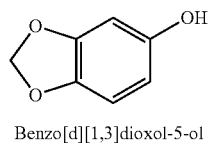

(33o)

Benzo[d][1,3]dioxol-5-ol t=2 h. Yield=63%; $R_f$=0.30 (Hexanes:EtOAc=4:1); $^1$H NMR (400 MHz, CDCl$_3$): δ 6.65 (d, J=8.4 Hz, 1H), 6.43 (d, J=2.8 Hz, 1H), 6.26 (dd, J=8.0, 2.8 Hz, 1H), 5.90 (s, 2H), 5.56 (br s, 1H); $^{13}$C NMR (100 MHz, CDCl$_3$): δ 150.4, 148.1, 141.5, 108.2, 106.7, 101.1, 98.3. Spectral data is in accordance with the literature report (Yu, et al., 2012).

p.

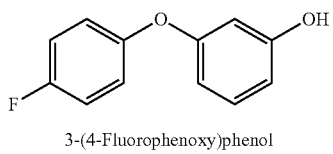

(33p)

3-(4-Fluorophenoxy)phenol t=2 h. Yield=65%; $R_f$=0.35 (Hexanes:EtOAc=5:1); $^1$H NMR (600 MHz, CDCl$_3$): δ 7.16 (t, J=8.4 Hz, 1H), 7.08-6.94 (m, 4H), 6.56 (dd, J=8.4, 2.4 Hz, 1H), 6.53 (dd, J=8.4, 2.4 Hz, 1H), 6.46 (t, J=2.4 Hz, 1H), 5.19 (br s, 1H); $^{13}$C NMR (151 MHz, CDCl$_3$): δ 159.8, 159.1, 158.2, 156.8, 152.4, 130.4, 120.9, 120.9, 116.4, 116.2, 110.3, 110.1, 105.4. Spectral data is in accordance with the literature report (Xue, et al., 2010).

q.

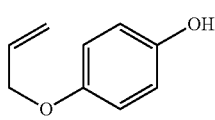

(33q)

4-(Allyloxy)phenol t=2 h. Yield=63%; $R_f$=0.30 (Hexanes:EtOAc=4:1); $^1$H NMR (600 MHz, CDCl$_3$): δ 6.86-6.78 (m, 2H), 6.77-6.71 (m, 2H), 6.10-6.00 (m, 1H), 5.40 (dq, J=17.4, 1.8 Hz, 1H), 5.27 (dq, J=10.2, 1.8 Hz, 1H), 4.48 (dt, J=6.0, 1.8 Hz, 2H); $^{13}$C NMR (151 MHz, CDCl$_3$): δ 152.6, 149.7, 133.4, 117.6, 116.0, 116.0, 69.7. Spectral data is in accordance with the literature report (Chavez, et al., 2011).

r.

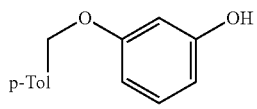

(33r)

3-((4-Methylbenzyl)oxy)phenol t=2 h. Yield=51%; $R_f$=0.40 (Hexanes:EtOAc=4:1); $^1$H NMR (600 MHz, CDCl$_3$): δ 7.32 (d, J=7.8 Hz, 2H), 7.21 (d, J=7.8 Hz, 2H), 7.14 (t, J=8.4 Hz, 1H), 6.61-6.56 (m, 1H), 6.49 (t, J=2.4 Hz, 1H), 6.46-6.41 (m, 1H), 5.04 (br s, 1H), 4.99 (s, 2H), 2.38 (s, 3H); $^{13}$C NMR (151 MHz, CDCl$_3$): δ 160.1, 156.6, 137.7, 133.8, 130.1, 129.2, 127.6, 108.0, 107.4, 102.5, 70.0, 21.2. Spectral data is in accordance with the literature report (Sajiki, et al., 2003).

s.

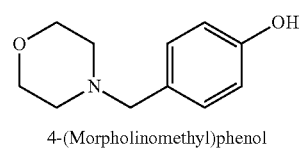

(33s)

4-(Pyrrolidin-1-yl)phenol t=2 h. Yield=54%; $R_f$=0.35 (Hexanes:EtOAc=3:1); $^1$H NMR (600 MHz, Acetone-d$_6$) δ 7.41 (s, 1H), 6.73 (d, J=6.6 Hz, 2H), 6.46 (d, J=8.4 Hz, 2H), 3.39-3.09 (m, 4H), 2.02-1.86 (m, 4H); $^{13}$C NMR (151 MHz, Acetone-d$_6$) δ 148.1, 142.6, 115.8, 112.8, 48.0, 25.0. Spectral data is in accordance with the literature report (Liu, et al., 2013).

t.

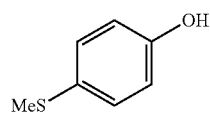

(33t)

4-(Morpholinomethyl)phenol t=2 h. Yield=76%; $R_f$=0.20 (100% EtOAc); $^1$H NMR (600 MHz, Acetone-d$_6$) δ 8.28 (s, 1H), 7.15 (d, J=8.4 Hz, 2H), 6.79 (d, J=8.4 Hz, 2H), 3.61 (t, J=4.8 Hz, 4H), 3.38 (s, 2H), 2.51-2.23 (m, 4H); $^{13}$C NMR (151 MHz, Acetone-d$_6$) δ 156.5, 130.3, 128.8, 115.0, 66.6, 62.6, 53.5. Spectral data is in accordance with the literature report (Dinges, et al., 2007).

u.

(33u)

4-(Methylthio)phenol t=2 h. Yield=63%; $R_f$=0.35 (Hexanes:EtOAc=4:1); $^1$H NMR (400 MHz, CDCl$_3$): δ 7.21 (d, J=8.8 Hz, 2H), 6.78 (d, J=8.8 Hz, 2H), 5.42 (s, 1H), 2.44 (s, 3H); $^{13}$C NMR (100 MHz, CDCl$_3$): δ 153.9, 130.3, 128.7, 116.1, 17.9. Spectral data is in accordance with the literature report (Zhu, et al., 2012).

v.

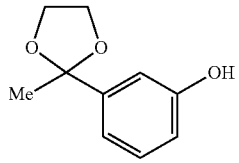

3-(2-Methyl-1,3-dioxolan-2-yl)phenol t=2 h. Yield=64%; R$_f$=0.45 (Hexanes:EtOAc=3:1); $^1$H NMR (600 MHz, CDCl$_3$): δ 7.22 (t, J=7.8 Hz, 1H), 7.08-7.00 (m, 2H), 6.83-6.75 (m, 1H), 6.21 (s, 1H), 4.11-3.99 (m, 2H), 3.85-3.75 (m, 2H), 1.67 (s, 3H); $^{13}$C NMR (151 MHz, CDCl$_3$): δ 155.8, 144.8, 129.7, 117.4, 114.9, 112.3, 108.9, 64.4, 27.4. Spectral data is in accordance with the literature report (Sato, et al., 2009).

w.

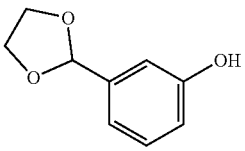

3-(1,3-Dioxolan-2-yl)phenol t=2 h. Yield=73%; R$_f$=0.45 (Hexanes:EtOAc=3:1); $^1$H NMR (600 MHz, CDCl$_3$): δ 7.20 (t, J=7.8 Hz, 1H), 7.02 (d, J=7.8 Hz, 1H), 6.91 (s, 1H), 6.77 (dd, J=8.4, 1.8 Hz, 1H), 6.40 (br s, 1H), 5.77 (s, 1H), 4.17-4.06 (m, 2H), 4.05-3.92 (m, 2H); $^{13}$C NMR (151 MHz, CDCl$_3$): δ 155.8, 139.2, 129.7, 118.7, 116.4, 113.2, 103.4, 65.2. Spectral data is in accordance with the literature report (Dodo, et al., 2008).

x.

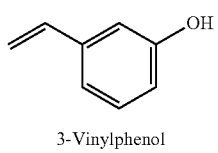

3-Vinylphenol t=2 h. Yield=39%; R$_f$=0.25 (Hexanes:EtOAc=4:1); $^1$H NMR (400 MHz, CDCl$_3$): δ 7.22 (t, J=8.0 Hz, 1H), 7.01 (t, J=7.6 Hz, 1H), 6.92 (d, J=1.2 Hz, 1H), 6.78 (dd, J=8.0, 0.8 Hz, 1H), 6.67 (dd, J=17.6, 11.2 Hz, 1H), 5.73 (d, J=17.6 Hz, 1H), 5.32 (br s, 1H), 5.27 (d, J=11.2 Hz, 1H); $^{13}$C NMR (100 MHz, CDCl$_3$): δ 155.5, 139.3, 136.4, 129.7, 119.1, 114.9, 114.3, 112.8. Spectral data is in accordance with the literature report (Liu, et al., 2015).

y.

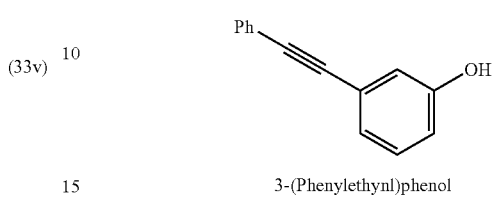

3-(Phenylethynl)phenol t=2 h. Yield=39%; R$_f$=0.25 (Hexanes:EtOAc=5:1); $^1$H NMR (400 MHz, CDCl$_3$): δ 7.60-7.52 (m, 2H), 7.41-7.34 (m, 3H), 7.24 (t, J=8.0 Hz, 1H), 7.15 (d, J=7.2 Hz, 1H), 7.08-7.00 (m, 1H), 6.85 (dd, J=8.0, 2.0 Hz, 1H), 5.28 (br s, 1H); $^{13}$C NMR (100 MHz, CDCl$_3$): δ 155.2, 131.6, 129.7, 128.3(2C), 124.43, 124.37, 123.0, 118.2, 115.8, 89.4, 88.9. Spectral data is in accordance with the literature report (Xu, et al., 2014).

z.

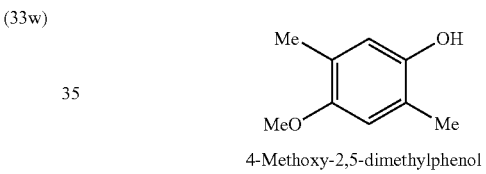

4-Methoxy-2,5-dimethylphenol t=2 h. Yield=40%; R$_f$=0.30 (Hexanes:EtOAc=4:1); $^1$H NMR (600 MHz, CDCl$_3$): δ 6.61 (s, 1H), 6.59 (s, 1H), 4.41 (br s, 1H), 3.78 (s, 3H), 2.23 (s, 3H), 2.16 (s, 3H); $^{13}$C NMR (151 MHz, CDCl$_3$): δ 151.7, 147.1, 125.1, 121.1, 117.6, 113.4, 56.1, 15.8, 15.7. Spectral data is in accordance with the literature report (Hartz, et al., 2009).

Example 5—Amination Employing Organozinc Reagents in the Presence of Copper(I) Salts and Hydroxylamines To further expand the scope of this method, arylmetals with lower basicity (i.e., containing metals other than Mg and Li) while still possessing sufficient nucleophilicity to react with NH oxaziridines were explored. Monoaryl organozinc reagents (ArZnX) were initially evaluated. These versatile compounds are less basic than the corresponding aryl-lithium and aryl-magnesium compounds, and are known to tolerate a wider range of functional groups. Recent developments in the direct zincation of arenes by Knochel et. al. also provides a practical method for their preparation (Wunderlich, 2007; Wunderlich, 2008; Mosrin, 2009).

TABLE 3

Optimization of conditions for the direct primary amination of arylmetals.

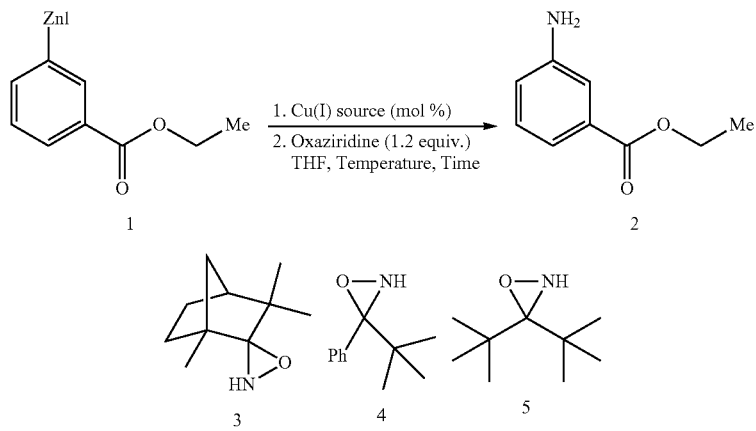

| Entry[a] | Cu Source | Oxaziridine | Temp, Time | Yield (%) |
|---|---|---|---|---|
| 1 | Not used | 3/4/5 | rt, 16 h | 0% |
| 2 | CuCl (20 mol %) | 3 | rt, 16 h | 11% |
| 3 | CuCl (20 mol %) | 4 | rt, 16 h | 16% |
| 4 | CuCl (100 mol %) | 4 | rt, 16 h | 28% |
| 5 | CuCl (20 mol %) | 4 | 40° C., 16 h | 18% |
| 6 | CuCl (20 mol %) | 5 | rt, 16 h | 34% |
| 7 | CuCN (20 mol %) | 5 | rt, 16 h | 42% |
| 8 | [Cu(OTf)]$_2$ · C$_6$H$_6$ (10 mol %) | 5 | rt, 16 h | 13% |
| 9 | Cu(OAc)$_2$ (20 mol %) | 5 | rt, 16 h | 43% |
| 10 | CuCN (110 mol %) | 5 | rt, 16 h | 68% |
| 11 | CuCN.2LiCl (110 mol %) | 5 | rt, 16 h | 66% |
| 12 | CuCN.2LiCl (110 mol %) | 5 | −78° C., 10 min | 87% |
| 13 | CuCl.2LiCl (110 mol %) | 5 | −78° C., 10 min | 90% |

When arylzinc halide 1 was reacted with three different oxaziridines (3-5), formation of the desired aniline 2 was not observed (Table 3 entry 1). These results indicated that the balance of arylmetal basicity and nucleophilicity does not fall in the optimal range required for the amination by an NH oxaziridine. The aggregation of organozinc molecules in solution likely renders them insufficiently nucleophilic for a successful direct amination, in contrast to the observed behavior of aryl Grignard reagents (Gao, 2016).

Next, an organocuprate, which can be easily prepared from the corresponding organolithium, organomagnesium or organozinc reagents via transmetallation with Cu(I) sources such as CuCN and CuCl, was examined. Initially catalytic amounts of Cu(I) salts were employed. The anticipated primary amination product (2) was isolated, albeit in low yield (Table 3 entries 2 & 3). Addition of a stoichiometric amount of copper afforded much better yield (Table 3, entries 4 vs 3), indicating that the catalytic cycle could not be established for some substrates. This result was not unexpected given the aforementioned issue with deprotonation. Less hindered NH-oxaziridine 5 gave better yield than bulkier NH-oxaziridines 3 & 4 under catalytic conditions (Table 3, entries 6, 7 & 9 vs 3) as well as under stoichiometric conditions (Table 3, entry 10 vs 4). Many Cu(I) salts efficiently mediate the reaction, although CuCN.2LiCl and CuCl-2LiCl gave the best results and were easy to handle under inert atmosphere using their commercially available THF solutions (Table 3, entries 12 & 13).

While copper catalyzed/mediated aminations of arylmetals have been reported in the literature, the vast majority can only produce tertiary amines due to the lack of suitable electrophilic "NH$_2$" equivalents. The Uchiyama group reported a method in which an arylcuprate could be efficiently aminated using O-benzyl-hydroxylamine (BnONH$_2$, FIG. 1B) (Tezuka, 2016). While this innovative approach provides precious metal-free access to primary anilines with good efficiency and decent scope, it is not without some serious limitations. One of the major issues of this method is the requirement for neighboring group participation, which limits the substrates to those with directing groups (DMG) at the ortho-position of the metal-bearing carbon. This requirement is due to the unique transition state that necessitates coordination to these directing groups to facilitate the formation of the C—N bond (Tezuka, 2016). Another drawback is the requirement for the use of (TMP)$_2$Cu, which is needed for both the initial deprotonation of the arene and the mono-deprotonation of BnONH$_2$. Since direct cupration with (TMP)$_2$Cu also involves some restrictions on the substrates, it is not trivial to expand the scope beyond what has been reported. The aminating reagent BnONH$_2$, of which two equivalents are needed, also requires excessive drying before use because it is very hygroscopic, which further limits the utility of this method especially in large-scale processes.

Using an NH-oxaziridine as the aminating reagent alleviates many of these limitations. Since the acidity of the N—H bond in oxaziridines (pKa=~34) is much lower than in BnONH$_2$ (pKa=~20), it was anticipated that the unproductive protonation of the cuprate was not going to be a significant problem in the context of the present disclosure, therefore neither a base nor excess aminating agent were needed. NH-Oxaziridine 5 also efficiently aminates the arylcuprate in the absence of a directing group, which greatly expands the scope of substrates. Lastly, the cuprates can be prepared via transmetallation using a wide range of starting materials such as organolithiums, organozincs or organomagnesiums, that circumvents the limitation that originates from Uchiyama's directed cupration.

TABLE 4

Primary amination of structurally diverse aryl- and heteroarylmetals

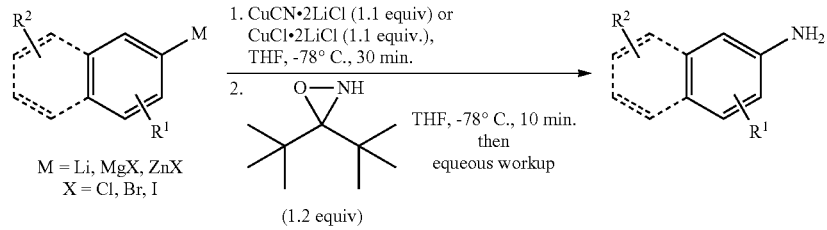

Structure of Primary Arylamines (Entry)[a]: Compound #, Metal (M), Isolated Yield (%)[b]

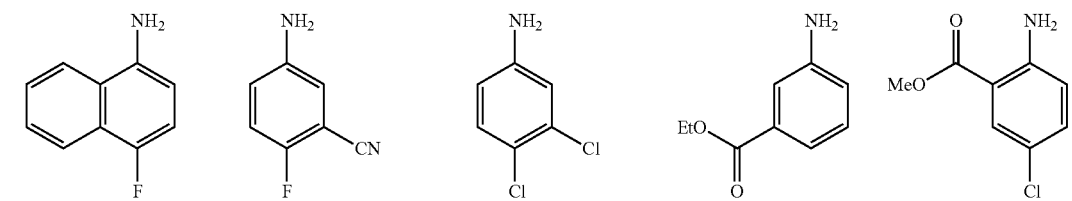

(1) 6
M = MgBr
53%

(2) 7
M = ZnBr
86% (1.1 equiv Cu)
35% (20 mol % Cu)

(3) 8
M = ZnI
65%

(4) 2
M = ZnI
90% (-78° C.)
68% (25° C.)

(5) 9
M = ZnBr
88% (1.1 equiv Cu)
84% (20 mol % Cu)

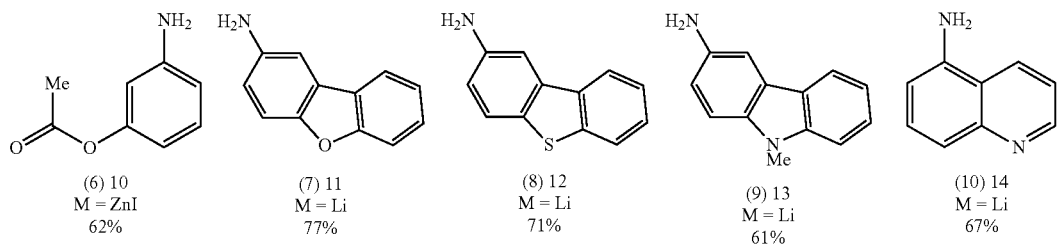

(6) 10
M = ZnI
62%

(7) 11
M = Li
77%

(8) 12
M = Li
71%

(9) 13
M = Li
61%

(10) 14
M = Li
67%

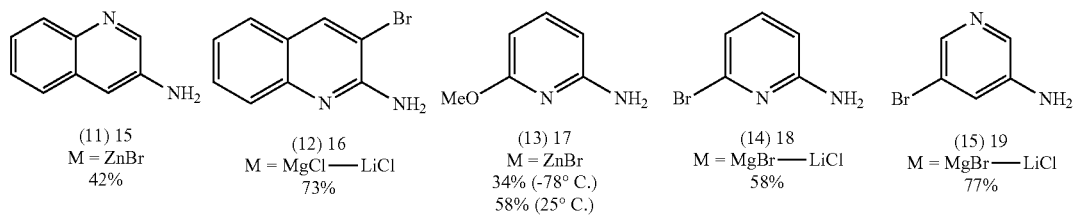

(11) 15
M = ZnBr
42%

(12) 16
M = MgCl—LiCl
73%

(13) 17
M = ZnBr
34% (-78° C.)
58% (25° C.)

(14) 18
M = MgBr—LiCl
58%

(15) 19
M = MgBr—LiCl
77%

TABLE 4-continued

Primary amination of structurally diverse aryl- and heteroarylmetals

[Reaction scheme: ArM + oxaziridine reagent → ArNH$_2$]

1. CuCN·2LiCl (1.1 equiv) or CuCl·2LiCl (1.1 equiv.), THF, −78° C., 30 min.
2. Oxaziridine (1.2 equiv), THF, −78° C., 10 min. then aqueous workup M = Li, MgX, ZnX; X = Cl, Br, I Structure of Primary Arylamines
(Entry)[a]: Compound #, Metal (M), Isolated Yield (%)[b]

(16) 20, M = MgCl—LiCl, 45% (3,5-dibromopyridin-2-amine)

(17) 21, M = 1/2 Zn, 33% (2,6-dichloropyridin-3-amine)

(18) 22, M = ZnBr, 83% (−78° C.), 51% (25° C.), 61% (−78° C. & 20 mol % Cu) (ethyl 5-aminothiophene-2-carboxylate)

(19) 23, M = Li, 58% (steroid-derived arylamine)

(20) 24, M = Li, 55% (tocopherol-derived arylamine)

[a]Reaction conditions: arylmetal (1 mmol) and Cu(I)-reagent (1.1 mmol unless indicated otherwise), were mixed at −78° C. for 30 minutes in THF followed by the THF solution of the oxaziridine reagent (1.2 mmol) at −78° C. for 10 minutes unless indicated otherwise.
[b]Isolated yield after column chromatography. Reactions were quenched at the indicated reaction temperature with a ~1:1 mixture of saturated NH$_4$Cl(aq) and saturated Na$_2$S$_2$O$_3$ (aq).

When applied to a wide range of substrates that did not perform well in the direct primary amination of aryl Grignard reagents (Gao, 2016), the Cu-mediated method provides not only better yields in all cases but also furnishes many new anilines that were previously inaccessible directly from the corresponding Grignard reagents (Table 4). Electron-deficient arenes (Table 4, entry 1-3) and heterocycles (Table 4, entries 7-20) performed well and afforded isolated yields up to 90%. These conditions are compatible with esters (Table 4, entry 4-6, 18), nitriles (Table 4, entry 2), and give decent yields for complex molecules (Table 4, entries 19, 20). The reaction is very rapid and in most cases it takes less than 10 min at −78° C. to reach completion. Synthetically useful yields (50-60%) could also be achieved at ambient temperature (Table 4, entries 4, 13 and 18). Both CuCN·2LiCl and CuCl·2LiCl gave similar yields and control experiments showed that LiCl was not essential for the success of this reaction.

When less basic organozincs are used as the arylmetal substrates, this reaction can be rendered catalytic (Table 4, entry 2, 5 and 18). However, the success of the catalytic system largely depends on the electronic properties of the specific organozinc substrate. An ester group at the ortho position greatly improves the yield (Table 4, entry 5)—this result is consistent with the findings reported by Uchiyama.

Next, amination with N-alkyl-O-benzoyl hydroxylamines (BzONHR) was attempted with the goal of obtaining secondary anilines (ArNHR). Johnson et al. reported a few examples where a diarylzinc substrate (R$_2$Zn) could be converted to RNHR' using BzONHR' in the presence of catalytic amounts of CuOTf (Berman and Johnson, 2006). In these cases, one of the R groups in R$_2$Zn presumably first deprotonates the hydroxylamine and facilitates the nitrogen-transfer to the remaining R group, thus allowing catalytic amounts of a Cu(I) salt to drive the amination while sacrificing one of the R groups as a base.

TABLE 5

Secondary amination of selected aryl- and heteroarylmetals

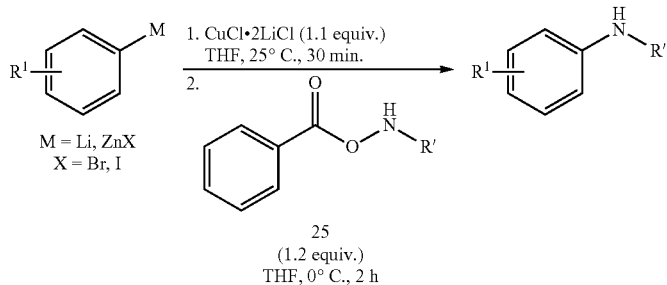

M = Li, ZnX
X = Br, I 25
(1.2 equiv.)
THF, 0° C., 2 h

Structure of Secondary Arylamines
(Entry)[a]: Compound #, Metal (M), Isolated Yield (%)[b]

(21) 26
M = ZnI
71%

(22) 27
M = ZnBr
57%

(23) 28
M = ZnI
76%

(24) 29
M = ZnBr
61%

(25) 30
M = ZnI
65%

(26) 31
M = ZnBr
49%

(27) 32
M = ZnI
83%

(28) 33
M = ZnI
88%

(29) 34
M = Li
60%

[a]Reaction conditions: arylmetal (1 mmol) and Cu(I)-reagent (1.1 mmol) were mixed at 25° C. for 30 minutes in THF, followed by the THF solution of the hydroxylamine reagent (1.2 mmol) at 0° C. for 2 hours.
[b]Isolated yield after column chromatography. Reactions were quenched at the indicated reaction temperature with a ~1:1 mixture of saturated NH$_4$Cl (aq) and saturated Na$_2$S$_2$O$_3$ (aq).

It was anticipated that upon complete transmetallation of the arylzinc substrate, the resulting cuprate would undergo exclusive amination instead of protonation, therefore this approach would improve overall atom economy by avoiding the unproductive quenching of the R group. Without wishing to be bound by any theory, it is believed that this hypothesis is correct and arylcuprates (ArCuX) were successfully aminated with good to excellent yields when reacted with 1.1 equivalents of BzONHR' at ambient temperature (Table 5). When the reaction was carried out with TsONHR', the yield was lower, which is consistent with the hypothesis that the acidity of NH has a major impact on the reaction outcome.

Mechanistically it is possible that the amination of arylcuprates follows the same pathway as the direct amination of Grignard reagents with NH-oxaziridines in which the amination takes place by direct nucleophilic attack on the nitrogen atom (Scheme 7A) (Gao, 2016). However, if the reaction involved a simple nucleophilic attack, one would also expect the amination to proceed when an organozinc reagent was reacted directly with oxaziridine 5 in the absence of copper complexes. Since the much less nucleophilic reagent (cuprate) yielded the desired aniline, the failed direct amination of organozinc reagents points to a different mechanistic pathway that likely involves the unique ability of copper to undergo oxidation state change [i.e., Cu(I)→Cu (III)]. It is proposed that the amination starts with the initial oxidative addition of Cu(I) into the N—O bond of oxaziridine 5 to afford intermediate 38, followed by reductive elimination to generate intermediate 35. Finally, facile hydrolysis of 36 gives rise to the product primary arylamine 37. The mechanism that leads to the formation of secondary arylamines involves oxidative addition of the arylcuprate into the N—O bond of aminating agent 25 and the resulting intermediate 39 directly furnishes the secondary arylamine product (40) upon reductive elimination (Scheme 7C). These above mentioned two pathways (Scheme 7B & 7C) are similar to the mechanism proposed by Uchiyama et al (Tezuka, 2016).

described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

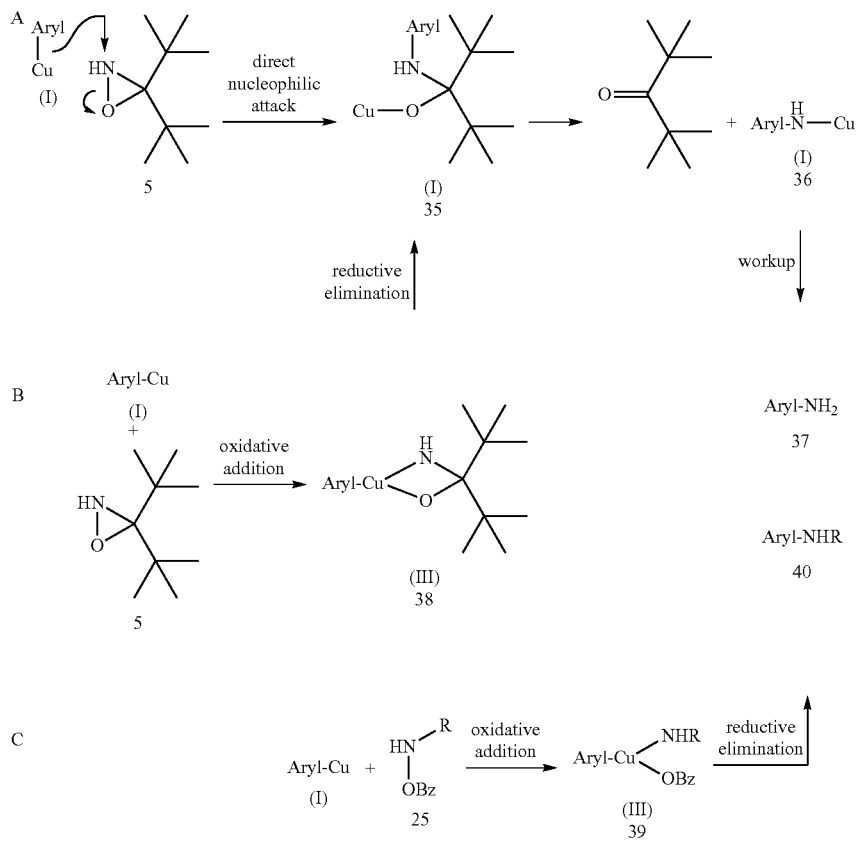

Scheme 7. Proposed mechanistic pathways.

It is contemplated that a successful catalytic cycle demands the co-existence of the initial non-transmetalated arylmetal and the NH-oxaziridine. It is not surprising that only relatively less basic arylmetals (e.g., Table 3, entries 5 & 18) are amenable to catalytic primary amination. Presumably, in all of the other cases, the arylmetals undergo rapid and non-productive quenching by the NH-oxaziridine reagent before the arylcuprates can form via transmetallation.

It is contemplated that this general and operationally simple amination approach will find wide utility in the synthesis of structurally complex molecules such as active pharmaceutical ingredients and natural products.

All of the compositions and/or methods disclosed and claimed herein can be made and executed without undue experimentation in light of the present disclosure. While the compositions and methods of this disclosure have been

VIII. REFERENCES

The following references, to the extent that they provide exemplary procedural or other details supplementary to those set forth herein, are specifically incorporated herein by reference:

Ahammed, et al., *J. Org. Chem.*, 76:7235-7239, 2011.
Alonso, et al., *Chem.—Eur. J.*, 16:5274-5284, 2010.
Altenbach et al., *J. Med. Chem.*, 51:6571-6580, 2008.
Alvarez-Builla, et al., Eds., *Modern Heterocyclic Chemistry* John Wiley & Sons, Hoboken, N.J., vols. 1-4, 2011.
Austin, *J. Org. Chem.*, 46:2280-2286, 1981.
Bahrami, *Tetrahedron*, 68:5095-5101, 2012.
Barker and Jarvo, *J. Am. Chem. Soc.*, 131:15598-15599, 2009.
Barker and Jarvo, *Synthesis*, 3954-3964, 2011.

Berman and Johnson, *J. Am. Chem. Soc.*, 126:5680-5681, 2004.
Berman and Johnson, *J. Org. Chem.*, 71:219, 2006.
Blair et al., *J. Med. Chem.*, 43:4701-4710, 2000.
Blaser, et al., in *Fine Chem. Heterog. Catal.* pp. 389-406, 2001.
Blaser, et al., *ChemCatChem.*, 1:210-221, 2009.
Borzenko et al., *Angew. Chem. Int. Ed.*, 54:3773-3777, 2015.
Chavez et al., *J. Med. Chem.*, 54:4659-4669, 2011.
Cheemala and Knochel, *Org. Lett.*, 9:3089-3092, 2007.
Chen et al., *J. Org. Chem.*, 76:2338-2344, 2011.
Cheung, et al., *Org. Lett.*, 15:3734-3737, 2013.
Chiba and Narasaka, *Amino Group Chem.*, 1-54, 2008.
Chinnusamy, et al., *Compr. Org. Synth.* (*2nd Ed.*), 7:692-718, 2014.
Corpet and Gosmini, *Synthesis*, 46:2258-2271, 2014.
Cravino et al., *J. Phys. Chem. B.*, 106:70-76, 2002.
Cross et al., *J. Med. Chem.*, 53:7076-7094, 2010.
Dey et al., *ACS Appl. Mater. Interfaces* 6:10231-10237, 2014.
Djukic, et al., *Inorg. Chem.*, 50:7334-7343, 2011.
Dinges et al., *J. Med. Chem.*, 50:2011-2029, 2007.
Dodo et al., *Bioorg. Med. Chem.*, 16:4272-4285, 2008.
Edwards et al., *J. Org. Chem.*, 79:2094-2104, 2014.
Enthaler and Company, *Chem. Soc. Rev.*, 40:4912-4924, 2011.
Erdik, in *Chem. Hydroxylamines, Oximes Hydroxamic Acids*, S. Patai, Ed. Wiley, pp. 303-341, 2009.
European Patent No. EP 2336107
Fan et al., *Chem. Commun.*, 50:5733, 2014.
Fan, et al., *Org. Lett.* 17:5934-5937, 2015.
Fattori, et al., *Synthesis*, 2009:1305-1308, 2009.
Feiring, *J. Org. Chem.*, 44:2907-2910, 1979.
Fountoulaki et al., *ACS Catalysis*, 4:3504-3511, 2014.
Freedman and Stewart, *J. Heterocyclic Chem.*, 26:1547-1554, 2009.
Gao et al., *Nat. Chem.*, advance online publication, 2016.
Garcia et al., *Adv. Synth. & Catal.*, 354:321-327, 2012.
Garrett and Prasad, *Adv. Synth. Catal.*, 346:889-900, 2004.
Gasparotto, *J. Med. Chem.*, 50:5509-5513, 2007.
Green and Hartwig, *Org. Lett.*, 16:4388-4391, 2014.
Guagnano et al., *J. Med. Chem.*, 54:7066-7083, 2011.
Guan, *Compr. Org. Synth.* (*2nd Ed.*), 7:302-312, 2014.
Guastavino and Rossi, *J. Org. Chem.*, 77:460-472, 2012.
Hagooly and Rozen, *J. Org. Chem.*, 73:6780-6783, 2008.
Hartz et al., *J. Med. Chem.*, 52:4173-4191, 2009.
Hay et al., *Tetrahedron Lett.*, 52:5728-5732, 2011.
Hili and Yudin, *Nat. Chem. Biol.*, 2:284-287, 2006.
Hostetler, et al., *J. Org. Chem.*, 64:178-185, 1999.
Irie, et al., *Eur. J. Org. Chem.*, 2009:2243-2250, 2009.
Jiao, et al., *ACS Catal.* 6:610-633, 2016.
Kawano, et al., *J. Am. Chem. Soc.*, 132:6900-6901, 2010.
Kholdeeva and Zalomaeva, *Coordination Chemistry Reviews*, 306:302-330, 2016.
Kikushima and Nishina, *RSC Adv.*, 3:20150, 2013.
Kitamura, et al., *Bull. Chem. Soc. Jpn.*, 76:1063-1070, 2003.
Kitamura, et al., *Org. Lett.*, 6:4619-4621, 2004.
Kitching et al., *J. Org. Chem.*, 42:2411-2418, 1977.
Klatt, et al., *Journal of Organic Chemistry*, 79:4253-4269, 2014.
Klinkenberg and Hartwig, *Angew. Chem., Int. Ed.*, 50:86-95, 2011.
Knochel et al., *Angew. Chem., Int. Ed.*, 42:4302-4320, 2003.
Knochel, *Organomet. Synth.*, 223-372, 2013.
Kumaran and Leong, *Organometallics*, 34:1779-1782, 2015.
Lau, et al., *J. Med. Chem.*, 50:113-128, 2007.
Lee, et al., *Org. Lett.*, 3:2729-2732, 2001.
Liu et al., *J. Fluorine Chem.*, 156:327-33, 2013.
Liu, et al., *J. Med. Chem.*, 58:9228-9237, 2015.
Love and Jones, *J. Org. Chem.*, 64:3755-3756, 1999.
Lundgren, et al., *Angew. Chem. Int. Ed.*, 49:4071-4074, 2010.
Maiti and Buchwald, *J. Am. Chem. Soc.*, 131:17423-17429, 2009.
Makosza, *Chemical Society Reviews*, 39:2855-2868, 2010.
Makosza, *Synthesis*, 2341-2356, 2011.
Makosza, *Chem.—Eur. J.*, 20:5536-5545, 2014.
Mallat, et al., Amination reactions. *Handb. Heterog. Catal.* (*2nd Ed.*). 7:3548-3564, 2008.
Markiewicz, et al., *J. Org. Chem.*, 75:4887-4890, 2010.
Mosrin et al., *Org. Lett.*, 11:3406, 2009.
Mlynarski, et al., *J. Am. Chem. Soc.* 134:16449-16451, 2012.
Olson, Mini-Rev. *Org. Chem.*, 8:341-346, 2011.
Page et al., *J. Org. Chem.*, 65:4204-4207, 2000.
Patel et al., *J. Med. Chem.*, 57:5579-5601, 2014.
Petersen, *Synthesis*, 1999:1763-1766, 1999.
Phetrak, et al., *J. Org. Chem.*, 78:12703-12709, 2013.
Qiao and Lam in *Boronic Acids* (*2nd Ed.*), D. G. Hall, Ed. Wiley-VCH, vol. 1, pp. 315-361, 2011a.
Qiao and Lam, *Synthesis*, 829-856, 2011b.
Qiu, et al., *J. Med. Chem.*, 42:329-332, 1999.
Qiu and Norwood, *J. Liq. Chromatogr. Relat. Technol.*, 30:877-935, 2007.
Rappoport, *The Chemistry of Phenols*, John Wiley & Sons, Chichester, 2004).
Rappoport, Editor, *The Chemistry of Anilines*, Parts 1-2, John Wiley & Sons, Chichester, 2007.
Rappoport and Marek, Editors, *The Chemistry of Organomagnesium Compounds*, John Wiley & Sons, 2008.
Rao and Fu, *Synlett*, 745-769, 2011.
Ricci, Editor, *Amino Group Chemistry: From Synthesis to the Life Sciences*, Wiley-VCH, 2008.
Rucker, et al., *Angew. Chem., Int. Ed.*, 51:3953-3956, S3953/1-S3953/108, 2012.
Sajiki and Hirota, *Chem. Pharm. Bull.*, 51:320-324, 2003.
Sato, et al., *Synthesis*, 2009:1318-1322, 2009.
Schmidt and Riemer, *J. Org. Chem.*, 79:4104-4118, 2014.
Schulz et al., *Angew. Chem. Int. Ed.*, 48:918-921, 2009.
Sharma, et al., *J. Org. Chem.* 79:9433-9439, 2014.
Shen and Hartwig, *J. Am. Chem. Soc.*, 128:10028-10029, 2006.
Starkov, et al., *Chem.—Eur. J.*, 21:5278-5300, 2015.
Surry and Buchwald, *J. Am. Chem. Soc.*, 129:10354-10355, 2007.
Terrier, Ed., *Modern Nucleophilic Aromatic Substitution* John Wiley & Sons, Hoboken, N.J., 2013.
Tezuka et al., *J. Am. Chem. Soc.*, 138:9166, 2016.
Thirunavukkarasu, et al., *Chem. Commun.* (Cambridge, U. K.), 50:29-39, 2014.
Tlili, et al., *Angew. Chem. Int. Ed.*, 48:8725-8728, 2009.
Tsutsui, et al., *Bull. Chem. Soc. Jpn.*, 72:1869-1878, 1999.
Tordeux and Wakselman, *J. Fluorine Chem.*, 74:251-254, 1995.
U.S. Pat. No. 5,104,892.
U.S. Patent Publication No. 2010/0190747.
Van Brandt et al., *Eur. J. Org. Chem.*, 2012:7048-7052, 2012.
Vo and Hartwig, *J. Am. Chem. Soc.*, 131:11049-11061, 2009.
Welch et al., *Organic Process Research & Development*, 9:198-205, 2005.
Wolfe, et al., *Acc. Chem. Res.*, 31:805-818, 1998.
Wunderlich et al., *Angew. Chem., Int. Ed.*, 46:7685, 2007.

Wunderlich et al., *Chem. Commun.*, 6387, 2008.
Xu and Wolf, *Chem. Commun.*, 3035, 2009.
Xu, et al., *Adv. Synth. Catal.*, 356:2029-2039, 2014.
Xue et al., *Bioorg. Med. Chem.*, 18:6526-6537, 2010.
Yoo, et al., *J. Am. Chem. Soc.*, 133:7652-7655, 2011.
Yu, et al., *Org. Lett.*, 14:3688-3691, 2012.
Zhang, et al., *J. Org. Chem.*, 74:8595-8603, 2009.
Zhao, et al., *Chem. Commun.*, 46:9049, 2010.
Zhu, et al., *J. Am. Chem. Soc.*, 134:18253-18256, 2012.
Zhu, et al., *Org. Lett.*, 14:3494-3497, 2012.

What is claimed is:

1. A method of preparing an aminoaromatic compound or a hydroxyaromatic compound comprising:

(A) admixing a metal aromatic compound with an oxaziridine compound to form a first reaction mixture under conditions sufficient to cause a reaction to obtain an anionic intermediate; wherein the oxaziridine compound is further defined as:

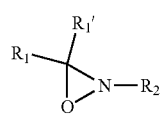

(I)

wherein:

$R_1$ and $R_1'$ are each independently alkyl$_{(C \leq 12)}$, cycloalkyl$_{(C \leq 12)}$, aryl$_{(C \leq 12)}$, or a substituted version of any of these groups, or $R_1$ and $R_1'$ are taken together and are a cycloalkanediyl$_{(C \leq 18)}$ or substituted cycloalkanediyl$_{(C \leq 18)}$; and $R_2$ is hydrogen or alkyl$_{(C \leq 12)}$, aryl$_{(C \leq 12)}$, aralkyl$_{(C \leq 12)}$, or a substituted version of any of these three groups;

(B) admixing a weak acid with the anionic intermediate to obtain a second reaction mixture under conditions sufficient to obtain an aminoaromatic compound or a hydroxyaromatic compound.

2. The method of claim 1, wherein the metal of the metal aromatic compound is attached to one of the carbon atoms of the aromatic ring.

3. The method of claim 1, wherein the metal of the metal aromatic compound is a magnesium halide or lithium.

4. The method of claim 1, wherein the metal aromatic compound is substituted.

5. The method of claim 4, wherein the metal aromatic compound is substituted with a substituent wherein the substituent is amino, aminosulfonyl, carboxy, cyano, halo, hydroxy, hydroxyamino, hydroxysulfonyl, mercapto, nitro, oxo, or thio; or acyl$_{(C \leq 8)}$, alkoxy$_{(C \leq 8)}$, cycloalkoxy$_{(C \leq 8)}$, alkenyloxy$_{(C \leq 8)}$, aryloxy$_{(C \leq 8)}$, aralkoxy$_{(C \leq 8)}$, acyloxy$_{(C \leq 8)}$, cycloalkylalkoxy$_{(C \leq 8)}$, heterocycloalkylalkoxy$_{(C \leq 8)}$, heterocycloalkoxy$_{(C \leq 8)}$, alkylthio$_{(C \leq 8)}$, cycloalkylthio$_{(C \leq 8)}$, amido$_{(C \leq 8)}$, alkylamino$_{(C \leq 8)}$, dialkylamino$_{(C \leq 8)}$, alkylsulfonyl$_{(C \leq 8)}$, arylsulfonyl$_{(C \leq 8)}$, or a substituted version of these groups, or a protected amine group, a protected hydroxyl group, or a protected thiol group.

6. The method of claim 1, wherein one of the carbon atoms adjacent to the oxazridine group of the oxazridine compound is a quaternary substituted carbon atom.

7. The method of claim 1, wherein the oxazridine compound is further defined as:

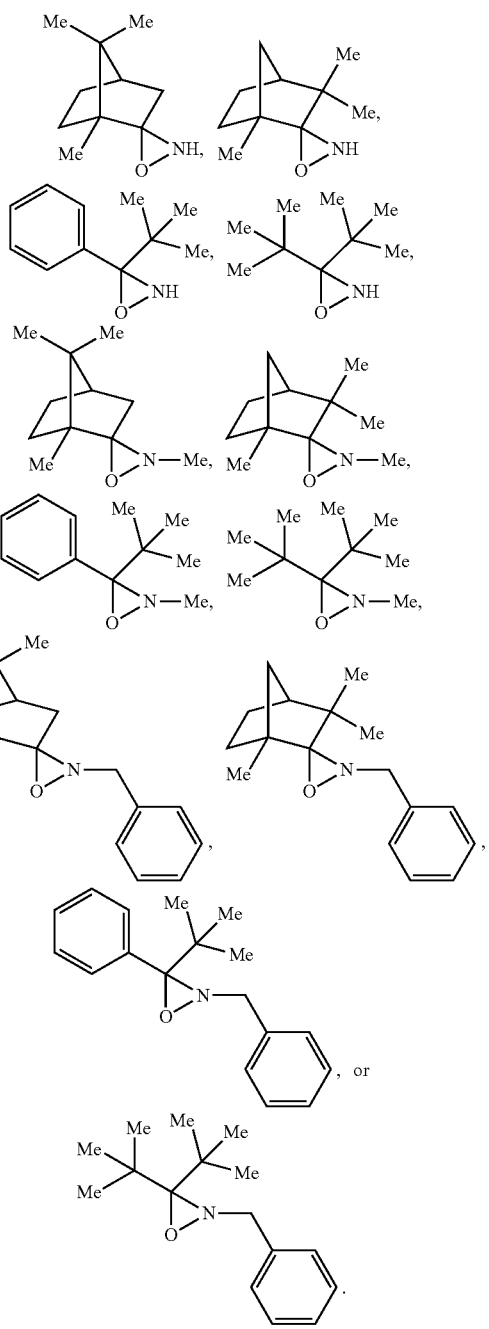

8. The method of claim 1, wherein the weak acid is an acid with a pKa of less than 12.

9. The method of claim 1, wherein the reaction mixture comprises an organic solvent.

10. The method of claim 9, wherein the organic solvent is a mixture of two or more solvents.

11. The method of claim 1, wherein the oxaziridine compound is added to the reaction mixture in an amount from about 0.5 equivalent to about 2.5 equivalent relative to the aromatic compound.

12. The method of claim 1, wherein when the $R_2$ of the oxaziridine compound is a hydrogen, the reaction produces an aminoaromatic compound.

13. The method of claim 1, wherein when the $R_2$ of the oxaziridine compound is not a hydrogen, the reaction produces a hydroxyaromatic compound.

14. A method of preparing an aminoaromatic compound comprising:
(A) admixing a metal aromatic compound with an oxaziridine compound in presence of a copper reagent to form a first reaction mixture under conditions sufficient to cause a reaction to obtain an anionic intermediate; wherein the oxaziridine compound is further defined as:

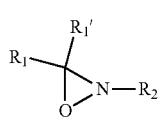

(I)

wherein:
$R_1$ and $R_1'$ are each independently alkyl$_{(C \leq 12)}$, cycloalkyl$_{(C \leq 12)}$, aryl$_{(C \leq 12)}$, or a substituted version of any of these groups, or $R_1$ and $R_1'$ are taken together and are a cycloalkanediyl$_{(C \leq 18)}$ or substituted cycloalkanediyl$_{(C \leq 18)}$; and
$R_2$ is hydrogen or alkyl$_{(C \leq 12)}$, aryl$_{(C \leq 12)}$, aralkyl$_{(C \leq 12)}$, or a substituted version of any of these three groups;
(B) admixing a weak acid with the anionic intermediate to obtain a second reaction mixture under conditions sufficient to obtain an aminoaromatic compound.

15. The method of claim 14, wherein the oxazridine compound is further defined as:

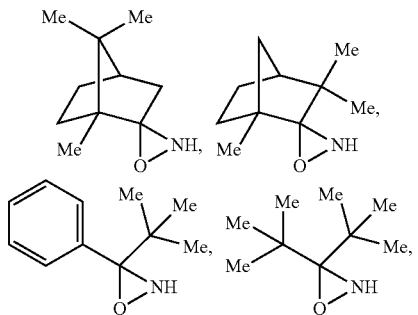

-continued

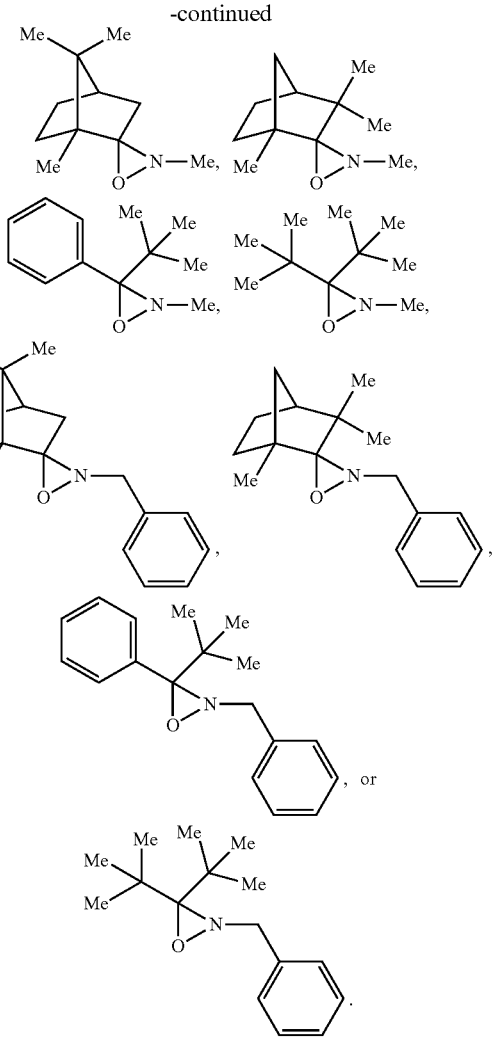

16. The method of claim 14, wherein the copper reagent is a Cu(I) salt.

* * * * *